United States Patent [19]

Hazel et al.

[11] Patent Number: 5,922,538
[45] Date of Patent: Jul. 13, 1999

[54] **GENETIC MARKERS AND METHODS FOR THE DETECTION OF *LISTERIA MONOCYTOGENES* AND *LISTERIA SPP***

[75] Inventors: James William Hazel, Conowingo, Md.; Mark Anton Jensen, West Chester, Pa.

[73] Assignee: E.I. du Pont de Nemours and Company, Wilmington, Del.

[21] Appl. No.: 08/766,439

[22] Filed: Dec. 12, 1996

Related U.S. Application Data

[63] Continuation-in-part of application No. 08/745,228, Nov. 8, 1996., abandoned

[51] Int. Cl.$^6$ .............................. C12Q 1/68; C07H 21/04; C07H 21/02
[52] U.S. Cl. ........................... 435/6; 536/23.1; 536/24.32
[58] Field of Search ................................ 435/6; 536/23.1, 536/24.32, 23.7; 935/77, 78

[56] References Cited

U.S. PATENT DOCUMENTS

| | | | |
|---|---|---|---|
| 4,717,653 | 1/1988 | Webster, Jr. | 435/5 |
| 5,087,558 | 2/1992 | Webster, Jr. | 435/5 |
| 5,126,239 | 6/1992 | Livak et al. | 435/6 |
| 5,340,728 | 8/1994 | Grosz et al. | 435/91.2 |
| 5,376,528 | 12/1994 | King et al. | 435/6 |
| 5,401,631 | 3/1995 | Lane et al. | 435/6 |
| 5,523,205 | 6/1996 | Cossart et al. | 435/6 |

FOREIGN PATENT DOCUMENTS

| | | |
|---|---|---|
| 2055302 | 11/1991 | Canada . |
| 2102963 | 11/1993 | Canada . |
| 0 517 154 A1 | 6/1992 | European Pat. Off. . |
| 0 543 484 A2 | 8/1992 | European Pat. Off. . |
| 0 517 361 A1 | 12/1992 | European Pat. Off. . |
| 0 576 842 A2 | 6/1993 | European Pat. Off. . |
| 05219997 | 8/1993 | Japan . |
| WO 90/11370 | 10/1990 | WIPO . |
| WO 92/03567 | 3/1992 | WIPO . |
| WO 92/07095 | 4/1992 | WIPO . |
| WO 92/07948 | 5/1992 | WIPO . |
| WO 92/14844 | 9/1992 | WIPO . |
| WO 95/33854 | 12/1995 | WIPO . |

OTHER PUBLICATIONS

Symposium, "DNA probes: An Overview and Comparison with Current Methods", Russel K. Enns, PhD, Laboratory Medicine, vol. 19, No. 5, May 1988, pp. 295–300.
"Detection of Ribosomal Nucleic Acid Homologies", M. Mordarski, 1985, pp. 41–66.
J. Mol. Biol. (1975), 98, 503–517, "Detection of Specific Sequences Among DNA Fragments Separated by Gel Electrophoresis".
Am. J. Hum. Genet, vol. 32, pp. 314–331, 1980, "Construction of a Genetic Linkage Map in Man Using Restriction Fragment Length Polymorphins".
Nucleic Acid Research, vol. 18, No. 22, pp. 6531–6535, "DNA Polymorphisms Amplified by Arbitrary Primers are Useful as Genetic Markers".

*Primary Examiner*—Eggerton A. Campbell

[57] ABSTRACT

A method, diagnostic sequences and primers are provided that are useful in identifying the *Listeria monocytogenes* and Listeria spp. The method involves identifying a RAPD-amplified DNA fragment common to *Listeria monocytogenes*, then identifying the most conserved regions of that DNA fragment, and the preparing specific primers useful for detecting the presence of a marker within the fragment whereby that set of primers is then useful in the identification of all *Listeria monocytogenes*. Markers within the same fragment that are specific to the Listeria genus are also identified and are useful for the identification of all Listeria spp.

17 Claims, 13 Drawing Sheets

FIG. 2

```
L. monocytogenes #647  Met Thr Asn Ala Asn Gly Asn Leu Lys Lys Cys Pro Ile Thr Ile Ser Ser Tyr
L. innocua #4450       Met Thr Asn Ala Asn Gly Asp Leu Lys Lys Cys Pro Ile Thr Ile Ser Ser Tyr
L. ivanovii #3340      Met Thr Asn Ala Asn Gly Asn Leu Lys Lys Cys Pro Ile Thr Ile Ser Ser Tyr
L. seeligeri #3327     Met Thr Asn Val Asn Gly Asp Leu Lys Lys Cys Pro Ile Thr Ile Ser Ser Tyr
L. welshimeri #3359    Met Thr Asn Ser Asn Gly Asn Leu Lys Lys Cys Pro Ile Thr Ile Ser Ser Tyr L. monocytogenes #647  Thr Leu Gly Thr Glu Val Ser Phe Pro Lys Arg Val Lys Val Ala Ala Glu Asn
L. innocua #4450       Thr Leu Gly Thr Glu Val Ser Phe Pro Glu Arg Val Arg Ile Ala Ala Glu Asn
L. ivanovii #3340      Thr Leu Gly Thr Glu Val Ser Phe Pro Glu Arg Val Arg Ile Ala Ala Glu Asn
L. seeligeri #3327     Thr Leu Gly Thr Glu Val Ser Phe Pro Glu Arg Val Arg Ile Ala Ala Glu Asn
L. welshimeri #3359    Thr Leu Gly Thr Glu Val Ser Phe Pro Glu Arg Val Lys Ile Ala Ala Glu Asn L. monocytogenes #647  Gly Phe Asp Gly Ile Gly Leu Arg Ala Glu Asn Tyr Val Asp Ala Leu Ala Ala
L. innocua #4450       Gly Phe Asp Gly Ile Gly Leu Arg Ala Glu Asn Tyr Val Asp Ala Leu Ala Ala
L. ivanovii #3340      Gly Phe Asp Gly Ile Gly Leu Arg Ala Glu Asn Tyr Val Asp Ala Leu Ala Ala
L. seeligeri #3327     Gly Phe Asp Gly Ile Gly Leu Arg Ala Glu Asn Tyr Val Asp Ala Leu Ala Ala
L. welshimeri #3359    Gly Phe Asp Gly Ile Gly Leu Arg Ala Glu Asn Tyr Val Asp Ala Leu Ala Ala L. monocytogenes #647  Gly Leu Thr Asp Glu Asp Met Leu Arg Ile Leu Asp Glu His Asn Met Lys Val
L. innocua #4450       Gly Leu Thr Asp Glu Asp Met Leu Arg Ile Leu Asp Glu His Asn Ile Lys Val
L. ivanovii #3340      Gly Leu Thr Asp Glu Asp Met Leu Arg Ile Leu Asp Glu His His Ile Lys Val
L. seeligeri #3327     Gly Leu Thr Asp Glu Asp Met Leu Arg Ile Leu Asp Glu His His Ile Lys Val
L. welshimeri #3359    Gly Leu Thr Asp Asn Asp Met Leu Gln Ile Leu Asp Lys His Asn Ile Lys Val L. monocytogenes #647  Thr Glu Val Glu Tyr Ile Thr Gln Trp Gly Thr Ala Glu Asp Arg Thr Ala Glu
L. innocua #4450       Thr Glu Val Glu Tyr Ile Thr Gln Trp Gly Thr Ala Glu Asp Arg Thr Ala Glu
L. ivanovii #3340      Thr Glu Val Glu Tyr Ile Thr Gln Trp Gly Thr Ala Glu Asp Arg Thr Ala Glu
L. seeligeri #3327     Thr Glu Val Glu Tyr Ile Thr Gln Trp Gly Thr Ala Ser Asp Arg Thr Phe Glu
L. welshimeri #3359    Thr Glu Val Glu Tyr Ile Thr Gln Trp Gly Thr Ala Ser Asp Arg Thr Lys Glu
                                                                     Glu Ala Asp Arg Thr Asp Ala
```

```
L. monocytogenes #647   Gln Gln Lys Lys Glu Gln Thr Thr Phe His Met Ala Arg Leu Phe Gly Val Lys
L. innocua #4450        Gln Gln Lys Lys Glu Gln Thr Thr Phe His Met Ala Arg Leu Phe Gly Val Lys
L. ivanovii #3340       Gln Gln Lys Lys Glu Gln Thr Thr Phe His Met Ala Arg Leu Phe Gly Val Lys
L. seeligeri #3327      Gln Gln Lys Lys Glu Gln Thr Thr Phe His Met Ala Arg Leu Phe Gly Val Lys
L. welshimeri #3359     Gln Gln Gln Lys Glu Gln Thr Thr Phe His Met Ala Arg Leu Phe Gly Val Lys L. monocytogenes #647   His Ile Asn Cys Gly Leu Leu Glu Lys Ile Pro Glu Gln Ile Ile Val Ala
L. innocua #4450        His Ile Asn Cys Gly Leu Leu Glu Lys Ile Pro Glu Gln Ile Ile Thr Ala
L. ivanovii #3340       His Ile Asn Cys Gly Leu Leu Glu Lys Ile Pro Glu Asp Gln Ile Ile Thr Ala
L. seeligeri #3327      His Ile Asn Cys Gly Leu Leu Glu Lys Ile Pro Glu Gln Ile Ile Thr Ala
L. welshimeri #3359     His Ile Asn Cys Gly Leu Leu Glu Lys Ile Pro Glu Gln Ile Ile Thr Ala L. monocytogenes #647   Leu Gly Glu Leu Cys Asp Arg Ala Glu Leu Ile Ile Gly Leu Glu Phe Met
L. innocua #4450        Leu Gly Glu Leu Cys Asp Arg Ala Glu Leu Ile Ile Gly Leu Glu Phe Met
L. ivanovii #3340       Leu Gly Glu Leu Cys Asp Arg Ala Glu Leu Ile Ile Gly Leu Glu Phe Met
L. seeligeri #3327      Leu Gly Glu Leu Cys Asp Arg Ala Glu Leu Ile Ile Gly Leu Glu Phe Met
L. welshimeri #3359     Leu Gly Glu Leu Cys Asp Arg Ala Glu Leu Ile Ile Gly Leu Glu Phe Met L. monocytogenes #647   Pro Tyr Ser Gly Val Ala Asp Leu Gln Ala Ala Trp Arg Val Ala Glu Ala Cys
L. innocua #4450        Pro Tyr Ser Gly Val Ala Asp Leu Ala Ala Ala Trp Arg Val Ala Glu Ala Cys
L. ivanovii #3340       Pro Tyr Ser Gly Val Ala Asp Leu Ala Ala Ala Trp Arg Val Ala Glu Ala Cys
L. seeligeri #3327      Pro Tyr Ser Gly Val Ala Asp Leu Ala Ala Ala Trp Arg Val Ala Glu Ala Cys
L. welshimeri #3359     Pro Tyr Ser Gly Val Ala Asp Leu Ala Ala Ala Trp Arg Val Ala Glu Ala Cys L. monocytogenes #647   Gly Arg Asp Asn Ala Gln Leu Ile Cys Asp Thr Trp His Trp Ala Arg Ala Asn
L. innocua #4450        Gly Arg Asp Asn Ala Gln Leu Ile Cys Asp Thr Trp His Ser Ala Arg Ala Asn
L. ivanovii #3340       Gly Arg Asp Asn Ala Gln Leu Ile Cys Asp Thr Trp His Trp Ala Arg Ala Asn
L. seeligeri #3327      Gly Arg Asp Asn Ala Gln Leu Ile Cys Asp Thr Trp His Trp Ala Arg Ala Asn
L. welshimeri #3359     Gly Arg Asp Asn Ala Gln Leu Ile Cys Asp Thr Trp His Trp Ala Arg Ala Asn
```

```
L. monocytogenes #647   Gln Thr Ala Glu Ser Ile Lys Asn Val Pro Ala Asp Arg Ile Val Ser Ile Gln
L. innocua #4450        Gln Thr Ala Glu Ser Ile Lys Asn Val Pro Ala Asp Arg Ile Val Ser Ile Gln
L. ivanovii #3340       Gln Thr Ala Glu Ser Ile Lys Asn Val Pro Ala Asp Arg Ile Val Ser Ile Gln
L. seeligeri #3327      Gln Thr Ala Glu Ser Ile Lys Asn Ile Pro Ala Asp Arg Ile Val Ser Ile Gln
L. welshimeri #3359     Gln Thr Ala Glu Ser Ile Lys Asn Val Pro Ala Asp Arg Ile Val Ser Ile Gln L. monocytogenes #647   Leu Cys Asp Val His Glu Thr Pro Tyr Lys Glu Leu Arg Glu Glu Ser Leu His
L. innocua #4450        Leu Cys Asp Val His Glu Thr Pro Tyr Lys Glu Leu Arg Glu Glu Ser Leu His
L. ivanovii #3340       Leu Cys Asp Val His Glu Thr Pro Tyr Lys Glu Leu Arg Glu Glu Ser Leu His
L. seeligeri #3327      Leu Cys Asp Val His Glu Thr Pro Tyr Lys Glu Leu Arg Glu Glu Ser Leu His
L. welshimeri #3359     Leu Cys Asp Val His Glu Thr Pro Tyr Lys Glu Leu Arg Glu Glu Ser Leu His L. monocytogenes #647   Asp Arg Leu Ala Pro Gly Glu Gly Tyr Gly Asp Thr Val Gly Phe Ala Lys Ile
L. innocua #4450        Asp Arg Leu Ala Pro Gly Glu Gly Tyr Gly Asp Thr Val Gly Phe Ala Arg Ile
L. ivanovii #3340       Asp Arg Leu Ala Pro Gly Glu Gly Tyr Gly Asp Thr Ile Gly Phe Ala Arg Ile
L. seeligeri #3327      Asp Arg Leu Ala Pro Gly Glu Gly Tyr Gly Asp Thr Val Gly Phe Ala Arg Ile
L. welshimeri #3359     Asp Arg Leu Pro Pro Gly Glu Gly Tyr Gly Asp Thr Val Gly Phe Ala Arg Ile L. monocytogenes #647   Leu Lys His Gly Val Asn Pro Arg Val Met Gly Val Glu Val Ile Ser Asp
L. innocua #4450        Leu Lys Glu His Gly Val Asn Pro Arg Val Met Gly Val Glu Val Ile Ser Asp
L. ivanovii #3340       Leu Lys Glu His Gly Val Ser Pro Arg Val Met Gly Val Glu Val Ile Ser Asp
L. seeligeri #3327      Leu Lys Glu His Gly Val Asn Pro Arg Val Met Gly Val Glu Val Ile Ser Asp
L. welshimeri #3359     Leu Lys Glu His Gly Val Asn Pro Arg Val Met Gly Val Glu Val Ile Ser Asp L. monocytogenes #647   Ser Met Val Ala Thr Gly Leu Glu Tyr Ala Ala Leu Lys Val Tyr Asn Ala Thr
L. innocua #4450        Ser Met Val Glu Thr Gly Leu Glu Tyr Ala Ala Ile Lys Val Tyr Asn Ala Thr
L. ivanovii #3340       Ser Met Val Glu Thr Gly Leu Glu Tyr Ala Ala Ile Lys Val Tyr Asn Ala Thr
L. seeligeri #3327      Ser Met Val Glu Thr Gly Leu Glu Tyr Thr Ala Ile Lys Val Tyr Asn Ala Thr
L. welshimeri #3359     Ser Met Val Glu Thr Gly Leu Glu Tyr Ala Ala Ile Lys Val Tyr Asn Ala Thr L. monocytogenes #647   Lys Val Leu Asp Glu Ala Trp Pro Glu Ile Ser Pro Arg TER (SEQ ID NO: 41)
L. innocua #4450        Lys Val Leu Asp Gln Ala Trp Pro Glu Ile Ser Pro Lys TER (SEQ ID NO: 42)
L. ivanovii #3340       Lys Val Leu Asp Glu Ala Trp Pro Glu Val Ser Pro Lys TER (SEQ ID NO: 43)
L. seeligeri #3327      Lys Val Leu Asp Glu Ala Trp Pro Glu Val Ser Pro Lys TER (SEQ ID NO: 44)
L. welshimeri #3359     Lys Val Leu Asp Glu Ala Trp Pro Glu Ile Ser Pro Lys TER (SEQ ID NO: 45)
```

```
1515(rc341x2)-26-363        GCG ATA CGA CAA ATC TGT TAG GCA CC    (SEQ ID NO: 46)
L. monocytogenes #647       GCG ATA CGA CAA ATC TGT TAG GCA CC    (SEQ ID NO: 46)
L. innocua #4450            GAG ATA CAA CAA AAC GAT TTG GTA CT    (SEQ ID NO: 47)
L. seeligeri #3327          GCG AAA CCA CAA AAC GGT TTG GCA CA    (SEQ ID NO: 48)
L. welsh. #3359             GAG ATA CAA CAA ACC GAT TAG GTA CT    (SEQ ID NO: 49)
L. ivanovii #3340           GCG AAA CAA CAA AAC GGT TAG GTA CT    (SEQ ID NO: 50)

1515(rc341x2)-27-281        CAT TCC TTT CAC AGG  GAG TCT TCC TAC             (SEQ ID NO: 51)
L. monocytogenes #647       CAT TCC TTT CAC AGG  GAG TCT TCC TAC             (SEQ ID NO: 51)
L. monocytogenes #1324      CAT TCC TTT CAC AGG  GAG TCT TCC TAC             (SEQ ID NO: 51)
L. innocua #4450            CTT TCC CTTT CA- AGGTA GAA TCT TCT TGT           (SEQ ID NO: 52)
L. seeligeri #3327          CTT TTC CTTT CAG AGGGG GAT TTT T--A-             (SEQ ID NO: 53)
L. welsh. #3359             CTT TCC CTTT CA- AGATG GAA TCT AG-AT             (SEQ ID NO: 54)
L. ivanovii #3340           CTT TCC CTTT CA- AGATA GAA TTT TTT CTT           (SEQ ID NO: 55)

1515-26-36                  TAG TTG GAT GGA AAC AAT CCG ATC AG    (SEQ ID NO: 56)
L. monocytogenes #647       TAG TTG GAT GGA AAC AAT CCG ATC AG    (SEQ ID NO: 56)
L. monocytogenes #1324      TAG TTG GAT AGA AAC AAT CCG ATC AG    (SEQ ID NO: 57)
L. innocua #4450            TAA TTG GAT GGA AAC AAT CCG ATC AG    (SEQ ID NO: 58)
L. seeligeri #3327          AAG TTG AAT AGA CAC AAT CCG GTC AG    (SEQ ID NO: 59)
L. welsh. #3359             CAA TTG GAT AGA AAC AAT TCG ATC AG    (SEQ ID NO: 60)
L. ivanovii #3340           GAG TTG AAT AAT TGA AAC AAT CCG ATC AG (SEQ ID NO: 61)

1515-27-357                 TTT GTT GTT CTG CTG TAC GAT CTT CGG   (SEQ ID NO: 62)
L. monocytogenes #647       TTT GTT GTT CTG CTG TAC GAT CTT CGG   (SEQ ID NO: 62)
L. monocytogenes #1324      TTT GTT GTT CTG CTG TAC GAT CTT CGG   (SEQ ID NO: 62)
L. innocua #4450            TTT GCT GTT CGG CTG TGC GGT CCT CGG   (SEQ ID NO: 63)
L. seeligeri #3327          TTT GTT GTT CTT TGG TGC GGT CGG AAG   (SEQ ID NO: 64)
L. welsh. #3359             GTT GTT GAG CAT CGG TTC GGT CTG CTT   (SEQ ID NO: 65)
L. ivanovii #3340           TTT GTT GCT CGA AAG TGC GGT CAG AAG   (SEQ ID NO: 66)
```

```
1515-26-rc233
L. monocytogenes #647    AAA TCC CTG AGG AAC AAA TCA TCG TC    (SEQ ID NO: 67)
L. monocytogenes #1324   AAA TCC CTG AGG AAC AAA TCA TCG TC    (SEQ ID NO: 67)
L. innocua #4450         AAA TCC CTG AGG AAC AAA TCA TCG TC    (SEQ ID NO: 68)
L. seeligeri #3327       AAA TCC CCG AGG AAC AAA TCA TTG TC    (SEQ ID NO: 69)
L. welsh. #3359          AGA TCC CGG AAG AAC AAA TCA TTA CG    (SEQ ID NO: 70)
L. welsh. #3359          AAA TTC CAG AAG AGC AAA TAA TTA CT    (SEQ ID NO: 71)
L. ivanovii #3340        AAA TCC CCG AAG AGC AAA TCA TTA CT    (SEQ ID NO: 72)

1515(8585)-27-rc737
L. monocytogenes #647    GGT AGA ATA GGT TAA CTG TCC AGT TCC   (SEQ ID NO: 73)
L. monocytogenes #1324   GGT AGA ATA GGT TAA CTG TCC AGT TCC   (SEQ ID NO: 73)
L. innocua #4450         GGT AGA ATA GGT TAA CTG TCC AGT TCC   (SEQ ID NO: 73)
L. seeligeri #3327       GGT AGA ATA CGT TAA CTG TCC AGT TGA   (SEQ ID NO: 74)
L. welsh. #3359          GGT AGA ATI CGA AAA CTG TCC AGT CAG   (SEQ ID NO: 75)
L. welsh. #3359          GGT AGA ATA CGT TAA CTG TCC AGT TGT   (SEQ ID NO: 76)
L. ivanovii #3340        GGT AGA ATG TGA AAA CTG TCC AGT CAA   (SEQ ID NO: 77)

1515(8585)-28-rc793
L. monocytogenes #647    TAC AAT TAG ACT GTA GTT ACG CCA GTG A  (SEQ ID NO: 78)
L. monocytogenes #1324   TAC AAT TAG ACT GTA GTT ACG CCA GTG A  (SEQ ID NO: 78)
L. innocua #4450         TAC AAT TAG ACT GTA GTT ACG CCA GTG A  (SEQ ID NO: 79)
L. seeligeri #3327       TAC AAT TAG ACT GTA GTT ACA CCA GCA G  (SEQ ID NO: 80)
L. welsh. #3359          TAC AAT TAG ACT GTA ATT AAG CCA GTG A  (SEQ ID NO: 81)
L. welsh. #3359          TAC AAT TAG ACT GTA GTT ACA CCA GCA G  (SEQ ID NO: 82)
L. ivanovii #3340        TAC AAT TAG ACA GTA GTT ATG CCA GTG A  (SEQ ID NO: 83)
```

| 1515-30-76 | | |
|---|---|---|
| L. monocytogenes #647. | TTT GAT AGA TTC TGC TGT TTG GTT TGC TCT | (SEQ ID NO: 84) |
| L. monocytogenes #1324. | TTT GAT AGA TTC TGC TGT TTG GTT TGC TCT | (SEQ ID NO: 84) |
| L. innocua #4450 | TTT GAT AGA TTC AGC TGT TTG ATT TGC TCT | (SEQ ID NO: 85) |
| L. seeligeri #3327 | TTT GAT IGA TTC TGC TGT TTG GTT TGC TCT | (SEQ ID NO: 86) |
| L. ivanovii #3340 | TTT GAT AGA TTC TGC TGT TTG ATT TGC TCT | (SEQ ID NO: 87) |
| L. welshimeri #3359 | TTT GAT AGA TTC TGC TGT TTG GTT TGC TCT | (SEQ ID NO: 84) |
|  | TTT GAT AGA CTC TGC TGT TTG GTT TGC TCT | (SEQ ID NO: 88) |

| 1515-30-88 | | |
|---|---|---|
| L. monocytogenes #647. | TGC TGT TTG GTT TGC TCT AGC CCA GTG CCA | (SEQ ID NO: 89) |
| L. monocytogenes #1324 | TGC TGT TTG GTT TGC TCT AGC CCA GTG CCA | (SEQ ID NO: 89) |
| L. innocua #4450 | AGC TGT TTG ATT TGC TCT AGC CCA GTG CCA | (SEQ ID NO: 90) |
| L. seeligeri #3327 | TGC TGT TTG GTT TGC TCT AGC CGA GTG CCA | (SEQ ID NO: 91) |
| L. ivanovii #3340 | TGC TGT TTG ATT TGC TCT AGC CCA GTG CCA | (SEQ ID NO: 92) |
| L. welshimeri #3359 | TGC TGT TTG GTT TGC TCT IGC CCA GTG CCA | (SEQ ID NO: 93) |
|  | TGC TGT TTG GTT TGC TCT IGC CCA GTG CCA | (SEQ ID NO: 93) |

| 1515(8585)-30-624 | | |
|---|---|---|
| L. monocytogenes #647. | TTG CAT TTG TCA TAA AAA TTA TCT CCT CTC | (SEQ ID NO: 94) |
| L. monocytogenes #1324 | TTG CAT TTG TCA TAA AAA TTA TCT CCT CTC | (SEQ ID NO: 94) |
| L. innocua #4450 | TTG CAT TTG TCA TAA AAA TTA TCT CCT CTC | (SEQ ID NO: 94) |
| L. seeligeri #3327 | TTA CAT TTG TCA TAA AAA TTA TCT CCT CTC | (SEQ ID NO: 95) |
| L. ivanovii #3340 | TTG CAT TTG TCA TAA AAA TTA TCT CCT CTC | (SEQ ID NO: 94) |
| L. welshimeri #3359 | TTG AAT TTG TCA TAA AAA TTA TCT CCT CTC | (SEQ ID NO: 96) |

| 1515(8585)-30-rc483 | | |
|---|---|---|
| L. monocytogenes #647 | CGC TGC GGA AAA CGG TTT TGA CGG ATT TGG | (SEQ ID NO: 97) |
| L. monocytogenes #1324 | CGC TGC GGA AAA CGG TTT TGA CGG ATT TGG | (SEQ ID NO: 97) |
| L. innocua #4450 | CGC TGC GGA AAA AGG TTT TGA CGG ATT TGG | (SEQ ID NO: 98) |
| L. seeligeri #3327 | CGC AGC AAA CGG TTT TGA IGG ATT TGG | (SEQ ID NO: 99) |
| L. ivanovii #3340 | CGC AGC AGA AAA CGG TTT TGA IGG ATT TGG | (SEQ ID NO: 99) |
| L. welshimeri #3359 | IGC AGC AGA AAA CGG TTT TGA CGG ATT TGG | (SEQ ID NO: 100) |
|  | IGC AGC AGA AAA CGG TTT TGA CGG ATT TGG | (SEQ ID NO: 100) |

FIG. 6

| | | |
|---|---|---|
| 1515(8585)-30-rc555 | AAA AAA ATG CCC CAT CAC GAT TAG CTC TTA | (SEQ ID NO: 101) |
| L. monocytogenes #647 | AAA AAA ATG CCC CAT CAC GAT TAG CTC TTA | (SEQ ID NO: 101) |
| L. monocytogenes #1324 | AAA AAA ATG CCC CAT CAC GAT TAG CTC TTA | (SEQ ID NO: 101) |
| L. innocua #4450 | AAA AAA ATG CCC AAT CAC GAT CTC TTA | (SEQ ID NO: 102) |
| L. seeligeri #3327 | AAA AAA ATG CCC CAT CAC GAT TAG TTC TTA | (SEQ ID NO: 103) |
| L. ivanovii #3340 | AAA AAA ATG CCC CAT CAC GAT TAG CTC TTA | (SEQ ID NO: 101) |
| L. welshimeri #3359 | AAA AAA ATG CCC CAT CAC GAT TAG TTC TTA | (SEQ ID NO: 103) |
| | | |
| 1515(8585)-30-rc573 | AAA TGC AAA TGG CAA CCT AAA AAA ATG CCC | (SEQ ID NO: 104) |
| L. monocytogenes #647 | AAA TGC AAA TGG CAA CCT AAA AAA ATG CCC | (SEQ ID NO: 104) |
| L. monocytogenes #1324 | AAA TGC AAA TGG CAA ICT AAA AAA ATG CCC | (SEQ ID NO: 105) |
| L. innocua #4450 | AAA TGC AAA TGG CGA CCT AAA AAA ATG CCC | (SEQ ID NO: 106) |
| L. seeligeri #3327 | AAA TGT AAA TGG CGA CTT AAA AAA ATG CCC | (SEQ ID NO: 107) |
| L. ivanovii #3340 | AAA TGC AAA TGG CAA CCT AAA AAA ATG CCC | (SEQ ID NO: 104) |
| L. welshimeri #3359 | AAA TTC AAA TGG CAA CTT AAA AAA ATG CCC | (SEQ ID NO: 108) |
| | | |
| 1515(8585)-30-rc824 | CAA TAC CAA TTT GTT TTT ATG GAA TAG TCA | (SEQ ID NO: 109) |
| L. monocytogenes #647 | CAA TAC CAA TTT GTT TTT ATG GAA TAG TCA | (SEQ ID NO: 109) |
| L. monocytogenes #1324 | CAA TAC CAA TTT GTT TTT ATG GAA TAG TCA | (SEQ ID NO: 109) |
| L. innocua #4450 | IAA TAC CAA TTT GTT TTT ATG GAA TAG TCA | (SEQ ID NO: 110) |
| L. seeligeri #3327 | IAA TAC CAA TTT GTT TTT ATG GAA TAG TCA | (SEQ ID NO: 110) |
| L. ivanovii #3340 | IAA TAC CAA TTT GTT TTT ATG GAA TAG TCA | (SEQ ID NO: 110) |
| L. welshimeri #3359 | IAA TAC CAA TTT GTT TTT ATG GAA TAG TCA | (SEQ ID NO: 110) |

GENETIC MARKERS AND METHODS FOR THE DETECTION OF *LISTERIA MONOCYTOGENES* AND *LISTERIA SPP*

This is a continuation-in-part of application Ser. No. 08/745,228, filed Nov. 8, 1996, abandoned.

FIELD OF INVENTION

The invention relates to the field of molecular biology and the use of randomly amplified nucleic acid fragments (RAPD) for the selection of genetic markers useful in the identification of bacteria. More specifically, the invention relates to specific DNA marker sequences useful for the detection of *Listeria monocytogenes* and Listeria spp. and use of those diagnostic markers to determine if an unknown bacterium is a member of either *Listeria monocytogenes* or Listeria spp.

BACKGROUND

Central to the field of microbiology is the ability to positively identify microorganisms at the level of genus, species or serotype. Correct identification is not only an essential tool in the laboratory, but it plays a significant role in the control of microbial contamination in the processing of food stuffs, the production of agricultural products, and the monitoring of environmental media such as ground water. Increasing stringency in regulations that apply to microbial contamination have resulted in a corresponding increase in industry resources which must be dedicated to contamination monitoring.

Of greatest concern is the detection and control of pathogenic microorganisms. Although a broad range of microorganisms have been classified as pathogenic, attention has primarily focused on a few bacterial groupings such as Escherichia, Salmonella, Listeria and Clostridia. Typically, pathogen identification has relied on methods for distinguishing phenotypic aspects such as growth or motility characteristics, and for immunological and serological characteristics. Selective growth procedures and immunological methods are the traditional methods of choice for bacterial identification and these can be effective for the presumptive detection of a large number of species within a particular genus. However, these methods are time consuming and are subject to error. Selective growth methods require culturing and subculturing in selective media, followed by subjective analysis by an experienced investigator. Immunological detection (e.g., ELISA) is more rapid and specific, however, it still requires growth of a significant population of organisms and isolation of the relevant antigens. For these reasons interest has turned to detection of bacterial pathogens on the basis of nucleic acid sequence.

It is well known, for example, that nucleic acid sequences associated with the ribosomes of bacteria are often highly conserved across genera and are therefore useful for identification (Webster, U.S. Pat. No. 4,717,653 and U.S. Pat. No. 5,087,558; Enns, *Lab. Med.*, 19, 295, (1988); Mordarski, *Soc. Appl. Bacteriol. Tech.* Ser., 20 (Chem. Methods Bact. Syst.), 41, (1985)). Weisburg et al. (EP 51736) disclose a method for the detection and identification of pathogenic microorganisms involving the PCR amplification and labeling of a target nucleotide for hybridization to 16S rDNA of *E. coli*. Lane et al. (WO 9015157) teach universal nucleic acid probes that hybridize to conserved regions of 23S or 16S rRNA of eubacteria.

Although bacterial ribosomal nucleic acids contain highly conserved sequences, they are not the only sources of base sequence conservation that is useful for microorganism identification. Wheatcroft et al. (CA 2055302) describe the selection of transposable elements, flanked by unique DNA sequences, for the detection of various Rhizobium strains. Similarly, Tommassen et al. (WO 9011370) disclose polynucleotide probes and methods for the identification and detection of gram-positive bacteria. The method of Tommassen et al. relies on probes corresponding to relatively short fragments of the outer membrane protein, OmpA, which is known to be highly conserved throughout gram-positive genera. Atlas et al. (EP 517154) teach a nucleic acid hybridization method for the detection of Giardia sp. based on designing probes with sequences complementary to regions of the gene encoding the giardin protein. Webster et al. (U.S. Pat. No. 4,717,653) has expanded upon the use of rRNA in disclosing a method for the characterization of bacteria based on the comparison of the chromatographic pattern of restriction endonuclease-digested DNA from the unknown organism with equivalent chromatographic patterns of at least 2 known different organism species. The digested DNA has been hybridized or reassociated with ribosomal RNA information-containing nucleic acid from (or derived from) a known probe organism. The method of Webster et al. effectively establishes a unique bacterial nucleic acid "fingerprint" corresponding to a particular bacterial genus against which unknown "fingerprints" are compared.

Methods for the identification of *Listeria monocytogenes* on using specific hybridization probes or primers are known. For example, U.S. Pat. No. 5,523,205 and JP 05219997 teach DNA probes capable of hybridizing to a portion of the genome of pathogenic *Listeria monocytogenes*, but do not hybridize to genomes of other Listeria species. DE 4238699 and EP 576842 teach methods for detection of *Listeria monocytogenes* using primers designed to give amplification products specific to the *monocytogenes* genome. EP 576842 discusses a method for the detection of *L. monocytogenes* using amplification primers based on genes encoding the highly conserved iap (invasion-associated protein) of Listeria and WO 9008841 teaches nucleic acid probes capable of hybridizing to ribosomal RNA (rRNA) or rDNA of Listeria and not to rRNA or DNA of non-Listeria.

The methods described above are useful for the detection of bacteria, but each relies upon knowledge of a gene, protein, or other specific sequence known a priori to be highly conserved throughout a specific bacterial group. An alternative method would involve a nontargeted analysis of bacterial genomic DNA for specific non-phenotypic genetic markers common to all species of that bacteria. For example, genetic markers based on single point mutations may be detected by differentiating DNA banding patterns from restriction enzyme analysis. As restriction enzymes cut DNA at specific sequences, a point mutation within this site results in the loss or gain of a recognition site, giving rise in that region to restriction fragments of different length. Mutations caused by the insertion, deletion or inversion of DNA stretches will also lead to a length variation of DNA restriction fragments. Genomic restriction fragments of different lengths between genotypes can be detected on Southern blots (Southern, *J. Mol. Biol.* 98, 503, (1975)). The genomic DNA is typically digested with any restriction enzyme of choice, the fragments are electrophoretically separated, and then hybridized against a suitably labeled probe for detection. The sequence variation detected by this method is known as restriction length polymorphism or RFLP (Botstein et al., *Am. J. Hum. Genet.* 342, 314, (1980)). RFLP genetic markers are particularly useful in detecting genetic variation in phenotypically silent mutations and serve as highly accurate diagnostic tools.

Another method of identifying genetic polymorphic markers employs DNA amplification using short primers of arbitrary sequence. These primers have been termed "random amplified polymorphic DNA" or "RAPD" primers (see Williams et al., *Nucl. Acids. Res.,* 18, 6531 (1990) and U.S. Pat. No. 5,126,239; also EP 0 543 484 A2, WO 92/07095, WO 92/07948, WO 92/14844, and WO 92/03567). The RAPD method amplifies either double or single-stranded, nontargeted, arbitrary DNA sequences using standard amplification buffers, dATP, dCTP, dGTP and TTP, and a thermostable DNA polymerase such as Taq. The nucleotide sequence of the primers is typically about 9 to 13 bases in length, between 50 and 80% G+C in composition and contains no palindromic sequences. RAPD detection of genetic polymorphisms represents an advance over RFLP in that it is less time consuming, more informative, and readily susceptible to automation. Because of its sensitivity for the detection of polymorphisms, RAPD analysis and variations based on RAPD/PCR methods have become the methods of choice for analyzing genetic variation within species or closely related genera, both in the animal and plant kingdoms. For example, Landry et al. (*Genome,* 36, 580, (1993)) discuss the use of RAPD analysis to distinguish various species of minute parasitic wasps that are not morphologically distinct. Van Belkum et al. (*Mol. Biochem Parasitol.,* 61, 69, (1993)) teach the use of PCR-RAPD for the distinction of various species of Giardi.

In commonly assigned U.S. Pat. No. 5,340,728, Applicants disclosed a method of double-nested PCR which is used to detect the presence of a specific microbe. This disclosure first describes identifying a random, unique segment of DNA for each individual microorganism which will be diagnostic for that microorganism. To identify and obtain this diagnostic nucleic acid segment a series of polymorphic markers is generated from each organism of interest using single primer RAPD analysis. The RAPD series from each organism is compared to similarly generated RAPD series for other organisms, and a RAPD marker unique to all members of the group is then selected. The unique marker is then isolated, amplified and sequenced. Outer primers and inner primers suitable for double-nested PCR of each marker may then be developed. These primers comprise sequence segments within the RAPD markers, wherein the inner set of primers will be complementary to the 3' ends of the target piece of nucleic acid. These nested primers may then be used for nested PCR amplification to definitely detect the presence of a specific microorganism.

In commonly owned PCT U.S. 95/06704 (WO 95/33854), Applicants more particularly adapted and described this RAPD methodology to identify a sequence or marker. The presence of the marker is diagnostic for all individuals of the genus Salmonella. PCT U.S. 95/06704 teaches a method involving a RAPD amplification of genomic DNA of a representative number of Salmonella individuals to produce a RAPD amplification product, termed the diagnostic fragment. This diagnostic fragment must be present in the RAPD profiles in over 90% of the individuals tested. Sequence information from the diagnostic fragment enables identification of the most suitable PCR primer binding sites within the diagnostic fragment to define a unique diagnostic marker. Primers flanking this marker are useful for the generation of amplification products from Salmonella genomic DNA, but will not produce any amplification products in non-Salmonella genera.

In commonly owned U.S. Ser. No. 08/608,881, Applicants disclose a method, diagnostic sequences and primers that are useful in the identification of the *Escherichia coli* 0157:H7 serotype. The method involves the identification of a RAPD-amplified DNA fragment common to 0157:H7 *Escherichia coli,* the identification of the most conserved regions of that fragment, and the preparation of specific primers useful for detecting the presence of a marker within the fragment whereby that set of primers is then useful in the identification of all 0157:H7 *Escherichia coli.* The method of 08/608,881 does not teach markers useful for the specific identification of *Listeria monocytogenes* and Listeria spp.

A detection methodology using PCR/RAPD specific to *Listeria monocytogenes* and Listeria spp. would be of high utility in the food industry. Detection methods not dependent on sequences derived from a known gene or associated with a known phenotypic characteristic of *Listeria monocytogenes* and Listeria spp. have not previously been disclosed.

SUMMARY OF THE INVENTION

The present invention provides a method for the specific identification of *Listeria monocytogenes* and Listeria spp. using diagnostic genetic markers.

A method is provided for determining whether an unknown bacterium is a *Listeria monocytogenes* that involves:

(A) amplifying genomic DNA from (i) a positive test panel of *Listeria monocytogenes* strains and (ii) a negative test panel of non-*monocytogenes* Listeria strains with a primer derived from a pre-marker diagnostic fragment for *Listeria monocytogenes* selected from the group of nucleic acids corresponding to SEQ ID NOS:17, 18, and 19 to yield a 1300 bp diagnostic fragment for each of the positive and negative test panels;

(B) selecting at least one *Listeria monocytogenes* diagnostic marker contained within the diagnostic fragment by comparing the diagnostic fragment obtained from the amplification of the positive test panel with the diagnostic fragment obtained from the amplification of the negative test panel whereby at least one highly conserved region in the diagnostic fragment of the positive test panel is identified which is less than 90% homologous to any member of the negative test panel;

(C) designing at least one amplification primer corresponding to the at least one diagnostic marker identified in step (B); and (D) amplifying genomic DNA of the unknown bacterium under suitable annealing temperatures with the at least one amplification primer of step (C), whereby obtaining at least one amplification product indicates that the unknown bacterium is a *Listeria monocytogenes.*

The method preferably uses *Listeria monocytogenes* pre-marker diagnostic fragments selected from the group consisting of nucleic acids corresponding to SEQ ID NOS:20–23. The method preferably uses *Listeria monocytogenes* diagnostic fragments that are at least 83% homologous to SEQ ID NOS:24–31 and 33–40. The method preferably uses diagnostic fragments selected from the group consisting of nucleic acids corresponding to SEQ ID NOS:24–31 and 33–40. The method preferably uses at least one diagnostic marker selected in step (B) selected from the group consisting of nucleic acids corresponding to SEQ ID NOS:46–83.

Preferably, the amplification primers used are about 15 to 30 bp in length and suitable annealing temperatures are in the range of about 60° C.–70° C.

A method is also provided for determining whether an unknown bacterium is a member of the genus Listeria, comprising (A) amplifying genomic DNA from (i) a positive test panel of *Listeria monocytogenes* strains and (ii) a negative test panel of non-*monocytogenes* Listeria strains with a primer derived from a pre-marker diagnostic fragment for *Listeria monocytogenes* strains selected from the group consisting of nucleic acids corresponding to SEQ ID NOS:17,18 and 19 to yield a 1300 bp diagnostic fragment for each of the positive and negative test panels;

(B) selecting at least one Listeria genus-specific diagnostic marker contained within the diagnostic fragment by comparing the diagnostic fragment obtained from the amplification of the positive test panel with the diagnostic fragment obtained from the amplification of the negative test panel whereby at least one highly conserved region in the diagnostic fragment of the positive test panel is identified which is at least 90% homologous to the corresponding positive test panel of diagnostic fragment;

(C) designing amplification primers corresponding to the at least one Listeria genus-specific diagnostic marker selected in step (B); and (D) amplifying genomic DNA of the unknown bacterium under suitable annealing temperatures with the amplification primers of step (D), whereby obtaining amplification products indicates that the unknown bacterium is a member of the genus Listeria.

The genus-specific method at step (A) preferably uses a diagnostic fragment 83% homologous to any one of SEQ ID NOS:24–31 and 33–40. The method at step (A) preferably uses a diagnostic fragment selected from the group consisting of nucleic acids corresponding to SEQ ID NOS:24–31 and 33–40. The method preferably uses *Listeria monocytogenes* pre-marker diagnostic fragments selected from the group consisting of nucleic acids corresponding to SEQ ID NOS:20–23. The method preferably uses diagnostic markers selected in step (B) from the group consisting of nucleic acids corresponding to SEQ ID NOS:84–110. Preferably, the method uses amplification primers of about 15 to 30 bp in length and uses a suitable annealing temperature in the range of about 60° C. to 70° C.

A hybridization method for determining whether an unknown bacterium is a *Listeria monocytogenes* is provided comprising contacting the genomic DNA of the unknown bacterium with a nucleic acid probe selected from the group consisting of nucleic acid sequences corresponding to SEQ ID NOS:46–83, and then detecting hybridization of the nucleic acid probe with the genomic DNA. A genus-specific hybridization method for determining whether an unknown bacterium is a *Listeria monocytogenes* is provided comprising contacting the genomic DNA of the unknown bacterium with a nucleic acid probe selected from the group consisting of nucleic acid sequences corresponding to SEQ ID NOS:84–110, and then detecting hybridization of the nucleic acid probe with the genomic DNA.

Isolated nucleic acid fragments are provided selected from the group consisting of nucleic acid fragments corresponding to SEQ ID NOS:17 through 110. Isolated nucleic acid fragments are provided encoding the amino acid sequence as given in any one of SEQ ID NOS:32 and 41–45. This invention further provides isolated nucleic acid fragments having SEQ ID NOS:17–110

A further embodiment of the invention are nucleic acid fragments located on a diagnostic fragment of about 1300 bp and selected from the group consisting of nucleic acid fragments designated 1515(rc341×2)-26-363,
1515(rc341×2)-27-281,
1515-26-36,
1515-27-357,
1515-26-rc233,
1515(8585)-27-rc737,
1515(8585)-28-rc793
1515-30-76,
1515-30-88,
1515(8585)-30-624,
1515(8585)-30-rc483,
1515(8585)-30-rc555,
1515(8585)-30-rc573,
1515(8585)-30-rc824, the diagnostic fragment characterized by (A) at least 83% homology to any one of SEQ ID NOS:24–31 and 33–40; and (B) an open reading frame of about 855 bp contained within the diagnostic fragment, the open reading frame encoding an amino acid sequence of any one of SEQ ID NOS:32 and 41–45.

In greater detail, the methods involve the following steps:

(i) RAPD analysis: The genomic DNA of positive and negative test panels of a representative number of individuals for *Listeria monocytogenes* was amplified using RAPD primers. The positive test panel consisted of 20 strains of *Listeria monocytogenes* and the negative test panel consisted of 25 strains of non-*monocytogenes* Listeria spp. RAPD amplification gave some amplification products specific to the positive test panel that were not seen in the negative test panel.

The RAPD marker profiles from individuals of the positive test panel were compared with the RAPD marker profiles from individuals of the negative test panel and a nucleic acid fragment was selected where the fragment was present in all of the RAPD marker profiles from the positive test panel and absent in the RAPD marker profiles from the negative test panel. This fragment was termed a "pre-marker sequence".

(ii) Sequencing: The nucleotides of the pre-marker sequence of step (i) were sequenced to identify available primer binding sites.

(iii) Evaluation of the pre-marker sequence for *Listeria monocytogenes* specificity: Single primers derived from the pre-marker sequence were selected. These primers produced single amplification products when used to amplify genomic *Listeria monocytogenes* DNA.

(iv) Determination and isolation of the diagnostic fragment: Sequences of the flanking regions of the pre-marker sequence were determined revealing a diagnostic fragment of 1300 bp. Sequencing of the diagnostic fragment in *Listeria monocytogenes* and non-*monocytogenes* Listeria revealed conserved regions specific both to Listeria spp. in general and *Listeria monocytogenes* in particular. Amplification primers were designed based on these conserved regions.

(v) Preliminary selection of *Listeria monocytogenes* diagnostic primers on the basis of sensitivity to annealing temperature: Primers unique to *Listeria monocytogenes* were identified based on the diagnostic fragment. Primer pairs were selected on the basis of their ability to resist the formation of non-specific amplification products as annealing temperatures were reduced.

(vi) Final Selection of *Listeria monocytogenes* diagnostic primers: The primers of step (v) were used in the amplification of genomic DNA from a large group of *Listeria monocytogenes* (positive test panel) and non-*monocytogenes* species (negative test panel) under specific annealing conditions, confirming the specificity of these primers for *Listeria monocytogenes* detection.

(vii) Preliminary Selectivity Testing for Listeria spp. diagnostic primers: Primers unique to Listeria spp. were identified based on the diagnostic fragment. Primer pairs were selected on the basis of their ability to specifically detect L. spp.

(viii) Selection of Listeria spp. diagnostic primers on the basis of sensitivity to annealing temperature: The primer pairs of step (vii) were screened on the basis of their ability to resist the formation of non-specific amplification products as the annealing temperatures were reduced.

(xi) Final Selection of Listeria spp. diagnostic primers: The primers of step (viii) were used in the amplification of genomic DNA from a large group of Listeria spp. (positive test panel) and non-Listeria spp. (negative test panel) under specific annealing conditions, confirming the specificity of these primers for Listeria spp. detection.

BRIEF DESCRIPTION OF THE FIGURES

FIG. 2 shows a comparison of the amino acid sequences of *L. monocytogenes* #647, *L. innocua* DP #4450, *L. seeligeri* DP #3327, *L. welshimeri* DP #3359, and *L. ivanovii* DP #3340.

FIG. 3 shows the unique *Listeria monocytogenes* specific diagnostic primer sequences located at 1515(rc341x2)-26-363, 1515(rc341x2)-27-281, 1515-26-36, 1515-27-357, 1515-26-rc233, 1515(8585)-27-rc737, and 1515(8585)-28-rc793 and a comparison of priming site sequences for strains representing the following species: *L. monocytogenes, L. innocua, L. seeligeri, L. welshimeri* and *L. ivanovii*.

FIG. 6 is a gel showing the seven Listeria spp. specific primer sequences located at 1515-30-76, 1515-30-88, 1515(8585)-30-624, 1515(8585)-30-rc483, 1515(8585)-30-rc555, 1515(8585)-30-rc573, and 1515(8585)-30-rc824 and a comparison of priming site sequences for strains representing the following species: *L. monocytogenes, L. innocua, L. seeligeri, L. welshimeri* and *L. ivanovii*.

Figure 1:
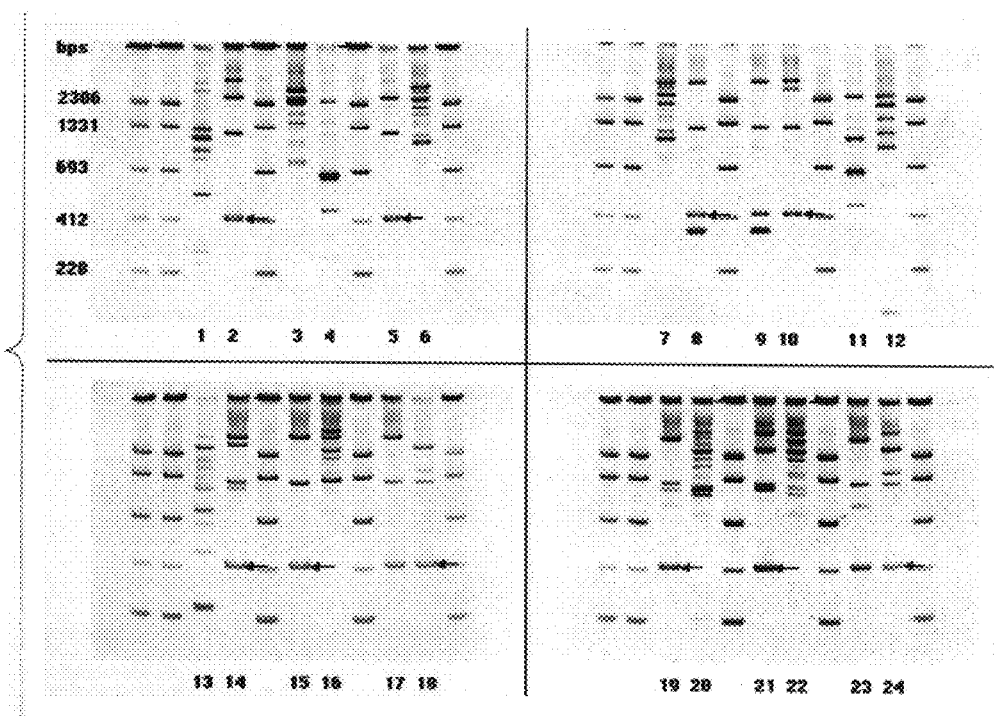
FIG. 1 is a gel showing RAPD patterns for *Listeria monocytogenes* strains comprising both the negative and positive test panels, amplified with the 12-mer primer 12CN015. The specific lanes are identified in Table 3.

Applicants have provided 110 sequence listings in conformity with 37 C.F.R. 1.821–1.825 and Appendices A and B ("Requirements for Application Disclosure Containing Nucleotides and/or Amino Acid Sequences") and in conformity with "Rules for the Standard Representation of Nucleotide and Amino Acid Sequences in Patent Applications" and Annexes I and II to the Decision of the President of the EPO, published in Supplement No. 2 to the OJ EPO, 12/1992.

Sequences of SEQ ID NOS:1–16 are twelve-base arbitrary primers used in the generation of RAPD patterns. These are also shown in Table 1. Sequences of SEQ ID NOS:17–19 are single primers derived from the pre-marker sequences. These are also shown at Table 2. SEQ ID NOS:20 and 21 represent the pre-marker sequence for strain #647 and SEQ ID NOS:22 and 23 represent the pre-marker sequence for strain #1324. The amino acid composition for all *L. monocytogenes* strains is represented in SEQ ID NO:32. Sequences corresponding to SEQ ID NOS:24–31 and 33–40 are diagnostic fragments; Sequences corresponding to SEQ ID NOS:32 and 41–45 are open reading frames encoding amino acid sequences.

DETAILED DESCRIPTION OF THE INVENTION

In the present method, Applicants have used RAPD amplification of *Listeria monocytogenes* and Listeria spp. genomic DNA to discover diagnostic fragments and primers useful for the specific detection of *Listeria monocytogenes* and Listeria spp. The fragments are used to generate specific primers from the most conserved regions for use in a PCR assay that will produce amplification products specific to either *Listeria monocytogenes* or Listeria spp.

Applicant's method is distinctive in the following regard. To selectively detect *Listeria monocytogenes* from all other Listeria or Listeria spp. from all other bacteria the method must be successful in determining the most conserved regions of the diagnostic fragments from a phenotypically uncharacterized segment of DNA common to all *Listeria monocytogenes* or all Listeria spp. One of skill in the art will recognize that conservation of sequence may be both an ally and an enemy in identifying the members of a particular genus. For example, many bacterial sequences are conserved across genera and these would not be useful in the determination of species within a particular genus. It is precisely for that reason that methods previously known in the art rely primarily on the analysis of sequences derived from proteins or genes known to be specific to a particular genus, i.e., ribosomal RNA or toxin-encoding genes. Applicant's method departs from the art in that the conserved sequences of the invention are not derived from a known gene nor is the sequence associated with any known phenotypic characteristic.

As used herein the following terms may be used for interpretation of the claims and specification.

"Nucleic acid" refers to a molecule which can be single-stranded or double-stranded, comprising monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The term "primer-directed amplification" refers to any of a number of methods known in the art that result in logarithmic amplification of nucleic acid molecules using the recognition of a specific nucleic acid sequence or sequences to initiate an amplification process. Applicants contemplate that amplification may be accomplished by any of several schemes known in this art, including but not limited to the polymerase chain reaction (PCR) or ligase chain reaction (LCR). If PCR methodology is selected, the amplification method would include a replication composition consisting of, for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis et al.) and U.S. Pat. No. 4,683,195 (1986, Mullis et al.).

The term "pre-marker sequence" refers to a 414 bp fragment of DNA that is an internal region of the diagnostic fragment.

The term "derived from", with reference to an amplification primer, refers to the fact that the sequence of the primer is a fragment of the sequence from which it has been "derived". The fragment is always denoted in a 5' to 3' orientation. The useful primer sequence size range for PCR amplification is about 15 base pairs to about 30 base pairs in length.

A "diagnostic fragment" refers to a particular DNA sequence which is highly conserved amongst the individuals of a particular genetically related population, for example, a genus, species, or serotype of bacteria. In the instant invention, the term "diagnostic fragment" is used to refer to the composite of that DNA fragment generated during RAPD amplification and those fragments that are generated from amplification with single primers derived from the pre-marker sequence, which are present in the RAPD and the single primer amplification profiles from either 1) all *Listeria monocytogenes* and absent from other Listeria spp. or 2) present in all Listeria spp. but absent in profiles from non-Listeria species. The term "diagnostic marker" is used herein to refer to that portion of the diagnostic fragment which can be targeted to produce an amplification product only in either *Listeria monocytogenes* or Listeria spp. The diagnostic marker is present only in the organism to be identified at the desired classification level (i.e., species or genus) and attempts to amplify the diagnostic markers in individuals not so targeted will give no amplification product. Within the context of the present invention diagnostic fragments which are diagnostic markers for *Listeria monocytogenes* and Listeria spp. and useful in Applicant's invention include nucleic acid sequences SEQ ID NOS:24–31 and 33–40 of about 1300 bp containing an open reading frame of 855 bp, encoding the peptide as given in SEQ ID NO:32.

The terms "conserved" or "highly conserved" refer to a level of similarity that exists between 2 or more nucleic acid fragments where there is at least 90% base similarity between the fragments. The term "base similarlity" refers to the relatedness between the nucelotide sequence of two nucleic acid molecules. Estimates of such similarity are provided by either DNA-DNA or DNA-RNA hybridization under conditions of stringency as is well understood by those skilled in the art (Sambrook et al., Molecular Cloning: A Laboratory Manual; volumes 1, 2, 3 (Cold Spring Harbor Laboratory, Cold Spring Harbor, N.Y.)).

The term "primer" refers to a nucleic acid fragment or sequence that is complementary to at least one section along a strand of the sample nucleic acid, wherein the purpose of the primer is to sponsor and direct nucleic acid replication of a portion of the sample nucleic acid along that strand.

Primers can be designed to be complementary to specific segments of a targeted sequence. In PCR, for example, each primer is used in combination with another primer forming a "primer set" or "primer pair"; this pair flanks the targeted sequence to be amplified. In RAPD amplification, single arbitrary primers are used to amplify nontargeted segments of nucleic acid which are located between the primer sequence sites in opposing DNA strands. The term "primer", as such, is used generally by Applicant to encompass any sequence-binding oligonucleotide which functions to initiate the nucleic acid replication process. "Diagnostic primers" will refer to primers designed with sequences complementary to primer binding sites on the diagnostic marker. Diagnostic primers are useful in the convenient detection and identification of diagnostic markers specific to *Listeria monocytogenes* and Listeria spp.

A "genetically related population" refers to any grouping of microorganisms possessing multiple or single genotypic or phenotypic characteristics of sufficient similarity to allow said organisms to be classified as a single genus, species, or subspecies of bacteria. For purposes of the present disclosure, examples of genetically related populations include, for example, *Listeria monocytogenes* and Listeria spp.

A "test panel" refers to a particular group of organisms or individuals selected on the basis of their genetic similarity to each other or on the basis of their genetic dissimilarity to another group (i.e., another genus, species, subspecies or serotype). A "positive test panel" will refer to a number of individuals selected for the desired genetic similarity between those individuals and, in the instant case, will be comprised of individuals of either *Listeria monocytogenes* or Listeria spp.

Similarly, a "negative test panel" will refer to a test panel selected on the basis of genetic diversity between its members and the members of the positive test panel. A suitable negative test panel in the present invention would be comprised of non-*Listeria monocytogenes* where *L. monocytogenes* is the target organism or non-Listeria spp. where Listeria spp. is the target organism.

The term "unknown microorganism" or "unknown bacterium" is a microorganism or bacterium whose identity is undetermined.

The term "amplification product" refers to specific DNA fragments generated from any primer-directed nucleic acid amplification reaction. The diagnostic markers of the present invention are amplification products generated in PCR reaction using diagnostic primers and are useful for the detection of *Listeria monocytogenes* and Listeria spp.

The term "RAPD" refers to "random amplified polymorphic DNA". "RAPD amplification" refers to a method of single primer-directed amplification of nucleic acids using short primers of arbitrary sequence to amplify nontargeted, random segments of nucleic acid. The method is disclosed and claimed in U.S. Pat. No. 5,126,239. "RAPD method" or "RAPD analysis" refers to a method for the detection of genetic polymorphisms involving the nontargeted amplification of nucleic acids using short primers of arbitrary sequence, whereby the profile or pattern of "RAPD" amplification products is compared between samples to detect polymorphisms. "RAPD primers" refers to primers of about 8 to 13 bp, of arbitrary sequence, useful in the RAPD amplification or RAPD analysis according to the instant method. The "RAPD marker profile" refers to the pattern, or fingerprint, of amplified DNA fragments which are amplified during the RAPD method and separated and visualized by gel electrophoresis.

The term "ribotype" refers to a specific classification of bacteria or other microorganisms based on the digestion of genomic DNA with a restriction endonuclease, electrophoretic resolution of the restricted DNA and visualization of those fragments containing rDNA sequences by means of hybridization with a probe derived from the rDNA operon.

The diagnostic marker of the invention can be used to identify any member of either *Listeria monocytogenes* to the exclusion of other Listeria spp., or Listeria spp. to the exclusion of all other bacteria. In the present invention, diagnostic primers flanking the marker are useful to amplify the marker using PCR. Alternatively, nucleic acid probes could be developed based upon some or all of the diagnostic marker sequences and thus used to detect the presence of the marker sequence using standard solid phase or solution nucleic acid hybridization and reporter methods. It is contemplated that regions of about 30 base pairs or more of the diagnostic marker, especially encompassing the primer regions could be used as sites for hybridization of diagnostic probes. These methods might be used specifically for the detection of *Listeria monocytogenes* or Listeria spp. in food, human or animal body fluids or tissues, environmental media or medical products and apparatti.

The instant method is more particularly described below with reference to the specific method steps as provided in the Summary of the Invention.

Selection of RAPD Primers and Detection of Diagnostic Fragment in Members of the Positive and Negative Test Panels, step (i)

Genomic DNA isolated from positive and negative test panels of microorganisms was subjected to RAPD amplification using sixteen 12-base primers of arbitrary sequence. The positive test panel consisted of 20 strains of *Listeria monocytogenes* and is described in detail in the GENERAL METHODS section below. The negative test panel consisted of a variety of 25 Listeria spp. and is also described in the GENERAL METHODS section below. Techniques for the isolation of genomic DNA are common and well known in the art and examples may be found in Sambrook et al., *Molecular Cloning: A Laboratory Manual-* volumes 1, 2, 3 (Cold Spring Harbor Laboratory Press, Cold Spring Harbor, N.Y. (1989)).

RAPD primers of 12 bases in length were used because at this primer length the RAPD patterns generally contained one to five amplified DNA fragments. Use of shorter primers frequently resulted in a large number of amplification products, which made the extraction of a single homogeneous fragment for sequencing much more difficult. When primers of greater than 12 bases were used a significant fraction of the bacterial strains produced no RAPD products which would have necessitated the screening of a much larger number of arbitrary primers. One of the primers, designated 12CN015 (Table I, GENERAL METHODS), was found to produce a 414 bp amplification product (termed a pre-marker sequence) in all of the positive test panel. 12CN015 had the sequence of GGA CAG AGC ATA (SEQ ID NO:15). The primer, 12CN15, was found to produce a 414 bp amplification product in all *L. monocytogenes* strains. This 414 bp pre-marker sequence was not observed in the amplification products of the negative test panel using the same primer. Examples of the 12CN15 RAPD patterns for strains of both test panels is shown in FIG. 1.

Sequencing of Pre-marker Sequence, step (ii)

Since the 414 bp product was unique to *L. monocytogenes*, samples of this product were isolated for two strains different of *L. monocytogenes*, DP #647 and DP #1324, and the respective products sequenced. The two strains represented a ribotype that was highly polymorphic (#1324) based on RAPD patterns and a ribotype that is pathogenic (#647). The object of selecting a common pathogenic strain and a polymorphic strain of *L. monocytogenes*, was to characterize the genetic diversity likely to be found within the 12CN15 marker fragment.

The complete sequences of the 414 bp products for DP #647 and #1324, including the flanking 12CN15 sequences, are shown in SEQ ID NOS:20 and 21 for DP #647 and SEQ ID NO:21 and 23 for DP #1324. Comparison of the DP #647 and #1324 sequences shows a 98% homology. Both sequences appear to be an internal section of an open reading frame (ORF) with the same amino acid composition.

Evaluation of Pre-marker Sequence for *Listeria monocytogenes* Specificity, step (iii)

The purpose of the initial PCR screening was to identify sequence domains that demonstrated species selectivity. Primers based on the 414 bp pre-marker sequences were first evaluated for their ability to specifically amplify from *L. monocytogenes* genomic DNA. Initial primer sequences were 26 bases long with a GC composition of 50±5% to allow for an annealing temperature in the range of 70° C. Priming sites were selected within a distance of 200 bases from each 12CN15 priming site. These sequences were examined to insure that inter- and intra-primer interactions were minimized to avoid the production of nonspecific PCR artifacts.

Many of the initial primer pairs that were tested generated multiple amplification products from genomic *L. monocytogenes* DNAs. Multiple PCR products can occur when at least 8 bases of one 3' primer sequence appears as an inverted repeat in the region adjacent to the originally targeted priming sites. To determine which products were the result of inverted repeats of a single primer sequence and which primers were responsible for these products, amplification reactions were run using single primers. A significant number of single primers such as 1515-26-85, (SEQ ID NO:17) 1515-26-rc292 (SEQ ID NO:18) and 1515-26-rc341 (SEQ ID NO:19) (Table 2) were capable of generating PCR products in single primer amplifications.

Determination and Isolation of the Diagnostic Fragment, step (iv)

Determination of sequences adjacent to the RAPD marker

Each of the single primers, 1515-26-85, (SEQ ID NO:17) 1515-26-rc292 (SEQ ID NO: 18) and 1515-26-rc341 (SEQ ID NO: 19) generated a PCR product that contained part of the original 414 bp fragment plus additional sequence. Sequence determination of these augmented CN15 fragments was accomplished by means well known in the art.

Sequencing revealed approximately 900 bases of additional sequence. The new sequence consisted of 400 bases in the region preceding the original 12CN15 site and 500 bases in the region following the second 12CN15 site revealing a complete open reading frame (ORF).

The degree of conservation within this genetic locus was further examined by amplification of additional *Listeria monocytogenes* strains and comparison of those amplification products with the strains already sequenced.

Comparison revealed that all strains contain a 1300 bp diagnostic fragment containing a complete open reading frame of 855 bases. This sequence was used as the diagnostic fragment and is identified by SEQ ID NOS:24–31. To determine if this fragment contained selective priming sites for *Listeria monocytogenes* specific primers, further analysis of the sequence composition was done to determine if it was distinct from other Listeria spp.

BASE SIMILARITY COMPARISON BETWEEN 1300 BP DIAGNOSTIC FRAGMENTS

A comparison of the base similarity between all isolated 1300 bp diagnostic fragments is given below.

| | #647 | #1324 | #4450 | #654 | #3327 | #3340 |
|---|---|---|---|---|---|---|
| *L. MONO* #647 | 97.1% | 86.8% | 84.5% | 83.3% | 83.0% | |
| *L. MONO* #1324 | | 86.6% | 84.4% | 83.6% | 82.7% | |
| *L. INN.* #4450 | | | 85.9% | 84.3% | 82.9% | |
| *L. WELSH.* #654 | | | 83.2% | 82.9% | | |
| *L. SEEL.* #3327 | | | | 86.1% | | |
| *L. IVAN.* #3340 | | | | | | |

Sequencing marker fragment for other Listeria species—determination of sequence composition of diagnostic fragment Evaluation of primer sites in the 1300 bp diagnostic fragment showed that not all primer sites were specific for *Listeria monocytogenes*, suggesting conservation of the sequence composition at the genus level.

The genetic composition was explored by isolating and sequencing the 855 bp fragment and the flanking regions from a panel of non-monocytogenes strains. All strains were found to contain the 855 base open-reading frame. However, a comparison of the sequences demonstrated there were species-dependent differences in the nucleic acid composition within the ORF SEQ ID NOS:33–40 and Table 3, Example 3). The specific locations of these differences suggest priming sites where the diversity of nucleotide sequence may be sufficient to allow for selective priming of *Listeria monocytogenes* strains.

Preliminary selection of *Listeria monoaytogenes* diagnostic primers on the basis of sensitivity to annealing temperature, step (v)

A comparison of sequence data for the five L. spp. made it possible to identify seven priming sites that were unique to *L. monocytogenes*. These priming sites were as follows; 1515(rc341×2)-26-363, 1515(rc341×2)-27-281, 1515-26-1515-27-357, 1515-26-rc233, 1515(8585)-27-rc737, and 1515(8585)-28-rc793 (FIG. 3) 26 to 30 bases in length depending on the GC composition. Longer primers were used for sites with a GC composition of<50% to assure that a 70° C. annealing temperature could be maintained. FIG. 7 shows the primer sequences and a comparison of priming site sequences for strains representing the following species: *L. monocytogenes, L. innocua, L. seeligeri, L. welshimeri* and *L. ivanovii*.

To minimize the likelihood that *L. monocytogenes* selective primers would generate PCR products from mismatched priming in non-*monocytogenes* strains, the relationship between annealing temperature and selectivity was evaluated. A test panel consisting of both *Listeria monocytogenes* and non-*monocytogenes* strains was prepared and amplifications were carried out over a range of temperatures and analyzed for the appearance of amplification products from Listeria spp. that were non-*monocytogenes*. Primer pairs that showed an onset of non-specific amplification at or above 65° C. were considered as unsuitable for use as *Listeria monocytogenes* diagnostic primers.

Final selection of *Listeria monocytogenes* diagnostic primers step (vi)

Before making the final primer selection, the accuracy of all candidate primer sets was evaluated for a larger group of *L. monocytogenes* strains. A set of 323 strains of *L. monocytogenes* was used to evaluate the inclusivity of the following primer sets: 1) 1515-27-357/1515(8585)-27-rc737; 2) 1515-27-357/1515(8585)-28-rc793; and 3) 1515(rc341×2)-26-(-363) /1515-26-rc233 (FIG. 3). Accuracy in detection of *Listeria monocytogenes* ranged from 99.5% to 100% depending on the primers and amplification conditions used. None of the three primer sets generated amplification products for the 30 non-*monocytogenes* strains in the annealing stringency test panel.

Preliminary selectivity testing of Listeria spp. diagnostic primers, step (vii)

A comparison of sequence data for the five above-mentioned Listeria species made it possible to identify seven priming sites present in strains representing these species that were at least 90% homologous to *L. monocytogenes*. These priming sites were as follows: 1515-30-76, -1515-30-88, 1515(8585)-30-624, 1515(8585)-30-rc483, 1515(8585)-30-rc555, 1515(8585)-30-rc573, and 1515(8585)-30-rc824 (FIG. 6). Primers to these sites were made 30 bases in length to compensate for mismatches in sequence and to assure that a 70° C. annealing temperature could be maintained.

Before evaluating stringency conditions, the accuracy of all candidate primer sets was evaluated for a group of 33 L. spp. strains. These strains were used to evaluate the inclusivity of the following primer sets:

1) 1515-30-76/1515(8585)-30-rc483;
2) 1515-30-76/1515(8585)-30-rc30-rc555;
3) 1515-30-76/1515(8585)-30-rc573;
4) 1515-30-76/1515(8585)-30-rc824;
5) 1515-30-88/1515(8585)-30-rc483;
6) 1515-30-88/1515(8585)-30-rc555;
7) 1515-30-88/1515(8585)-30-rc573; 8) 1515(8585)-30-624/1515(8585)-30-rc824.

The accuracy in the detection of L. spp. was 100% for the following primer sets: 1515-30-76/1515(8585)-30-rc555;1515-30-76/1515(8585)-30-rc573; 1515-30-88/1515(8585)-30-rc555; and 1515-30-88/1515(8585)-30-rc573.

Selection of Listeria spp. diagnostic primers on the basis of sensitivity to annealing temperature. step (viii)

As with *Listeria monocytogenes*, the relationship between annealing temperature and selectivity was evaluated to minimize the generation of non-specific amplification products. This test was performed for all the primer pairs that scored 100% in the preliminary inclusivity evaluation. Amplifications were carried out on a test panel of 7 strains of Listeria spp. and non-L. spp. at an annealing temperature of 70° C. Annealing temperature was then decreased in 5° C. increments until the onset of nonspecific amplification products. The 1515-30-76/1515(8585)-30-rc555 primer set was found to be the least likely to generate nonspecific amplification products.

Final selection of Listeria sp. diagnostic primers step (ix)

Before confirming the selection of the 1515-30-76/1515(8585)-30-rc555 primer set, the accuracy of this primer set was evaluated for a group of 73 L. spp. strains. Accuracy in detection of *L. monocytogenes, L. innocua, L. welshimeri, L. seeligeri*, and *L. ivanovii* was 100%. This primer set did not generate amplification products for the 65 non-Listeria spp. strains in the non-Listeria test panel.

To determine whether the selected primer set would generate PCR products from mismatched priming in non-*monocytogenes* strains, the relationship between annealing temperature and selectivity was evaluated. A test panel consisting of both Listeria spp. and non-L. spp. strains was prepared and amplifications were carried out over a range of temperatures and analyzed for the appearance of amplification products from non-L. spp. In this fashion, it was determined that 60° C. is the lowest annealing temperature that will result in specificity for L. spp., and 70° C. is the preferred temperature that should be used when using this set of Listeria spp. specific primers.

RAPD Primers

RAPD primers used for amplification of genomic DNA from the positive and negative test panels are given below in Table 1.

TABLE 1

Twelve-Base Arbitrary Primers Used in the Generation of RAPD Patterns

| | | | | | |
|---|---|---|---|---|---|
| 12CN01- | AGC TGA TGC TAC | SEQ ID NO: 1 | 12CN09- | AAC CTC GTG TAG | SEQ ID NO: 9 |
| 12CN02- | AGT CGA ACT GTC | SEQ ID NO: 2 | 12CN10- | CAT TCG GGT ACA | SEQ ID NO: 10 |
| 12CN03- | TTA GTC ACG GCA | SEQ ID NO: 3 | 12CN11- | GCC CTT AGT GAA | SEQ ID NO: 11 |
| 12CN04- | TGC GAT ACC GTA | SEQ ID NO: 4 | 12CN12- | GCA GTT ATG ACC | SEQ ID NO: 12 |
| 12CN05- | CTA CAG CTG ATG | SEQ ID NO: 5 | 12CN13- | CCA GCT ATC TCT | SEQ ID NO: 13 |
| 12CN06- | GTC AGT CGA ACT | SEQ ID NO: 6 | 12CN14- | AGA AGG CAG TTG | SEQ ID NO: 14 |
| 12CN07- | GGC ATT AGT CAC | SEQ ID NO: 7 | 12CN15- | GGA CAG AGC ATA | SEQ ID NO: 15 |
| 12CN08- | CGT ATG CGA TAC | SEQ ID NO: 8 | 12CN16- | CGT TTC GCT TCA | SEQ ID NO: 16 |

EXAMPLES

General Methods

Procedures for DNA amplifications and other protocols common in the art of molecular biology used in the following examples may be found in Sambrook, J. et al., *Molecular Cloning: A Laboratory Manual*, Second Edition, Cold Spring Harbor Laboratory Press, Cold Spring Harbor, N.Y. (1989).

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or in the work of Thomas D. Brock (in *Biotechnology: A Textbook of Industrial Microbiology*, Second Edition (1989) Sinauer Associates, Inc., Sunderland, Mass.). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

DNA sequencing was performed by Lark Sequencing Technologies Inc., (Houston, Tex.) or according to the method of Sanger et al. (*Proc. Natl. Acad. Sci., USA* 74, 5463, (1977)) using fluorescence-labeled dideoxynucleotides and the Genesis 2000™ DNA Analysis System (E.I. du Pont de Nemours and Company, Wilmington, Del.).

Construction of Positive and Negative Test Panels *Listeria monogytogenes*

A positive test panel consisting of 20 genotypically different *Listeria monocytogenes* strains was constructed for the identification of a *Listeria monocytogenes* and Listeria spp. RAPD marker. The *Listeria monocytogenes* strains of the postive test panel encompassed all commonly encountered serotypes and included *L. monocytogenes*, DP #647, #899, #1324 and #3386.

The negative test panel consisted of 25 different Listeria non- mono-cytogenes strains comprising the species *L. innocua, L. seeligeri, L. welshimeri, L. grayi, L. murrayi* and *L. ivanovii*.

Primer Nomenclature

Primers names identified in the following examples are derived in the following manner: The first number, 1515, indicates the primer sequence comes from the RAPD fragment primed at both ends by 12CN15. The second number indicates the primer length. The third number identifies the 3' base position of the primer, where position 1 is at the 5' end of the original putative 12CN15 priming site. The rc designation means that the priming site is located on the complementary strand.

Primer locations may also be referred to by the last number of the identifying number. Thus "1515-26-85" may be referred to as "85".

RAPD primers may be referred to with out the "12" designation. Thus "12CN15" may also be referred to as "CN15".

The primers described below in Table 2 are derived from the pre-marker sequence. As single primers they match the pre-marker sequence and they also match at least the last 9 bases of 3' sequence at another location outside of the pre-marker sequence. The net effect is that these primers will generate amplification products in single primer reactions from genomic DNA. These products contain part of the original 414 bp fragment plus additional sequence.

TABLE 2

| SPECIFICITY | I. D. | SEQUENCE | SEQ ID NO |
|---|---|---|---|
| Pre-marker | 1515-26-85 | TGC TGT TTG GTT TGC TCT AGC CCA GTG | SEQ ID NO: 17 |
| | 1515-26-rc292 | CAA CTT TCC ACA TGG CGC GAT TAT TTG | SEQ ID NO: 18 |
| | 1515-26-rc341 | GGG GAA CTG CCG AAG ATC GTA CAG CA | SEQ ID NO: 19 |

Example 1

Isolation Of Pre-Marker Sequence From *Listeria Monocytogenes* By RAPD Analysis

Example 1 details the isolation of the 414 bp pre-marker sequence from *Listeria monocytogenes* genomic DNA using Random Amplified Polymorphic DNA RAPD primer analysis.

A set of eight 12-base primers (Table I) was used in a RAPD analysis of 20 strains of *Listeria monocytogenes*. The results of these amplifications were examined for a *Listeria*

*monocytogenes*-specific amplification product that could be easily separated from other RAPD products.

The amplification and data acquisition protocol for each 12-base primer RAPD reaction was as follows:

Amplification protocol: For each 50 μL reaction, 1.5 μL—dNTP mix (5 mM dNTP each), 36.3 μL—deionized water, 5 μL–10× reaction buffer (500 mM KCl, 100 mM tris @ pH 8.3, 15 mM MgCl$_2$, 0.003% gelatin), 5 μL—primer (10 mM), 0.4 μL—Taq polymerase (5 U/μL), and 1.2 μL—Taq dilution buffer (10 mM tris @ pH 8.0 and 1.0% Tween 20) were combined. A 1.0 μL aliquot of genomic bacterial DNA @ 50 ng/μL was added to each mixture. The reaction was heated to 94° C. for 2 min. Twenty-eight cycles of the following temperature profile were run: 15" @ 94° C., 5' @ 46° C., 2' ramp to 72° C. and 1' @ 72° C. At the end of cycling the reaction was incubated at 72° C. for 7 min.

After amplification a 5 μL aliquot of the reaction was combined with 2 μL of Ficol-loading buffer and run on a 4% acrylamide gel (29:1)/1.0× TBE. Follow-ing electrophoresis, the gels were stained with ethidium bromide. The stained gels were placed on a transilluminator and electronically imaged with a high sensitivity CCD camera. Images were stored in computer memory for subsequent analysis. Analysis: The primer, 12CN15, (SEQ ID NO:15) was found to produce a 414 bp amplification product in all *L. monocytogenes* strains. This 414 bp fragment was not observed in the amplification products of the negative test panel using the same primer. Examples of the 12CN15 RAPD patterns for strains of both test panels is shown in FIG. 1. The lanes are correlated to FIG. 1 as follows in Table 3:

TABLE 3

| Lane | Strain | Lane | Strain |
|---|---|---|---|
| 1 | L. welshimeri #943 | 13 | L. ivanovii #1165 |
| 2 | L. monocytogenes #945 | 14 | L. monocytogenes #1281 |
| 3 | L. seeligeri #949 | 15 | L. monocytogenes #1287 |
| 4 | L. innocua #950 | 16 | L. seeligeri #1290 |
| 5 | L. monocytogenes #1047 | 17 | L. monocytogenes #1283 |
| 6 | L. seeligeri #1059 | 18 | L. monocytogenes #1295 |
| 7 | L. seeligeri #1061 | 19 | L. monocytogenes #1299 |
| 8 | L. monocytogenes #1068 | 20 | L. seeligeri #1303 |
| 9 | L. monocytogenes #1069 | 21 | L. monocytogenes #1313 |
| 10 | L. monocytogenes #1070 | 22 | L. seeligeri #1317 |
| 11 | L. innocua #1089 | 23 | L. monocytogenes #1324 |
| 12 | L. innocua #1157 | 24 | L. monocytogenes #1963 |

*Arrows denote 414 bp product in *L. monocytogenes* strains. (See Lanes 2, 5, 8, 10, 14, 15, 18, 19, 21 and 24 of FIG. 1.)

As is evident from FIG. 1, the positive test panel produced a characteristic amplification product of 414 bp which appeared in all of the 20 *Listeria monocytogenes* strains tested. Additionally it is seen that none of the negative test panel group showed the 414 bp amplification product seen in the positive test panel.

Example 2

Generation of the Diagnostic Fragment From Sequence Flanking the Pre-Marker Sequence Example 2 illustrates the sequencing of the flanking regions of the 414 bp pre-marker sequence using single primers and the generation of the diagnostic fragment.

The 414 bp pre-marker sequence of Example 1 was commercially sequenced from two strains of *Listeria monocytogenes* (#647 and #1324) described above. The pre-marker sequence for each strain is given in SEQ ID NOS:20 and 21 for #647 and SEQ ID NOS:22 and 23 for #1324.

Primers were designed based on the pre-marker sequence, and evaluated for their ability to specifically amplify from *Listeria monocytogenes* genomic DNA. Initial primer sequences were 26 bases long with a GC composition of 50±5% to allow for an annealing temperature in the range of 70° C. Priming sites were selected within a distance of 200 bases from each 12CN15 priming site. Following this method three single primers were identified as 1515-26-85 (SEQ ID NO:17), 1515-26-rc292 85 (SEQ ID NO:18), and 1515-26-rc341 85 (SEQ ID NO:19), (Table 2) which generated a PCR product in the absence of a second primer.

Each of these single primers generated a PCR product that contained part of the original pre-marker sequence plus additional sequence. Sequence of these augmented 12CN15 fragments was accomplished using the chain-termination method of Sanger et al. (*Proc. Natl. Acad. Sci., USA* 74, 5463, (1977)) using fluorescence-labeled dideoxynucleotides and the Genesis 2000™ DNA Analysis System (E.I. du Pont de Nemours and Company, Wilmington, Del.).

The new sequence consisted of 400 bases in the region preceding the original 12CN15 site and 500 bases in the region following the second 12CN15 site. This sequence data made it possible to identify a complete ORF plus several hundred bases upstream and downstream from the reading frame.

To further characterize the degree of conservation within this genetic locus, nucleic acid sequences were determined for two additional strains of *L. monocytogenes*, DP #899 and DP #3386. DP #899 is an additional representative of a known pathogenic *L. monocytogenes* ribotype group. DP #3386 is a strain of a less pathogenic *L. monocytogenes* ribotype group. Sequencing of these strains was accomplished using the chain-termination method of Sanger et al,, (supra) and the Genesis 2000™ DNA Analysis System. The complete sequences for the *L. monocytogenes* strains, DP #647, #899, #1324 and #3386, are shown in SEQ ID NOS:24–31. (The 5' end of the original CN15 priming site was designated as base number 1 to provide a common reference point for all of the sequence data.)

Analysis of the nucleic acid sequence showed that all four strains contained a complete open reading frame of 855 bases. Within this ORF DP #647, #899, and #3386 all showed identical nucleic acid sequences. DP #1324 is 97% homologous with the other three *L. monocytogenes* strains. When the nucleic acid sequences were translated into the corresponding amino acid sequence DP #1324 was found to be identical to the other three strains. The amino acid composition for all of the *L. monocytogenes* strains is shown in SEQ ID NO:32).

The promoter and the terminal spacer sequences for DP #647, #899, and #3386 were also identical. DP #1324 shows an homology of 98% and 96% with the promoter and the terminal spacer, respectively. This genetic locus and the surrounding region showed a high level of conservation among strains of *L. monocytogenes*.

Further analysis of the sequence composition of the 1300 bp diagnostic fragment containing the 855 bp ORF was needed to determine if it was sufficiently distinct from other L. spp so as to provide selective priming sites for a PCR-based assay for *L. monocytogenes*.

Example 3

Determination of Sequence Composition of Diagnostic Fragment By Comparison of Marker Fragment Sequence With Other Listeria Species A preliminary evaluation of primer sites in the augmented CN15 marker demonstrated that many locations did not discriminate between *L. monocytogenes* and other L. spp.

This observation suggested that much of the sequence composition of this genetic locus was conserved at the genus level. To determine whether this genetic locus contained any sequences that were unique to L. monocytogenes, strains representing L. innocua, L. seeligeri, L. welshimeri and L. ivanovii were also selected for sequencing. (Marker sequences were not determined for L. grayi and L. murrayi because these species were considerably more polymorphic than other L. spp.) Previously determined non-selective priming sites were used to generate quantities of DNA suitable for sequencing. As with L. monocytogenes, primers 1515-26-85, (SEQ ID NO: 17), 1515-26-rc292 (SEQ ID NO:18), and 1515-26-rc341 (SEQ ID NO:19), used in single primer amplifications also generated PCR products suitable for sequencing. Sequencing was accomplished using the chain-termination method of Sanger et al., and the Genesis 2000™ DNA Analysis System.

A comparison of the nucleotide sequences showed that each of the above species contained an 855 base open-reading frame. However, there were some species dependent differences in the nucleic acid composition within the ORF. Sequences SEQ ID NOS:33–40 show the nucleic acid composition for the following strains: *L. innocua* DP #4450, *L. seeligeri DP* #3327, *L. welshimeri* DP #3359, and *L. ivanovii* DP #3340, respectively. These differences in nucleotide sequence are responsible for corresponding species variations in amino acid sequence. The nucleotide and amino acid sequence homology is summarized in Table 4. FIG. 2 shows a comparison of the amino acid sequences of each L. spp., including *L. monocytogenes*.

TABLE 4

Open Reading Frame Nucleotide and Amino Acid Sequence Comparison between Listeria Species

| Species | Nucleotide Homology to *L. monocytogenes* #647 | Amino Acid Homology to *L. monocytogenes* #647 |
|---|---|---|
| *L. innocua* | 86.7% | 95.8% |
| *L. seeligeri* | 84.5% | 94.0% |
| *L. welshimeri* | 83.8% | 93.7% |
| *L. ivanovii* | 83.3% | 93.3% |

Of the L. spp. that were tested, *L. innocua* clearly showed the greatest similarity to *L. monocytogenes*. The remaining three species all showed roughly comparable levels of divergence in nucleotide and amino acid composition.

The promoter and terminal spacer nucleic acid sequences also showed significant differences between species. The homologies of promoter and spacer sequences compared to *L. monocytogenes* are summarized in Table 5.

TABLE 5

Promoter and Terminal Spacer Sequence Comparison between *L. Spp.*

| Species | Promoter Homology to *L. monocytogenes* #647 | Terminal Spacer Homology to *L. monocytogenes* #647 |
|---|---|---|
| *L. innocua* | 91.9% | 79.4% |
| *L. seeligeri* | 85.0% | 75.4% |
| *L. welshimeri* | 90.9% | 75.5% |
| *L. ivanovii* | 83 7% | 84.0% |

The homology to *L. monocytogenes* found in promoter and terminal spacer sequences is significantly different from that observed for the open reading frame sequences. *L. innocua* and *L. welshimeri* both show homologies to *L. monocytogenes* in the promoter region that are significantly greater than the corresponding ORF homology. For *L. seeligeri* and *L. ivanovii* the promoter regions and ORF regions both show comparable levels of homology with *L. monocytogenes*. In three species the terminal spacer sequences show a notable decrease in homology compared to the promoter regions and open reading frames, while in *L. ivanovii* similar levels of homology to *L. monocytogenes* are found in all three regions.

Example 4

Selection of *Listeria Monocytogenes* Diagnostic Primers on the Basis of Sensitivity to Annealing Temperature Identification of Priming sites and Primer synthesis A comparison of sequence data for the five L. spp. (Example 3) made it possible to identify seven priming sites that were unique to *L. monocytogenes* These priming sites were as follows: 1515(rc341×2)-26-363, 1515(rc341×2)-27-281, 1515-26-36, 1515-27-357, 1515-26-rc233, 1515 (8585)-27-rc737, and 1515(8585)-28-rc793 (FIG. 3). "Uniqueness" is defined as any sequence region of 26–30 bases where the homology between *L. monocytogenes* and any other Listeria spp. is less than 90%.

Primers were synthesized to correspond to these sites and ranged in length from 26 to 30 bases depending on the GC composition. Longer primers were used for sites with a GC composition of<50% to assure that a 70° C. annealing temperature could be maintained.

FIG. 3 shows the primer sequences and a comparison of priming site sequences for strains representing the following species: *L. monocytogenes, L. innocua, L. seeligeri, L. welshimeri* and *L. ivanovii.*

Determination of annealing termperature

To minimize the likelihood that *L. monocytogenes*-selective primers would generate PCR products from mismatched priming in non-*monocytogenes* strains, the relationship between annealing temperature and selectivity was evaluated. A 33-strain test panel consisting of 15 *L. innocua,* 5 *L. welshimeri,* 6 *L. seeligeri,* 3 *L. ivanovii,* 1 *L. grayi* and 3 *L. monocytogenes* was prepared. Amplifications were first carried out at an annealing temperature of 70° C. Annealing temperature was then decreased in 5° C. increments until amplification products began to appear for the non-*monocytogenes* strains. The amplification and detection protocol is summarized below.

Combine 1.5 μL—dNTP mix (5 mM each dNTP), 40 μL - deionized water, 5 μL—10× reaction buffer (500 mM KCl, 100 mM tris@ pH 8.3, 15 mM $MgCl_2$, 0.003% gelatin) 0.4 μL—Taq polymerase (5 U/μL), 1.2 μL—Taq dilution buffer (10 mM tris@ pH 8.0 and 1.0% Tween 20), 0.66 μL—each primer (10 μM), and 1.0 μL—genoric DNA@ 50 ng/μL. Heat to 94° C. for 2 min. Thirty-five cycles of the following temperature profile were run: 15"@ ( 94° C.; 2' at the specified annealing temperature and 1' @ 72° C. At the conclusion of cycling the reaction was incubated at 72° C. for 7 min.

Visualization of amplification products is the same as described above.

Table 6 shows a comparison of the onset of false positive responses as the annealing temperature is reduced.

TABLE 6

Percent False Positive *L. monocytogenes* Responses as a Function of Annealing Temperature

| Primer Sets | Annealing Temperature, ° C. | | | |
|---|---|---|---|---|
| | 70° | 65° | 60° | 55° |
| 1515-27-357/ 1515(85,85)-27-rc737 | 0% | 0% | 5% | ND |
| 1515-27-357/ 1515(85,85)-28-rc793 | 0% | 0% | 55% | ND |
| 1515-26-36/ 1515-26-rc233 | 0% | 5% | 27% | ND |
| 1515(rc341,rc341)-27-(-281)/ 1515-26-rc233 | 0% | 0% | 0% | 1.5% |
| 1515(rc341,rc341)-26-(-363)/ 1515-26-rc233 | 0% | 0% | 0% | 33% |

*Primer label numbers contained in parentheses, i.e., (85,85) and (rc341, rc341), indicate that these primers were derived from fragments generated by the single primers, 1515-26-85 and 1515-26-rc341.

Primer pairs that produced no false positives at 5° C. below the standard annealing temperature of 70° C. were considered as candidates for a PCR-based *L. monocytogenes* assay. Of all the primer sets tested, only 1515-26-36/1515-26-rc233 showed an unacceptable onset of false positive responses at 65° C.

Figure 4A:
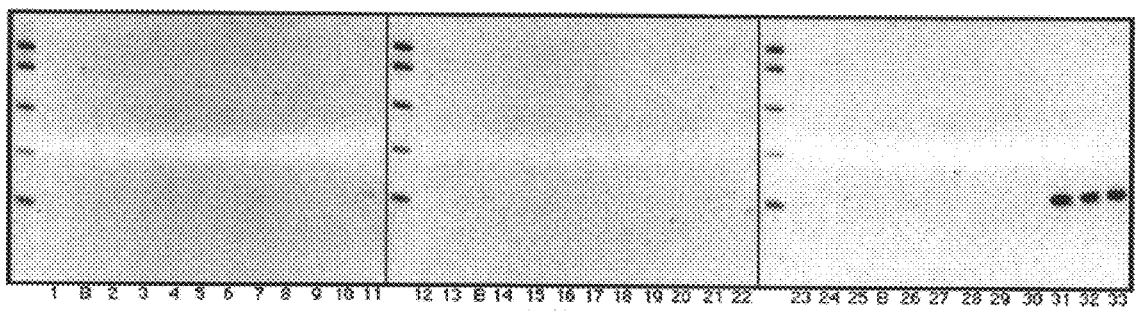
FIGS. 4A–4C are gels illustrating the appearance of anomalous and false positive amplification products as the annealing temperature was reduced for the 1515-26-36/1515-26-rc233 primer pair. The specific lanes are identified in Table 7.
Figure 4B:
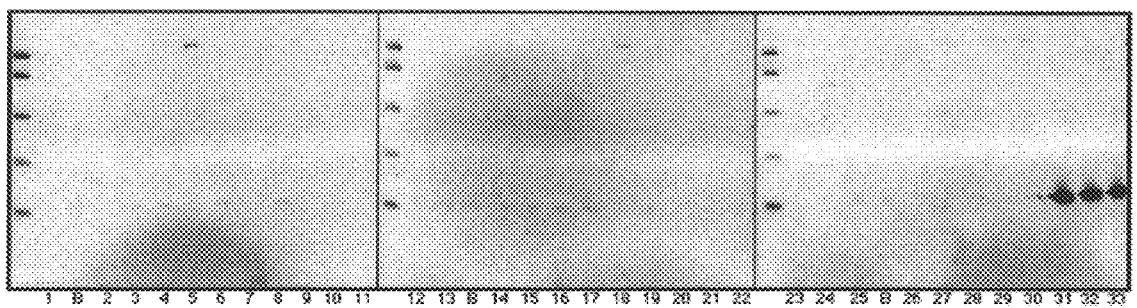
Figure 4C:
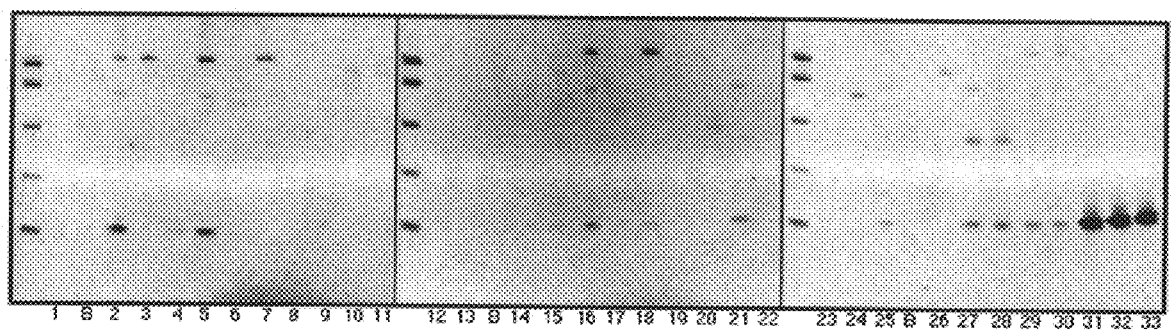

FIGS. 4A–4C are gels illustrating the appearance of anomalous amplification products as the annealing temperature was reduced for the 1515-26-36/1515-26-rc233 primer pair. The gel lanes are identified as follows in Table 7:

TABLE 7

| Lane | Strain |
|---|---|
| 1 | *L. seeligeri* #2874 |
| B | BLANK |
| 2 | *L. innocua* #2921 |
| 3 | *L. ivanovii* #3072 |
| 4 | *L. innocua* #3241 |
| 5 | *L. innocua* #3244 |
| 6 | *L. seeligeri* #3327 |
| 7 | *L. ivanovii* #3340 |
| 8 | *L. innocua* #3352 |
| 9 | *L. welshimeri* #3354 |
| 10 | *L. grayi* #3356 |
| 11 | *L. welshimeri* #3359 |
| 12 | *L. seeligeri* #3371 |
| 13 | *L. seeligeri* #3374 |
| B | BLANK |
| 14 | *L. welshimeri* #3411 |
| 15 | *L. welshimeri* #3412 |
| 16 | *L. innocua* #3420 |
| 17 | *L. innocua* #3429 |
| 18 | *L. ivanovii* #3357 |
| 19 | *L. welshimeri* #3558 |
| 20 | *L. innocua* #3571 |
| 21 | *L. innocua* #3797 |
| 22 | *L. seeligeri* #3828 |
| 23 | *L. innocua* #4094 |
| 24 | *L. innocua* #4101 |
| 25 | *L. innocua* #4323 |
| B | BLANK |
| 26 | *L. seeligeri* #4333 |
| 27 | *L. innocua* #4442 |
| 28 | *L. innocua* #4450 |
| 29 | *L. innocua* #4452 |
| 30 | *L. innocua* #4463 |
| 31 | *L. monocytogenes* #3847 |
| 32 | *L. monocytogenes* #4324 |
| 33 | *L. monocytogenes* #4341 |

EXAMPLE 5

Final Evaluation Of Listeria Monocytogenes Diagnostic Primers

Example 5 illustrates the inclusiveness of the identified *Listeria monocytogenes* diagnostic primers for all strains of *Listeria monocytogenes*.

The accuracy of all candidate primer sets was evaluated for a larger group of *L. monocytogenes* strains. A set of 323 strains of *L. monocytogenes* was used to evaluate the inclusivity of a set of three primer sets. PCR assay conditions were the same as those specified above except that only a 70° C. annealing temperature was used. In PCR-based assays using these three primer sets, the accuracy was as follows:

1) 1515-27-357/1515(8585)-27-rc737, 100%;
2) 1515-27-357/1515(8585)-28-rc793, 99.2%; and
3) 1515(rc341x2)-26-363/1515-26-rc233, 99.5%.

Figure 5A:
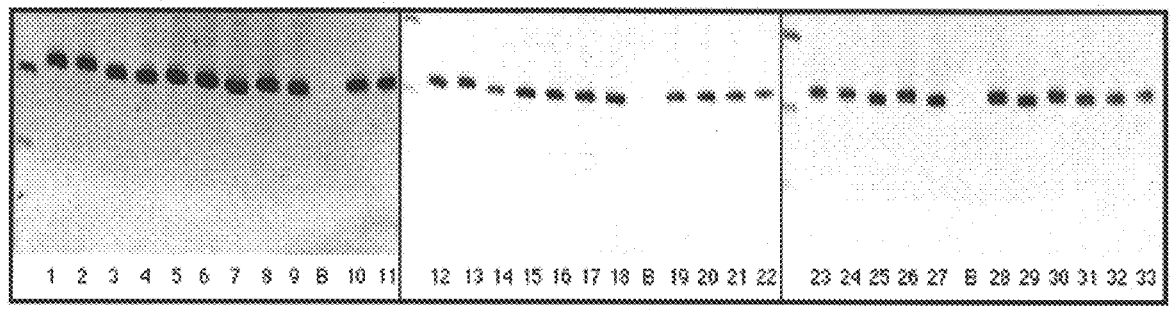
FIG. 5A displays the PCR product patterns of *Listeria monocytogenes* strains from the positive test panel amplified with the primer pair 1515-27-357/1515(8585)-27-rc737. The specific lanes are identified in Table 8, column A.
Figure 5B:
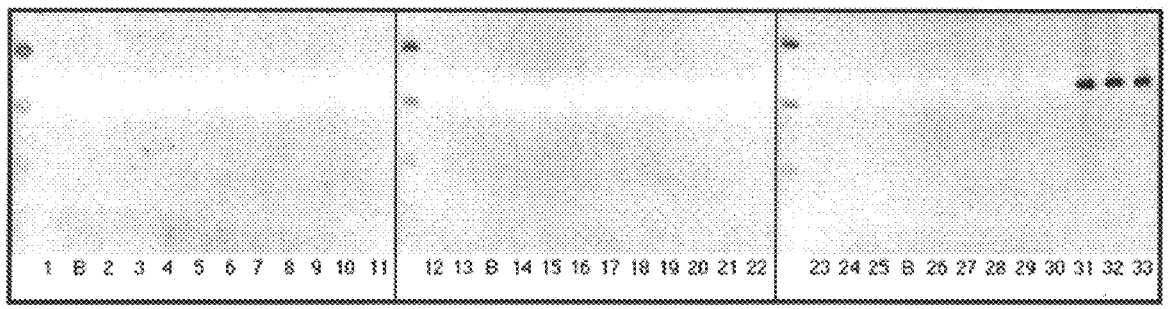
FIG. 5B displays the PCR product patterns of *Listeria monocytogenes* strains from the negative test panel amplified with the primer pair 1515-27-357/1515(8585)-27-rc737. The specific lanes are identified in Table 8, column B.

Although primer -281/rc233 was not tested, its inclusivity response was expected to be comparable to 1515(rc341x2)-26-363/1515-26-rc233. None of the three primer sets generated amplification products for the 30 non-*monocytogenes* strains in the annealing stringency test panel. Examples of the positive and negative test panel results for the 1515-27-357/1515(8585)-27-rc737 primer pair are shown in FIGS. 5A and 5B respectively. FIGS. 5A and 5B each show a gel analysis which corresponds to the strains listed in Table 8.

TABLE 8

| A Positive test panel response for PCR products generated from primer set 1515-27-357/ 1515(8585)-27-rc737 | | B Negative test panel response for PCR products generated from primer set 1515-27-357/ 1515(8585)-27-rc737 | |
|---|---|---|---|
| Lane | Strain | Lane | Strain |
| 1 | *L. monocytogenes* #652 | 1 | *L. seeligeri* #2874 |
| 2 | *L. monocytogenes* #1049 | B | BLANK |
| 3 | *L. monocytogenes* #936 | 2 | *L. innocua* #2921 |
| 4 | *L. monocytogenes* #954 | 3 | *L. ivanovii* #3072 |
| 5 | *L. monocytogenes* #957 | 4 | *L. innocua* #3241 |
| 6 | *L. monocytogenes* #952 | 5 | *L. innocua* #3244 |
| 7 | *L. monocytogenes* #946 | 6 | *L. seeligeri* #3327 |
| 8 | *L. monocytogenes* #955 | 7 | *L. ivanovii* #3340 |
| 9 | *L. monocytogenes* #937 | 8 | *L. innocua* #3352 |
| B | BLANK | 9 | *L. welshimeri* #3354 |
| 10 | *L. monocytogenes* #1051 | 10 | *L. grayi* #3356 |
| 11 | *L. monocytogenes* #1046 | 11 | *L. welshimeri* #3359 |
| 12 | *L. monocytogenes* #1067 | 12 | *L. seeligeri* #3371 |
| 13 | *L. monocytogenes* #1055 | 13 | L. seeligeri #3374 |
| 14 | *L. monocytogenes* #1057 | B | BLANK |
| 15 | *L. monocytogenes* #1087 | 14 | *L. welshimeri* #3411 |
| 16 | *L. monocytogenes* #1145 | 15 | *L. welshimeri* #3412 |
| 17 | *L. monocytogenes* #1146 | 16 | *L. innocua* #3420 |
| 18 | *L. monocytogenes* #1153 | 17 | *L. innocua* #3429 |
| B | BLANK | 18 | *L. ivanovii* #3357 |
| 19 | *L. monocytogenes* #1144 | 19 | *L. welshimeri* #3558 |
| 20 | *L. monocytogenes* #1322 | 20 | *L. innocua* #3571 |
| 21 | *L. monocytogenes* #1287 | 21 | *L. innocua* #3797 |
| 22 | *L. monocytogenes* #1316 | 22 | *L. seeligeri* #3828 |
| 23 | *L. monocytogenes* #1306 | 23 | *L. innocua* #4094 |
| 24 | *L. monocytogenes* #1298 | 24 | *L. innocua* #4101 |
| 25 | *L. monocytogenes* #1302 | 25 | *L. innocua* #4323 |
| 26 | *L. monocytogenes* #1285 | B | BLANK |
| 27 | *L. monocytogenes* #1286 | 26 | *L. seeligeri* #4333 |
| B | BLANK | 27 | *L. innocua* #4442 |
| 28 | *L. monocytogenes* #1294 | 28 | *L. innocua* #4450 |
| 29 | *L. monocytogenes* #1283 | 29 | *L. innocua* #4452 |
| 30 | *L. monocytogenes* #1288 | 30 | *L. innocua* #4463 |
| 31 | *L. monocytogenes* #1284 | 31 | *L. monocytogenes* #3847 |

TABLE 8-continued

| A Positive test panel response for PCR products generated from primer set 1515-27-357/ 1515(8585)-27-rc737 | | B Negative test panel response for PCR products generated from primer set 1515-27-357/ 1515(8585)-27-rc737 | |
| --- | --- | --- | --- |
| Lane | Strain | Lane | Strain |
| 32 | L. monocytogenes #1282 | 32 | L. monocytogenes #4324 |
| 33 | L. monocytogenes #1464 | 33 | L. monocytogenes #4341 |

EXAMPLE 6

Selectivity Testing For Listeria SPP. Diagnostic Primers

Selection of Listeria spp. Diagnostic Primers

A comparison of sequence data for the five Listeria species made it possible to identify priming sites that were at least 90% homologous to L. monocytogenes. The following priming sites were selected as possible candidates: 76, 88, 624, rc483, rc555, rc573, and rc324. Primers to these sites were made 30 bases in length to compensate for mismatches in sequence and to assure that a 70° C. annealing temperature could be maintained. FIG. 6 shows the primer sequences and a comparison of priming site sequences for strains representing the following species: L. monocytogenes, L. innocua, L. seeligeri, L. welshimeri and L. ivanovii. Primer pairs from this group were first evaluated with a 33-strain test panel consisting of 15 L. innocua, 5 L. welshimeri, 6 L. seeligeri, 3 L. ivanovii, 1 L. grayi and 3 L. monocytogenes. Amplifications were first carried out at an annealing temperature of 70° C. The results of this evaluation are summarized in Table 9.

TABLE 9

% Positive Response for PCR-Based Assay of L. spp.: Effect of Priming Site Location

| Priming Sites: | 76 | 88 | 624 |
| --- | --- | --- | --- |
| rc483 | 80% | 85% | Not Applicable |
| rc555 | 100% | 100% | Not Applicable |
| rc573 | 100% | 100% | Not Applicable |
| rc824 | 0% | Not Determined | 0% |

The 76, 88, rc555 and rc573 priming sites all appear to be viable at a 70° C. annealing temperature, based on the 100% positive response that is achieved with any combination of these primers. When rc483 is used in conjunction with 76 or 88 the positive response drops off to the 80–85% response range. Decreasing the annealing temperature to 65° C. increases the response to 97%. Although both 76/rc824 and 624/rc824 generated no PCR product with a 70° C. annealing temperature, when the temperature was decreased to 65° C. the positive response increased to 97%. In all of the tests at 65° C. the only false negative was a single L. grayi strain. It appears that the melting temperatures of the rc824 and rc483 primers are too low to permit their effective use at a 70° C. No fuirther testing was done with these primers. The 76, 88, rc555 and rc573 priming sites all appear to be viable at a 70° C. annealing temperature.

L. grayi and L. murrayi are not as frequently encountered as other L. spp. However, since no sequence data was determined for these species, additional strains were tested with the primer sets that scored 100%. The test group consisted of 7 strains of L. grayi and 4 strains of L. murrayi. The positive response of the various primer sets was as follows:

76/rc555 50%;
76/rc573 18%;
88/rc555 27%; and
88/rc573 9%.

The weak and variable response of L. grayi and L. murrayi to the genus level priming sites is not surprising. DNA-DNA hybridization studies have shown that L. grayi and L. murrayi were only moderately related to reference strains of L. monocytogenes, L. innocua, L. seeligeri, L. welshimeri and L. ivanovii, i.e., at 3–29% and 1–9% respectively. (Rocourt et al., Curr. Microbiol. 7:383–388 (1982).) Based on this and other DNA-DNA hybridization studies, it has been suggested that L. grayi and L. murrayi are sufficiently different from L. monocytogenes to merit their separation into a new genus, Murraya grayi. The issue of how these species should be classified is currently undecided. Regardless of how strains from these two species are ultimately classified, the genus level primers show a generally weak positive response to strains from this group. The strength of the positive response is expected to be extremely dependent on the level of DNA used in the assay with sensitivity to L. grayi and L. murrayi strains expected to run 3 orders of magnitude poorer than other Listeria species.

EXAMPLE 7

Selection of Listeria SPP. Diagnostic Primers on the Basis of Sensitivity to Annealing Temperature To minimize the likelihood that L. spp. primers would generate PCR products from mismatched priming in non-Listeria strains, the relationship between annealing temperature and amplification specificity was evaluated. Amplifications were carried out on a test panel of 7 strains at an annealing temperature of 70° C. Annealing temperature was then decreased in 5° C. increments until the onset of nonspecific amplification products. The primer combinations of 76/rc573 and 88/rc573 both showed nonspecific products at 65° C. At 60° C. 88/rc555 began to show nonspecific products. Such products were not observed for the 76/rc555 primer set until the annealing temperature was reduced to 55° C. Since the 76/rc555 primer set was least likely to generate nonspecific amplification products this primer set was the primary candidate for the Listeria spp. detection assay.

EXAMPLE 8

Final Evaluation of Listeria SPP. Diagnostic Primers

Final Evaluation of Listeria spp. Candidate Primer Set

Before the 76/rc555 primer selection was confirmed, the accuracy of this set was evaluated for additional L. spp. strains. This entire test panel consisted of 73 strains that were broken down by species as follows: 9 L. monocytogenes, 34 L. innocua, 5 L. welshimeri, 11 L. seeligeri, 3 L. ivanovii, 7 L. grayi and 4 L. murrayi. PCR conditions were the same as those specified above except that only a 70° C. annealing temperature was used. All of the strains belonging to the species *L. monocytogenes, L. innocua, L. welshimeri, L. seeligeri,* and *L. ivanovii,* tested at 100% positive for the 76/rc555 primer set. As reported above, the test group of 7 *L. grayi* and 4 *L. murrayi* strains scored at 50%.

The accuracy of the 76/rc555 primer set was also evaluated on a non-Listeria spp. test panel consisting of 65 strains that represent a variety of related gram positive strains and enteric gram negative strains. The species tested are summarized in Table 10.

TABLE 10

Negative Test Panel for Screening of *Listeria spp.* Primer Set
1515-30-76/1515(8585)-30-rc555

| Species | No. of Strains | Species | No. of Strains |
|---|---|---|---|
| Aeromonas species | 1 | Salmonella enteritidis | 3 |
| Bacillus cereus | 4 | Salmonella redlands | 1 |
| Bacillus subtilis | 2 | Salmonella virchow | 1 |
| Bacillus thuringiensis | 3 | Salmonella santiago | 2 |
| Carnohacterium piscicola | 2 | Staphylococcus aureus | 4 |
| Enterococcus casseliflavus | 1 | Staphylococcus carnosus | 2 |
| Enterococcus faecalis | 10 | Staphylococcus epidermidis | 6 |
| Enterococcus faecium | 1 | | |
| Enterococcus species | 1 | Staphylococcus species | 1 |
| Escherichia coli | 2 | Staphylococcus warneri | 2 |
| Lactococcus lactis | 9 | Staphylococcus xylosus | 1 |
| | | Brochothrix thermosphacta | 8 |

Figure 7:
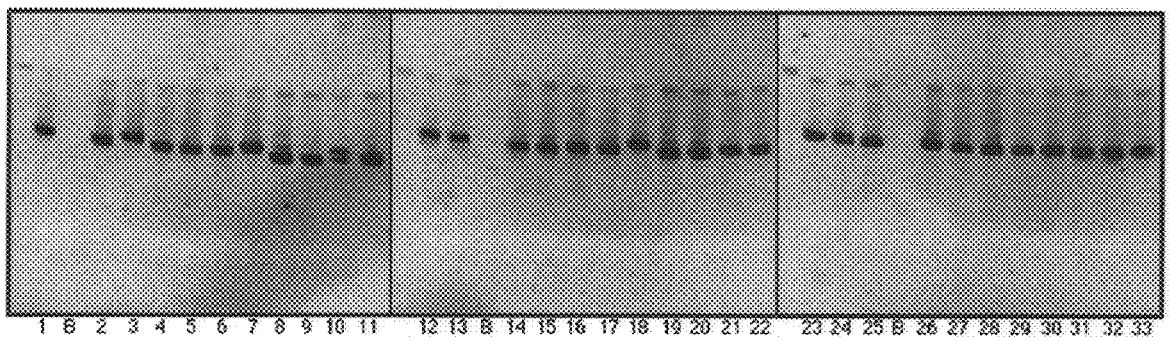
FIG. 7 is a gel showing Listeria spp. positive test panel response for PCR products generated from primer set 1515-30-76/1515(8585)-30-rc555. The specific lanes are identified in Table 11.
Figure 8A:
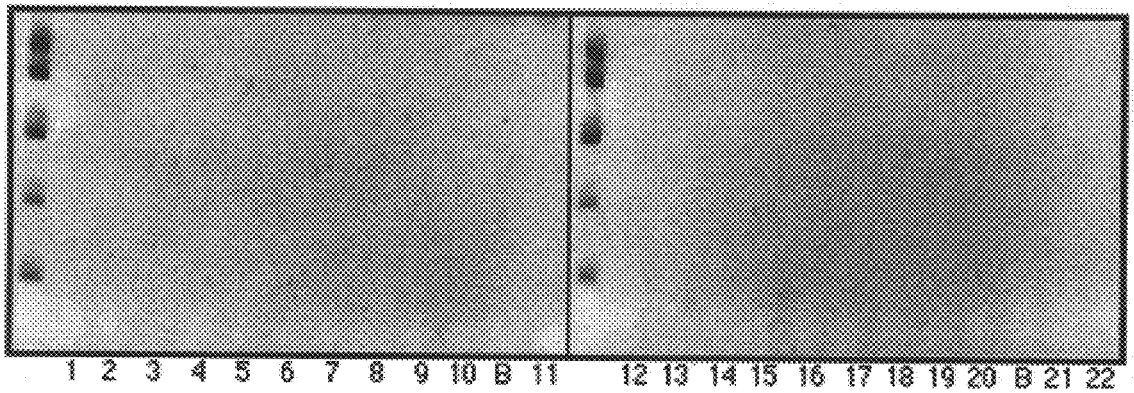
FIGS. 8A–8B is a gel showing Listeria spp. negative test panel response for PCR products generated from primer set 1515-30-76/1515(8585)-30-rc555. The specific lanes are identified in Table 12.
Figure 8B:
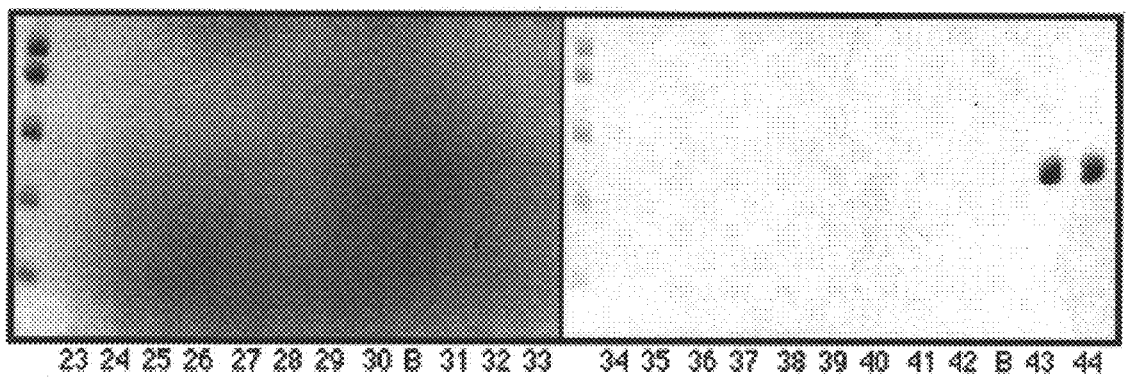

None of the strains in Table 10 produced a positive PCR response for annealing temperatures ranging from 60–70° C. Examples of the results of Listeria spp. and non-Listeria spp. test panels for the 76/rc555 primer pair are shown by gel analysis in FIGS. 7A and 7B respectively. The lanes are identified as follows in Table 11:

TABLE 11

*Listeria spp.* positive test panel response
for PCR products generated from primer set
1515-30-76/1515(8585)-30-rc555
corresponding to FIG. 4

| Lane | Strain | Lane | Strain |
|---|---|---|---|
| 1 | L. seeligeri #2874 | 17 | L. innocua #3429 |
| B | BLANK | 18 | L. ivanovii #3357 |
| 2 | L. innocua #2921 | 19 | L. welshimeri #3558 |
| 3 | L. ivanovii #3072 | 20 | L. innocua #3571 |
| 4 | L. innocua #3241 | 21 | L. innocua #3797 |
| 5 | L. innocua #3244 | 22 | L. seeligeri #3828 |
| 6 | L. seeligeri #3327 | 23 | L. innocua #4094 |
| 7 | L. ivanovii #3340 | 24 | L. innocua #4101 |
| 8 | L. innocua #3352 | 25 | L. innocua #4323 |
| 9 | L. welshimeri #3354 | B | BLANK |
| 10 | L. grayi #3356 | 26 | L. seeligeri #4333 |
| 11 | L. welshimeri #3359 | 27 | L. innocua #4442 |
| 12 | L. seeligeri #3371 | 28 | L. innocua #4450 |
| 13 | L. seeligeri #3374 | 29 | L. innocua #4452 |
| B | BLANK | 30 | L. innocua #4463 |
| 14 | L. welshimeri #3411 | 31 | L. monocytogenes #3847 |
| 15 | L. welshimeri #3412 | 32 | L. monocytogenes #4324 |
| 16 | L. innocua #3420 | 33 | L. monocytogenes #4341 |

TABLE 12

*Listeria spp.* negative test panel response for
PCR products generated from primer set
1515-30-76/1515(8585)-30-rc555

| Lane | Strain |
|---|---|
| 1 | Escherichia coli #642 |
| 2 | Staphylococcus epidermidis #764 |
| 3 | Staphylococcus epidermidis #783 |
| 4 | Staphylococcus aureus #789 |
| 5 | Staphylococcus epidermidis #796 |
| 6 | Staphylococcus warneri #797 |
| 7 | Staphylococcus warneri #799 |
| 8 | Staphylococcus aureus #895 |
| 9 | Carnobacterium piscicola #920 |
| 10 | Staphylococcus aureus #923 |
| | BLANK |
| 11 | Bacillus subtilis #1011 |
| 12 | Bacillus subtilis #1041 |
| 13 | Staphylococcus carnosus #1090 |
| 14 | Staphylococcus carnosus #1091 |
| 15 | Staphylococcus xylosus #1120 |
| 16 | Carnobacterium piscicola #1160 |
| 17 | Bacillus thuringiensis #1221 |
| 18 | Staphylococcus aureus #2095 |
| 19 | Enterococcus faecalis #3074 |
| 20 | Lactococcus lactis #3584 |
| | BLANK |
| 21 | Lactococcus lactis #3585 |
| 22 | Lactococcus lactis #3586 |
| 23 | Lactococcus lactis #3587 |
| 24 | Lactococcus lactis #3588 |
| 25 | Lactococcus lactis #3589 |
| 26 | Lactococcus lactis #3590 |
| 27 | Lactococcus lactis #3591 |
| 28 | Escherichia coli #3803 |
| 29 | Lactococcus lactis #3817 |
| 30 | Aeromonas species #3818 |
| | BLANK |
| 31 | Enterococcus faecalis #3837 |
| 32 | Enterococcus faecalis #3838 |
| 33 | Enterococcus species #4095 |
| 34 | Enterococcus faecium #4428 |
| 35 | Salmonella redlands #4563 |
| 36 | Salmonella enteritidis #4565 |
| 37 | Salmonella enteritidis #4593 |
| 38 | Bacillus thuringiensis #4941 |
| 39 | Bacillus thuringiensis #5083 |
| 40 | Enterococcus faecalis #5504 |
| 41 | Salmonella virchow #5508 |
| 42 | Enterococcus casselflavus #5574 |
| | BLANK |
| 43 | Listeria monocytogenes #3844 |
| 44 | Listeria monocytogenes #3278 |

What is claimed is:

1. A method for determining whether an unknown bacterium is a *Listeria monocytogenes*, comprising (A) amplifying genomic DNA from (i) a positive test panel of *Listeria monocytogenes* strains and (ii) a negative test panel of non-*monocytogenes* Listeria strains with a primer derived from a pre-marker diagnostic fragment for *Listeria monocytogenes* selected from the group of nucleic acids corresponding to SEQ ID NOS:17, 18, and 19 to yield a 1300 bp diagnostic fragment for each of the positive and negative test panels;

(B) designing at least one amplification primer corresponding to at least one highly conserved region in the 1300 bp diagnostic fragment wherein said amplification primer is at least 15 bp in length and will not produce an amplification product from the negative test panel when annealed at 65–70° C.; and (C) amplifying genomic DNA of the unknown bacterium under suitable annealing temperatures with the at least one amplification primer of step (B), whereby obtaining at least one amplification product indicates that the unknown bacterium is a *Listeria monocytogenes*.

2. The method of claim 1 wherein the *Listeria monocytogenes* pre-marker diagnostic fragment is selected from the group consisting of nucleic acids corresponding to SEQ ID NOS:20–23.

3. The method of claim 1 wherein the diagnostic fragment is selected from the group of consisting nucleic acids corresponding to SEQ ID NOS:24–31 and 33–40.

4. The method of claim 1 wherein at least one diagnostic marker selected in step (B) is selected from the group consisting of nucleic acids corresponding to SEQ ID NOS:46–83.

5. The method of claim 1 wherein the at least one amplification primer is about 15 to 30 bp in length.

6. The method of claim 1 wherein the suitable annealing temperature is in the range of about 60° C. to 70° C.

7. A method for determining whether an unknown bacterium is a member of the genus Listeria, comprising (A) amplifying genomic DNA from (i) a positive test panel of *Listeria monocytogenes* strains and (ii) a negative test panel of non-*monocytogenes* Listeria strains with a primer derived from a pre-marker diagnostic fragment for *Listeria monocytogenes* strains selected from the group consisting of nucleic acids corresponding to SEQ ID NOS:17, 18, and 19 to yield a 1300 bp diagnostic fragment for each of the positive and negative test panels;

(B) designing amplification primers wherein said amplification primers are at least 15 bp in length and correspond to highly conserved regions in the 1300 bp diagnostic fragment and wherein said amplification primers will produce an amplification product from the positive and negative test panels when annealed at 60–70° C.; and (c) amplifying genomic DNA of the unknown bacterium under suitable annealing temperatures with the amplification primers of step (B), whereby obtaining amplification products indicates that the unknown bacterium is a member of the genus Listeria.

8. The method of claim 7 wherein at step (A) the diagnostic fragment is selected from the group consisting of nucleic acids corresponding to SEQ ID NOS:24–31 and 33–40.

9. The method of claim 7 wherein the *Listeria monocytogenes* pre-marker diagnostic fragment is selected from the group consisting of nucleic acids corresponding to SEQ ID NOS:20–23.

10. The method of claim 7 wherein the at least one diagnostic marker selected in step (B) is selected from the group consisting of nucleic acids corresponding to SEQ ID NOS:84–110.

11. The method of claim 7 wherein the at least one amplification primer is about 15 to 30 bp in length.

12. The method of claim 7 wherein the suitable annealing temperature is in the range of about 60° C. to 70° C.

13. A method for determining whether an unknown bacterium is a *Listeria monocytogenes*, comprising contacting the genomic DNA of the unknown bacterium with a nucleic acid probe selected from the group consisting of nucleic acids corresponding to SEQ ID NOS:46–83, and then detecting hybridization of the nucleic acid probe with the genomic DNA.

14. A method for determining whether an unknown bacterium is a *Listeria monocytogenes* comprising contacting the genomic DNA of the unknown bacterium with a nucleic acid probe selected from the group consisting of nucleic acids corresponding to SEQ ID NOS:84–110, and then detecting hybridization of the nucleic acid probe with the genomic DNA.

15. Isolated nucleic acid fragments selected from the group consisting of nucleic acid fragments corresponding to SEQ ID NOS:17 through 110.

16. An isolated nucleic acid fragment encoding the amino acid sequence as given in any one of SEQ ID NOS:32 and 41–45.

17. A nucleic acid fragment located on a diagnostic fragment of about 1300 bp and selected from the group consisting of nucleic acid fragments designated 1515(rc341×2)-26-363,
1515(rc341×2)-27-281,
1515-26-36,
1515-27-357,
1515-26-rc233, 1515(8585)-27-rc737,
1515(8585)-28-rc793
1515-30-76,
1515-30-88,
1515(8585)-30-624,
1515(8585)-30-rc483,
1515(8585)-30-rc555,
1515(8585)-30-rc573,
1515(8585)-30-rc824, the diagnostic fragment comprising
an open reading frame of about 855 bp encoding an amino acid sequence of any one of SEQ ID NOS:32 and 41–45.

* * * * *

SEQUENCE LISTING (1) GENERAL INFORMATION:

(iii) NUMBER OF SEQUENCES: 110

(2) INFORMATION FOR SEQ ID NO:1:

(i) SEQUENCE CHARACTERISTICS:
         (A) LENGTH:  12 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:1:

AGCTGATGCT AC                                                          12

(2) INFORMATION FOR SEQ ID NO:2:

(i) SEQUENCE CHARACTERISTICS:
         (A) LENGTH:  12 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:2:

AGTCGAACTG TC                                                          12

(2) INFORMATION FOR SEQ ID NO:3:

(i) SEQUENCE CHARACTERISTICS:
         (A) LENGTH:  12 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:3:

TTAGTCACGG CA                                                          12

(2) INFORMATION FOR SEQ ID NO:4:

(i) SEQUENCE CHARACTERISTICS:
         (A) LENGTH:  12 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:4:

TGCGATACCG TA                                                          12

(2) INFORMATION FOR SEQ ID NO:5:

(i) SEQUENCE CHARACTERISTICS:
         (A) LENGTH:  12 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:5:

```
CTACAGCTGA TG                                                                  12

(2) INFORMATION FOR SEQ ID NO:6:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:6:

GTCAGTCGAA CT                                                                  12

(2) INFORMATION FOR SEQ ID NO:7:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:7:

GGCATTAGTC AC                                                                  12

(2) INFORMATION FOR SEQ ID NO:8:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:8:

CGTATGCGAT AC                                                                  12

(2) INFORMATION FOR SEQ ID NO:9:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:9:

AACCTCGTGT AG                                                                  12

(2) INFORMATION FOR SEQ ID NO:10:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:10:

CATTCGGGTA CA                                                                  12

(2) INFORMATION FOR SEQ ID NO:11:
```

(i) SEQUENCE CHARACTERISTICS:
       (A) LENGTH:  12 base pairs
       (B) TYPE:  nucleic acid
       (C) STRANDEDNESS:  single
       (D) TOPOLOGY:  linear (ii) MOLECULE TYPE:  DNA (genomic)

(xi) SEQUENCE DESCRIPTION:  SEQ ID NO:11:

GCCCTTAGTG AA                                                               12

(2) INFORMATION FOR SEQ ID NO:12:

(i) SEQUENCE CHARACTERISTICS:
       (A) LENGTH:  12 base pairs
       (B) TYPE:  nucleic acid
       (C) STRANDEDNESS:  single
       (D) TOPOLOGY:  linear (ii) MOLECULE TYPE:  DNA (genomic)

(xi) SEQUENCE DESCRIPTION:  SEQ ID NO:12:

GCAGTTATGA CC                                                               12

(2) INFORMATION FOR SEQ ID NO:13:

(i) SEQUENCE CHARACTERISTICS:
       (A) LENGTH:  12 base pairs
       (B) TYPE:  nucleic acid
       (C) STRANDEDNESS:  single
       (D) TOPOLOGY:  linear (ii) MOLECULE TYPE:  DNA (genomic)

(xi) SEQUENCE DESCRIPTION:  SEQ ID NO:13:

CCAGCTATCT CT                                                               12

(2) INFORMATION FOR SEQ ID NO:14:

(i) SEQUENCE CHARACTERISTICS:
       (A) LENGTH:  12 base pairs
       (B) TYPE:  nucleic acid
       (C) STRANDEDNESS:  single
       (D) TOPOLOGY:  linear (ii) MOLECULE TYPE:  DNA (genomic)

(xi) SEQUENCE DESCRIPTION:  SEQ ID NO:14:

AGAAGGCAGT TG                                                               12

(2) INFORMATION FOR SEQ ID NO:15:

(i) SEQUENCE CHARACTERISTICS:
       (A) LENGTH:  12 base pairs
       (B) TYPE:  nucleic acid
       (C) STRANDEDNESS:  single
       (D) TOPOLOGY:  linear (ii) MOLECULE TYPE:  DNA (genomic)

(xi) SEQUENCE DESCRIPTION:  SEQ ID NO:15:

GGACAGAGCA TA                                                               12

(2) INFORMATION FOR SEQ ID NO:16:

(i) SEQUENCE CHARACTERISTICS:
       (A) LENGTH:  12 base pairs
       (B) TYPE:  nucleic acid
       (C) STRANDEDNESS:  single
       (D) TOPOLOGY:  linear (ii) MOLECULE TYPE: DNA (genomic)

(xi) SEQUENCE DESCRIPTION: SEQ ID NO:16:

CGTTTCGCTT CA                                                                                    12

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TGCTGTTTGG TTTGCTCTAG CCCAGTG                                                                    27

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CAACTTTCCA CATGGCGCGA TTATTTG                                                                    27

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGGGAACTGC CGAAGATCGT ACAGCA                                                                     26

(2) INFORMATION FOR SEQ ID NO:20:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: L MONO - 647 - PREMARKER (xi) SEQUENCE DESCRIPTION: SEQ ID NO:20:

GGACAGAGCA TAGTTGGATG GAAACAATCC GATCAGCGGG AACGTTTTTG ATAGATTCTG          60

CTGTTTGGTT TGCTCTAGCC CAGTGCCACG TGTCACAAAT AAGTTGCGCA TTATCTCGGC         120

CGCATGCTTC TGCTACTCGC CAAGCTGCTT GTAAGTCTGC TACACCGCTA TATGGCATAA         180

ATTCTAAACC AATAATTAAT TCTTCTGCGC GGTCACATAA TTCACCAAGC GCGACGATGA         240

TTTGTTCCTC AGGGATTTTT TCAAGCAAAC CACAATTAAT ATGTTTGACG CCAAATAATC         300

GCGCCATGTG GAAAGTTGTT TGCTCTTTCT TTTGTTGTTC TGCTGTACGA TCTTCGGCAG         360

```
TTCCCCACTG AGTTATGTAC TCCACTTCTG TTACTTTCAT GTTATGCTCT GTCC          414
```

(2) INFORMATION FOR SEQ ID NO:21:

(i) SEQUENCE CHARACTERISTICS:
        (A) LENGTH:  414 base pairs
        (B) TYPE:  nucleic acid
        (C) STRANDEDNESS:  single
        (D) TOPOLOGY:  linear (ii) MOLECULE TYPE:  DNA (genomic)

(iv) ANTI-SENSE:  YES (vi) ORIGINAL SOURCE:
        (B) STRAIN:  L MONO - 647 - PREMARKER (xi) SEQUENCE DESCRIPTION:  SEQ ID NO:21:

```
GGACAGAGCA TAACATGAAA GTAACAGAAG TGGAGTACAT AACTCAGTGG GGAACTGCCG     60

AAGATCGTAC AGCAGAACAA CAAAAGAAAG AGCAAACAAC TTTCCACATG GCGCGATTAT    120

TTGGCGTCAA ACATATTAAT TGTGGTTTGC TTGAAAAAAT CCCTGAGGAA CAAATCATCG    180

TCGCGCTTGG TGAATTATGT GACCGCGCAG AAGAATTAAT TATTGGTTTA GAATTTATGC    240

CATATAGCGG TGTAGCAGAC TTACAAGCAG CTTGGCGAGT AGCAGAAGCA TGCGGCCGAG    300

ATAATGCGCA ACTTATTTGT GACACGTGGC ACTGGGCTAG AGCAAACCAA ACAGCAGAAT    360

CTATCAAAAA CGTTCCCGCT GATCGGATTG TTTCCATCCA ACTATGCTCT GTCC          414
```

(2) INFORMATION FOR SEQ ID NO:22:

(i) SEQUENCE CHARACTERISTICS:
        (A) LENGTH:  414 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (A) ORGANISM:  L MONO - 1324 - PREMARKER (xi) SEQUENCE DESCRIPTION:  SEQ ID NO:22:

```
GGACAGAGCA TAGTTGGATA GAAACAATCC GATCAGCGGG AACATTTTTG ATAGATTCAG     60

CTGTTTGATT TGCTCTAGCC CAGTGCCATG TGTCACAAAT AAGTTGCGCG TTATCTCGTC    120

CGCATGCTTC TGCTACTCGC CAAGCTGCTT GTAAGTCTGC TACACCGCTA TATGGCATAA    180

ATTCTAAACC AATAATTAAT TCTTCTGCGC GGTCACATAA TTCACCAAGC GCGACAATGA    240

TTTGTTCCTC AGGGATTTTT TCAAGCAAAC CACAATTAAT ATGTTTGACG CCAAATAATC    300

GCGCCATGTG GAAAGTTGTT TGCTCTTTCT TTTGTTGTTC TGCTGTACGA TCTTCGGCAG    360

TTCCCCACTG GGTTATGTAC TCCACTTCTG TTACTTTCAT GTTATGCTCT GTCC          414
```

(2) INFORMATION FOR SEQ ID NO:23:

(i) SEQUENCE CHARACTERISTICS:
        (A) LENGTH:  414 base pairs
        (B) TYPE:  nucleic acid
        (C) STRANDEDNESS:  single
        (D) TOPOLOGY:  linear (ii) MOLECULE TYPE:  DNA (genomic)

(iv) ANTI-SENSE:  YES (vi) ORIGINAL SOURCE:
        (B) STRAIN:  L MONO - 1324 - PREMARKER (xi) SEQUENCE DESCRIPTION: SEQ ID NO:23:

```
GGACAGAGCA TAACATGAAA GTAACAGAAG TGGAGTACAT AACCCAGTGG GGAACTGCCG      60
AAGATCGTAC AGCAGAACAA CAAAAGAAAG AGCAAACAAC TTTCCACATG GCGCGATTAT     120
TTGGCGTCAA ACATATTAAT TGTGGTTTGC TTGAAAAAAT CCCTGAGGAA CAAATCATTG     180
TCGCGCTTGG TGAATTATGT GACCGCGCAG AAGAATTAAT TATTGGTTTA GAATTTATGC     240
CATATAGCGG TGTAGCAGAC TTACAAGCAG CTTGGCGAGT AGCAGAAGCA TGCGGACGAG     300
ATAACGCGCA ACTTATTTGT GACACATGGC ACTGGGCTAG AGCAAATCAA ACAGCTGAAT     360
CTATCAAAAA TGTTCCCGCT GATCGGATTG TTTCTATCCA ACTATGCTCT GTCC           414
```

(2) INFORMATION FOR SEQ ID NO:24:

(i) SEQUENCE CHARACTERISTICS:
(A) LENGTH: 1354 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(B) STRAIN: L MONO - 647 - D. FRAG (xi) SEQUENCE DESCRIPTION: SEQ ID NO:24:

```
TAAGCAAGGA AGTATCTGAT AAAGTCCATC TGTATTTGCA TAGTTGTTAC ACATTGGCGA      60
TACGACAAAT CTGTTAGGCA CCTTCATCGG CCCGATATCA ATAGGTGAAA ACATCGAATT     120
AAATTTCAAA AATAACACAT TCCTTTCACA GGGAGTCTTC CTACTACGTT ATTATTTTCA     180
CATAAGCGAG TAGGTGTTTA GCGTGGAGAA ATTTCTGGCC ATGCTTCGTC TAATACTTTT     240
TTCGTGGCAT TGTATACTTT AAGGGCGGCA TACTCTAAAC CAGTTGCTAC CATAGAGTCT     300
GAAATAACTT CGACTCCCAT CACACGTGGA TTTACACCAT GTTCTTTTAA AATTTTTGCA     360
AAACCGACCG TATCTCCGTA GCCTTCTCCA GGAGCTAGAC GATCATGAAG TGATTCCTCA     420
CGAAGTTCTT TGTAAGGCGT TTCGTGGACA TCGCATAGTT GGATGGAAAC AATCCGATCA     480
GCGGGAACGT TTTTGATAGA TTCTGCTGTT TGGTTTGCTC TAGCCCAGTG CCACGTGTCA     540
CAAATAAGTT GCGCATTATC TCGGCCGCAT GCTTCTGCTA CTCGCCAAGC TGCTTGTAAG     600
TCTGCTACAC CGCTATATGG CATAAATTCT AAACCAATAA TTAATTCTTC TGCGCGGTCA     660
CATAATTCAC CAAGCGCGAC GATGATTTGT TCCTCAGGGA TTTTTTCAAG CAAACCACAA     720
TTAATATGTT TGACGCCAAA TAATCGCGCC ATGTGGAAAG TTGTTTGCTC TTTCTTTTGT     780
TGTTCTGCTG TACGATCTTC GGCAGTTCCC CACTGAGTTA TGTACTCCAC TTCTGTTACT     840
TTCATGTTAT GCTCGTCTAA AATCCGCAAC ATGTCTTCAT CCGTTAATCC GGCAGCTAGT     900
GCATCTACAT AGTTTTCTGC ACGCAAGCCA ATTCCGTCAA AACCGTTTTC CGCAGCGACT     960
TTTACTCGTT TAGGAAAAGA TACCTCTGTT CCAAGCGTAT AAGAGCTAAT CGTGATGGGG    1020
CATTTTTTTA GGTTGCCATT TGCATTTGTC ATAAAAATTA TCTCCTCTCC ATAATAAAAA    1080
TTACAAGAAA CTTTGATAAT ATTTTCACAA ACACCAGTAA AAAAATTAAT TCCGCTTAAT    1140
TAAAAACCTC TGATGTGATA ACGCCTTCAA TAGTTGAAAA TGGAACTGGA CAGTTAACCT    1200
ATTCTACCGT ATATTGGTTT TTAAGGAATA GTTTATTTCA CTGGCGTAAC TACAGTCTAA    1260
TTGTATTATG ACTATTCCAT AAAAACAAAT TGGTATTGTT CTATTAATTG ATAGATAAAT    1320
TGCATAGATA ACTTTTTAGT TAGGAGAGAA GCAT                                1354
```

(2) INFORMATION FOR SEQ ID NO:25:

(i) SEQUENCE CHARACTERISTICS:
    (A) LENGTH: 1354 base pairs
    (B) TYPE: nucleic acid
    (C) STRANDEDNESS: single
    (D) TOPOLOGY: linear (ii) MOLECULE TYPE: DNA (genomic)

(iv) ANTI-SENSE: YES (vi) ORIGINAL SOURCE:
    (B) STRAIN: L MONO 647 - D.F.

(xi) SEQUENCE DESCRIPTION: SEQ ID NO:25:

```
ATGCTTCTCT CCTAACTAAA AAGTTATCTA TGCAATTTAT CTATCAATTA ATAGAACAAT    60
ACCAATTTGT TTTTATGGAA TAGTCATAAT ACAATTAGAC TGTAGTTACG CCAGTGAAAT   120
AAACTATTCC TTAAAAACCA ATATACGGTA GAATAGGTTA ACTGTCCAGT TCCATTTTCA   180
ACTATTGAAG GCGTTATCAC ATCAGAGGTT TTTAATTAAG CGGAATTAAT TTTTTTACTG   240
GTGTTTGTGA AAATATTATC AAAGTTTCTT GTAATTTTTA TTATGGAGAG GAGATAATTT   300
TTATGACAAA TGCAAATGGC AACCTAAAAA AATGCCCCAT CACGATTAGC TCTTATACGC   360
TTGGAACAGA GGTATCTTTT CCTAAACGAG TAAAAGTCGC TGCGGAAAAC GGTTTTGACG   420
GAATTGGCTT GCGTGCAGAA AACTATGTAG ATGCACTAGC TGCCGGATTA ACGGATGAAG   480
ACATGTTGCG GATTTTAGAC GAGCATAACA TGAAAGTAAC AGAAGTGGAG TACATAACTC   540
AGTGGGGAAC TGCCGAAGAT CGTACAGCAG AACAACAAAA GAAAGAGCAA ACAACTTTCC   600
ACATGGCGCG ATTATTTGGC GTCAAACATA TTAATTGTGG TTTGCTTGAA AAAATCCCTG   660
AGGAACAAAT CATCGTCGCG CTTGGTGAAT TATGTGACCG CGCAGAAGAA TTAATTATTG   720
GTTTAGAATT TATGCCATAT AGCGGTGTAG CAGACTTACA AGCAGCTTGG CGAGTAGCAG   780
AAGCATGCGG CCGAGATAAT GCGCAACTTA TTTGTGCACA CGTGGCACTGG GCTAGAGCAA   840
ACCAAACAGC AGAATCTATC AAAAACGTTC CCGCTGATCG GATTGTTTCC ATCCAACTAT   900
GCGATGTCCA CGAAACGCCT TACAAAGAAC TTCGTGAGGA ATCACTTCAT GATCGTCTAG   960
CTCCTGGAGA AGGCTACGGA GATACGGTCG GTTTTGCAAA AATTTTAAAA GAACATGGTG  1020
TAAATCCACG TGTGATGGGA GTCGAAGTTA TTTCAGACTC TATGGTAGCA ACTGGTTTAG  1080
AGTATGCCGC CCTTAAAGTA TACAATGCCA CGAAAAAAGT ATTAGACGAA GCATGGCCAG  1140
AAATTTCTCC ACGCTAAACA CCTACTCGCT TATGTGAAAA TAATAACGTA GTAGGAAGAC  1200
TCCCTGTGAA AGGAATGTGT TATTTTTGAA ATTTAATTCG ATGTTTTCAC CTATTGATAT  1260
CGGGCCGATG AAGGTGCCTA ACAGATTTGT CGTATCGCCA ATGTGTAACA ACTATGCAAA  1320
TACAGATGGA CTTTATCAGA TACTTCCTTG CTTA                              1354
```

(2) INFORMATION FOR SEQ ID NO:26:

(i) SEQUENCE CHARACTERISTICS:
        (A) LENGTH: 1327 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: L MONO 899 D.F.

(xi) SEQUENCE DESCRIPTION: SEQ ID NO:26:

```
ATCTGTATTT GCATAGTTGT TACACATTGG CGATACGACA AATCTGTTAG GCACCTTCAT    60
```

```
CGGCCCGATA TCAATAGGTG AAAACATCGA ATTAAATTTC AAAAATAACA CATTCCTTTC      120

ACAGGGAGTC TTCCTACTAC GTTATTATTT TCACATAAGC GAGTAGGTGT TTAGCGTGGA      180

GAAATTTCTG GCCATGCTTC GTCTAATACT TTTTTCGTGG CATTGTATAC TTTAAGGGCG      240

GCATACTCTA AACCAGTTGC TACCATAGAG TCTGAAATAA CTTCGACTCC CATCACACGT      300

GGATTTACAC CATGTTCTTT TAAAATTTTT GCAAAACCGA CCGTATCTCC GTAGCCTTCT      360

CCAGGAGCTA GACGATCATG AAGTGATTCC TCACGAAGTT CTTTGTAAGG CGTTTCGTGG      420

ACATCGCATA GTTGGATGGA ACAATCCGA TCAGCGGGAA CGTTTTTGAT AGATTCTGCT       480

GTTTGGTTTG CTCTAGCCCA GTGCCACGTG TCACAAATAA GTTGCGCATT ATCTCGGCCG     540

CATGCTTCTG CTACTCGCCA AGCTGCTTGT AAGTCTGCTA CACCGCTATA TGGCATAAAT     600

TCTAAACCAA TAATTAATTC TTCTGCGCGG TCACATAATT CACCAAGCGC GACGATGATT     660

TGTTCCTCAG GGATTTTTTC AAGCAAACCA CAATTAATAT GTTTGACGCC AAATAATCGC     720

GCCATGTGGA AAGTTGTTTG CTCTTTCTTT TGTTGTTCTG CTGTACGATC TTCGGCAGTT     780

CCCCACTGAG TTATGTACTC CACTTCTGTT ACTTTCATGT TATGCTCGTC TAAAATCCGC     840

AACATGTCTT CATCCGTTAA TCCGGCAGCT AGTGCATCTA CATAGTTTTC TGCACGCAAG     900

CCAATTCCGT CAAAACCGTT TTCCGCAGCG ACTTTTACTC GTTTAGGAAA AGATACCTCT     960

GTTCCAAGCG TATAAGAGCT AATCGTGATG GGGCATTTTT TTAGGTTGCC ATTTGCATTT    1020

GTCATAAAAA TTATCTCCTC TCCATAATAA AAATTACAAG AAACTTTGAT AATATTTTCA    1080

CAAACACCAG TAAAAAAATT AATTCCGCTT AATTAAAAAC CTCTGATGTG ATAACGCCTT    1140

CAATAGTTGA AAATGGAACT GGACAGTTAA CCTATTCTAC CGTATATTGG TTTTTAAGGA    1200

ATAGTTTATT TCACTGGCGT AACTACAGTC TAATTGTATT ATGACTATTC CATAAAAACA    1260

AATTGGTATT GTTCTATTAA TTGATAGATA AATTGCATAG ATAACTTTTT AGTTAGGAGA    1320

GAAGCAT                                                              1327
```

(2) INFORMATION FOR SEQ ID NO:27:

(i) SEQUENCE CHARACTERISTICS:
        (A) LENGTH: 1327 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (B) STRAIN: L MONO 899 D.F.

(xi) SEQUENCE DESCRIPTION: SEQ ID NO:27:

```
ATGCTTCTCT CCTAACTAAA AAGTTATCTA TGCAATTTAT CTATCAATTA ATAGAACAAT      60

ACCAATTTGT TTTTATGGAA TAGTCATAAT ACAATTAGAC TGTAGTTACG CCAGTGAAAT     120

AAACTATTCC TTAAAAACCA ATATACGGTA GAATAGGTTA ACTGTCCAGT TCCATTTTCA     180

ACTATTGAAG GCGTTATCAC ATCAGAGGTT TTTAATTAAG CGGAATTAAT TTTTTTACTG     240

GTGTTTGTGA AAATATTATC AAAGTTTCTT GTAATTTTTA TTATGGAGAG GAGATAATTT     300

TTATGACAAA TGCAAATGGC AACCTAAAAA ATGCCCCAT CACGATTAGC TCTTATACGC      360

TTGGAACAGA GGTATCTTTT CCTAAACGAG TAAAAGTCGC TGCGGAAAAC GGTTTTGACG     420

GAATTGGCTT GCGTGCAGAA AACTATGTAG ATGCACTAGC TGCCGGATTA ACGGATGAAG     480

ACATGTTGCG GATTTTAGAC GAGCATAACA TGAAAGTAAC AGAAGTGGAG TACATAACTC     540
```

```
AGTGGGGAAC TGCCGAAGAT CGTACAGCAG AACAACAAAA GAAAGAGCAA ACAACTTTCC       600

ACATGGCGCG ATTATTTGGC GTCAAACATA TTAATTGTGG TTTGCTTGAA AAAATCCCTG       660

AGGAACAAAT CATCGTCGCG CTTGGTGAAT TATGTGACCG CGCAGAAGAA TTAATTATTG       720

GTTTAGAATT TATGCCATAT AGCGGTGTAG CAGACTTACA AGCAGCTTGG CGAGTAGCAG       780

AAGCATGCGG CCGAGATAAT GCGCAACTTA TTTGTGACAC GTGGCACTGG GCTAGAGCAA       840

ACCAAACAGC AGAATCTATC AAAAACGTTC CCGCTGATCG GATTGTTTCC ATCCAACTAT       900

GCGATGTCCA CGAAACGCCT ACAAAGAAC  TTCGTGAGGA ATCACTTCAT GATCGTCTAG       960

CTCCTGGAGA AGGCTACGGA GATACGGTCG GTTTTGCAAA AATTTTAAAA GAACATGGTG      1020

TAAATCCACG TGTGATGGGA GTCGAAGTTA TTTCAGACTC TATGGTAGCA ACTGGTTTAG      1080

AGTATGCCGC CCTTAAAGTA TACAATGCCA CGAAAAAAGT ATTAGACGAA GCATGGCCAG      1140

AAATTTCTCC ACGCTAAACA CCTACTCGCT TATGTGAAAA TAATAACGTA GTAGGAAGAC      1200

TCCCTGTGAA AGGAATGTGT TATTTTTGAA ATTTAATTCG ATGTTTTCAC CTATTGATAT      1260

CGGGCCGATG AAGGTGCCTA ACAGATTTGT CGTATCGCCA ATGTGTAACA ACTATGCAAA      1320

TACAGAT                                                                1327

(2) INFORMATION FOR SEQ ID NO:28:

(i) SEQUENCE CHARACTERISTICS:
        (A) LENGTH:  1274 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (B) STRAIN:  L MONO 3386 D.F.

(xi) SEQUENCE DESCRIPTION: SEQ ID NO:28:

AGGCACCTTC ATCGGCCCGA TATCAATAGG TGAAAACATC GAATTAAATT TCAAAAATAA        60

CACATTCCTT TCACAGGGAG TCTTCCTACT ACGTTATTAT TTTCACATAA GCGAGTAGGT       120

GTTTAGCGTG GAGAAATTTC TGGCCATGCT TCGTCTAATA CTTTTTTCGT GGCATTGTAT       180

ACTTTAAGGG CGGCATACTC TAAACCAGTT GCTACCATAG AGTCTGAAAT AACTTCGACT       240

CCCATCACAC GTGGATTTAC ACCATGTTCT TTTAAAATTT TTGCAAAACC GACCGTATCT       300

CCGTAGCCTT CTCCAGGAGC TAGACGATCA TGAAGTGATT CCTCACGAAG TTCTTTGTAA       360

GGCGTTTCGT GGACATCGCA TAGTTGGATG GAAACAATCC GATCAGCGGG AACGTTTTTG       420

ATAGATTCTG CTGTTTGGTT TGCTCTAGCC CAGTGCCACG TGTCACAAAT AAGTTGCGCA       480

TTATCTCGGC CGCATGCTTC TGCTACTCGC CAAGCTGCTT GTAAGTCTGC TACACCGCTA       540

TATGGCATAA ATTCTAAACC AATAATTAAT TCTTCTGCGC GGTCACATAA TTCACCAAGC       600

GCGACGATGA TTTGTTCCTC AGGGATTTTT TCAAGCAAAC CACAATTAAT ATGTTTGACG       660

CCAAATAATC GCGCCATGTG GAAAGTTGTT TGCTCTTTCT TTTGTTGTTC TGCTGTACGA       720

TCTTCGGCAG TTCCCCACTG AGTTATGTAC TCCACTTCTG TTACTTTCAT GTTATGCTCG       780

TCTAAAATCC GCAACATGTC TTCATCCGTT AATCCGGCAG CTAGTGCATC TACATAGTTT       840

TCTGCACGCA AGCCAATTCC GTCAAAACCG TTTTCCGCAG CGACTTTTAC TCGTTTAGGA       900

AAAGATACCT CTGTTCCAAG CGTATAAGAG CTAATCGTGA TGGGGCATTT TTTTAGGTTG       960

CCATTTGCAT TTGTCATAAA AATTATCTCC TCTCCATAAT AAAAATTACA AGAAACTTTG      1020

ATAATATTTT CACAAACACC AGTAAAAAAA TTAATTCCGC TTAATTAAAA ACCTCTGATG      1080
```

```
TGATAACGCC TTCAATAGTT GAAAATGGAA CTGGACAGTT AACCTATTCT ACCGTATATT    1140

GGTTTTTAAG GAATAGTTTA TTTCACTGGC GTAACTACAG TCTAATTGTA TTATGACTAT    1200

TCCATAAAAA CAAATTGGTA TTGTTCTATT AATTGATAGA TAAATTGCAT AGATAACTTT    1260

TTAGTTAGGA GAGA                                                    1274

(2) INFORMATION FOR SEQ ID NO:29:

(i) SEQUENCE CHARACTERISTICS:
        (A) LENGTH: 1274 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (B) STRAIN: L MONO 3386 D.F (xi) SEQUENCE DESCRIPTION: SEQ ID NO:29:

TCTCTCCTAA CTAAAAAGTT ATCTATGCAA TTTATCTATC AATTAATAGA ACAATACCAA      60

TTTGTTTTTA TGGAATAGTC ATAATACAAT TAGACTGTAG TTACGCCAGT GAAATAAACT     120

ATTCCTTAAA AACCAATATA CGGTAGAATA GGTTAACTGT CCAGTTCCAT TTCAACTAT     180

TGAAGGCGTT ATCACATCAG AGGTTTTTAA TTAAGCGGAA TTAATTTTTT TACTGGTGTT    240

TGTGAAAATA TTATCAAAGT TTCTTGTAAT TTTTATTATG GAGAGGAGAT AATTTTTATG    300

ACAAATGCAA ATGGCAACCT AAAAAAATGC CCCATCACGA TTAGCTCTTA TACGCTTGGA    360

ACAGAGGTAT CTTTTCCTAA ACGAGTAAAA GTCGCTGCGG AAAACGGTTT TGACGGAATT    420

GGCTTGCGTG CAGAAAACTA TGTAGATGCA CTAGCTGCCG GATTAACGGA TGAAGACATG    480

TTGCGGATTT TAGACGAGCA TAACATGAAA GTAACAGAAG TGGAGTACAT AACTCAGTGG    540

GGAACTGCCG AAGATCGTAC AGCAGAACAA CAAAAGAAAG AGCAAACAAC TTTCCACATG    600

GCGCGATTAT TTGGCGTCAA ACATATTAAT TGTGGTTTGC TTGAAAAAAT CCCTGAGGAA    660

CAAATCATCG TCGCGCTTGG TGAATTATGT GACCGCGCAG AAGAATTAAT TATTGGTTTA    720

GAATTTATGC CATATAGCGG TGTAGCAGAC TTACAAGCAG CTTGGCGAGT AGCAGAAGCA    780

TGCGGCCGAG ATAATGCGCA ACTTATTTGT GACACGTGGC ACTGGGCTAG AGCAAACCAA    840

ACAGCAGAAT CTATCAAAAA CGTTCCCGCT GATCGGATTG TTTCCATCCA ACTATGCGAT    900

GTCCACGAAA CGCCTTACAA AGAACTTCGT GAGGAATCAC TTCATGATCG TCTAGCTCCT    960

GGAGAAGGCT ACGGAGATAC GGTCGGTTTT GCAAAAATTT TAAAAGAACA TGGTGTAAAT   1020

CCACGTGTGA TGGGAGTCGA AGTTATTTCA GACTCTATGG TAGCAACTGG TTTAGAGTAT   1080

GCCGCCCTTA AGTATACAA TGCCACGAAA AAAGTATTAG ACGAAGCATG GCCAGAAATT   1140

TCTCCACGCT AAACACCTAC TCGCTTATGT GAAAATAATA ACGTAGTAGG AAGACTCCCT   1200

GTGAAAGGAA TGTGTTATTT TTGAAATTTA ATTCGATGTT TTCACCTATT GATATCGGGC   1260

CGATGAAGGT GCCT                                                     1274

(2) INFORMATION FOR SEQ ID NO:30:

(i) SEQUENCE CHARACTERISTICS:
        (A) LENGTH: 1289 base pairs
        (B) TYPE: nucleic acid
        (C) STRANDEDNESS: single
        (D) TOPOLOGY: linear (ii) MOLECULE TYPE: DNA (genomic)
```

-continued (vi) ORIGINAL SOURCE:
    (B) STRAIN: L MONO 1324 D.F.

(xi) SEQUENCE DESCRIPTION: SEQ ID NO:30:

```
CAAATCTGTT AGGCACCTTC ATCGGCCCGA TATCAATAGG TGAAAACATC GAATTAAATT      60
TCAAAAATAA CACATTCCTT TCACAGGGAG TCTTCCTACT ACGTTATCAT TTTCACATAA     120
CTAAGTAGGT GTTTAGCGTG GAGAAATCTC TGGCCATGCT TCGTCTAATA CTTTTTTCGT     180
GGCATTGTAT ACTTTAAGAG CGGCATACTC TAAACCAGTT GCTACCATAG AGTCTGAAAT     240
AACTTCAACT CCCATCACAC GTGGATTTAC ACCATGCTCT TTTAAAATTT TTGCAAAACC     300
GACCGTATCT CCGTATCCTT CTCCAGGAGC TAAACGATCA TGAAGTGATT CTTCACGAAG     360
TTCTTTGTAA GGTGTTTCGT GGACATCGCA TAGTTGGATA GAAACAATCC GATCAGCGGG     420
AACATTTTTG ATAGATTCAG CTGTTTGATT TGCTCTAGCC CAGTGCCATG TGTCACAAAT     480
AAGTTGCGCG TTATCTCGTC CGCATGCTTC TGCTACTCGC CAAGCTGCTT GTAAGTCTGC     540
TACACCGCTA TATGGCATAA ATTCTAAACC AATAATTAAT TCTTCTGCGC GGTCACATAA     600
TTCACCAAGC GCGACAATGA TTTGTTCCTC AGGGATTTTT TCAAGCAAAC CACAATTAAT     660
ATGTTTGACG CCAAATAATC GCGCCATGTG GAAAGTTGTT TGCTCTTTCT TTTGTTGTTC     720
TGCTGTACGA TCTTCGGCAG TTCCCCACTG GGTTATGTAC TCCACTTCTG TTACTTTCAT     780
GTTATGCTCG TCTAAAATCC GCAACATGTC TTCATCGGTT AATCCGGCAG CTAGTGCATC     840
TACATAATTT TCTGCACGCA AGCCAATTCC GTCAAAACCA TTTTCCGCAG CGACTTTCAC     900
TCGTTTAGGA AAAGATACCT CCGTTCCTAG TGTGTAAGAG CTAATCGTGA TGGGGCATTT     960
TTTTAGATTG CCATTTGCAT TTGTCATAAA AATTATCTCC TCTCCATAAT AAAAATTACA    1020
AGAAACTTTG ATAATATTTT CACAAACACC AGTAAAAAAA TAAATTCCAC TAAATTAAAA    1080
ATCTCTGATG TGATAACGCC TTCAATAGTT AAAAATGGAA CTGGACAGTT AACCTATTCT    1140
ACCGTATATT GGTTTTTAAG GAATAGTTTA TTTCACTGGC GTAACTACAG TTTAATTGTA    1200
TTATGACTAT TCCATAAAAA CAAATTGGTA TTGTTCTATT AATTGATAGA TAAATTGCAT    1260
AGATAACTTT TTAGTTAGGA GAGAAGCAT                                      1289
```

(2) INFORMATION FOR SEQ ID NO:31:

(i) SEQUENCE CHARACTERISTICS:
        (A) LENGTH: 1289 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (B) STRAIN: L MONO 1324 D.F.

(xi) SEQUENCE DESCRIPTION: SEQ ID NO:31:

```
ATGCTTCTCT CCTAACTAAA AAGTTATCTA TGCAATTTAT CTATCAATTA ATAGAACAAT      60
ACCAATTTGT TTTTATGGAA TAGTCATAAT ACAATTAAAC TGTAGTTACG CCAGTGAAAT     120
AAACTATTCC TTAAAAACCA ATATACGGTA GAATAGGTTA ACTGTCCAGT TCCATTTTTA     180
ACTATTGAAG GCGTTATCAC ATCAGAGATT TTAATTTAG TGGAATTTAT TTTTTTACTG     240
GTGTTTGTGA AATATTATC AAAGTTTCTT GTAATTTTA TTATGGAGAG GAGATAATTT     300
TTATGACAAA TGCAAATGGC AATCTAAAAA AATGCCCCAT CACGATTAGC TCTTACACAC     360
```

-continued

```
TAGGAACGGA GGTATCTTTT CCTAAACGAG TGAAAGTCGC TGCGGAAAAT GGTTTTGACG      420

GAATTGGCTT GCGTGCAGAA AATTATGTAG ATGCACTAGC TGCCGGATTA ACCGATGAAG      480

ACATGTTGCG GATTTTAGAC GAGCATAACA TGAAAGTAAC AGAAGTGGAG TACATAACCC      540

AGTGGGGAAC TGCCGAAGAT CGTACAGCAG AACAACAAAA GAAAGAGCAA ACAACTTTCC      600

ACATGGCGCG ATTATTTGGC GTCAAACATA TTAATTGTGG TTTGCTTGAA AAAATCCCTG      660

AGGAACAAAT CATTGTCGCG CTTGGTGAAT TATGTGACCG CGCAGAAGAA TTAATTATTG      720

GTTTAGAATT TATGCCATAT AGCGGTGTAG CAGACTTACA AGCAGCTTGG CGAGTAGCAG      780

AAGCATGCGG ACGAGATAAC GCGCAACTTA TTTGTGACAC ATGGCACTGG GCTAGAGCAA      840

ATCAAACAGC TGAATCTATC AAAAATGTTC CCGCTGATCG GATTGTTTCT ATCCAACTAT      900

GCGATGTCCA CGAAACACCT TACAAAGAAC TTCGTGAAGA ATCACTTCAT GATCGTTTAG      960

CTCCTGGAGA AGGATACGGA GATACGGTCG GTTTTGCAAA AATTTTAAAA GAGCATGGTG     1020

TAAATCCACG TGTGATGGGA GTTGAAGTTA TTTCAGACTC TATGGTAGCA ACTGGTTTAG     1080

AGTATGCCGC TCTTAAAGTA TACAATGCCA CGAAAAAAGT ATTAGACGAA GCATGGCCAG     1140

AGATTTCTCC ACGCTAAACA CCTACTTAGT TATGTGAAAA TGATAACGTA GTAGGAAGAC     1200

TCCCTGTGAA AGGAATGTGT TATTTTTGAA ATTTAATTCG ATGTTTTCAC CTATTGATAT     1260

CGGGCCGATG AAGGTGCCTA ACAGATTTG                                       1289
```

(2) INFORMATION FOR SEQ ID NO:32:

(i) SEQUENCE CHARACTERISTICS:
        (A) LENGTH: 284 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (B) STRAIN: L MONO ORF (xi) SEQUENCE DESCRIPTION: SEQ ID NO:32:

```
Met Thr Asn Ala Asn Gly Asn Leu Lys Lys Cys Pro Ile Thr Ile Ser
1               5                   10                  15

Ser Tyr Thr Leu Gly Thr Glu Val Ser Phe Pro Lys Arg Val Lys Val
            20                  25                  30

Ala Ala Glu Asn Gly Phe Asp Gly Ile Gly Leu Arg Ala Glu Asn Tyr
        35                  40                  45

Val Asp Ala Leu Ala Ala Gly Leu Thr Asp Glu Asp Met Leu Arg Ile
    50                  55                  60

Leu Asp Glu His Asn Met Lys Val Thr Glu Val Glu Tyr Ile Thr Gln
65                  70                  75                  80

Trp Gly Thr Ala Glu Asp Arg Thr Ala Glu Gln Gln Lys Lys Glu Gln
                85                  90                  95

Thr Thr Phe His Met Ala Arg Leu Phe Gly Val Lys His Ile Asn Cys
            100                 105                 110

Gly Leu Leu Glu Lys Ile Pro Glu Glu Gln Ile Ile Val Ala Leu Gly
        115                 120                 125

Glu Leu Cys Asp Arg Ala Glu Glu Leu Ile Ile Gly Leu Glu Phe Met
    130                 135                 140

Pro Tyr Ser Gly Val Ala Asp Leu Gln Ala Ala Trp Arg Val Ala Glu
145                 150                 155                 160

Ala Cys Gly Arg Asp Asn Ala Gln Leu Ile Cys Asp Thr Trp His Trp
                165                 170                 175
```

```
Ala Arg Ala Asn Gln Thr Ala Glu Ser Ile Lys Asn Val Pro Ala Asp
            180                 185                 190

Arg Ile Val Ser Ile Gln Leu Cys Asp Val His Glu Thr Pro Tyr Lys
            195                 200                 205

Glu Leu Arg Glu Glu Ser Leu His Asp Arg Leu Ala Pro Gly Glu Gly
            210                 215                 220

Tyr Gly Asp Thr Val Gly Phe Ala Lys Ile Leu Lys Glu His Gly Val
225                 230                 235                 240

Asn Pro Arg Val Met Gly Val Glu Val Ile Ser Asp Ser Met Val Ala
                245                 250                 255

Thr Gly Leu Glu Tyr Ala Ala Leu Lys Val Tyr Asn Ala Thr Lys Lys
            260                 265                 270

Val Leu Asp Glu Ala Trp Pro Glu Ile Ser Pro Arg
            275                 280
```

(2) INFORMATION FOR SEQ ID NO:33:

(i) SEQUENCE CHARACTERISTICS:
        (A) LENGTH: 1329 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: L INNOCUA 4450 D.F.

(xi) SEQUENCE DESCRIPTION: SEQ ID NO:33:

```
CATCTGTATT CGCATAGTTA TTACACATTG GAGATACAAC AAAACGATTT GGTACTCTCA      60

TAGGCCCGAT ATCAATCGGT GAGAACATCG AATTAAATTT CAAAAAAAAC ACTTCCCTTT     120

CAAGGTAGAA TCTTCTTGTT ACGTTACTTT TTTCACATGT TAATTATTT TTTTATTTGG      180

GAGAAATTTC TGGCCATGCT TCGTCCAATA CTTTTTTCGT TGCATTATAT ACTTTGATGG     240

CAGCATATTC TAAACCAGTT TCTACCATGG AGTCGGATAT AACTTCAACG CCCATAACAC     300

GGGGGTTAAC GCCATGCTCT TTCAAGATTC GAGCAAAACC GACTGTATCG CCGTATCCCT     360

CGCCAGGAGC AAGTCGGTCA TGGAGAGATT CTTCCCGAAG TTCTTTGTAA GGTGTTTCGT     420

GTACGTCACA TAATTGGATG GAAACAATCC GGTCAGCGGG AACATTTTTG ATTGATTCTG     480

CTGTTTGGTT TGCTCTAGCC GAGTGCCAAG TGTCGCAAAT TAGTTGTGCA TTATCCCTGC     540

CACATGCTTC AGCTACACGC CAAGCTGCTG CTAAGTCTGC TACACCACTG TATGGCATAA     600

ACTCTAAACC GATAATTAAT TCTTCCGCAC GGTCACACAA TTCACCGAGT GCCGTAATGA     660

TTTGTTCTTC GGGGATTTTT TCAAGCAAAC CGCAGTTAAT ATGTTTGACG CCGAATAAAC     720

GCGCCATGTG GAAAGTAGTT TGTTCTTTCT TTTGCTGTTC GGCTGTGCGG TCCTCGGCGG     780

TTCCCCACTG AGTTATGTAT TCTACTTCTG TTACTTTGAT GTTATGCTCA TCTAAAATCC     840

GCAACATATC TTCATCAGTT AATCCAGCGG CTAGTGCGTC TACATAGTTT TCTGCACGTA     900

AGCCAATTCC ATCAAAACCA TTTTCTGCTG CGATTCTCAC TCGTTCAGGA AAAGATACCT     960

CCGTTCCAAG CGTGTAAGAG CTGATCGTGA TTGGGCATTT TTTAGGTCG CCATTTGCAT    1020

TTGTCATAAA AATTATCTCC TCTCTAGAAT AAAAATTACA AGAAACTTTG ATAATATTTT    1080

CACAAACACC AGTAAAAAAA TAAATTCCCG TTCATTAAAT ATCGCTGATG TGATAACGCC    1140

TTCAATGTTT GAAATTTCAA CTGGACAGTT AACGTATTCT ACCGTATATT GGTTTTTAAG    1200

GAATAGTTTG TTCTGCTGGT GTAACTACAG TCTAATTGTA TTATGACTAT TCCATAAAAA    1260
```

```
CAAATTGGTA TTATTCTATT AATTGATAGA TAAATTGCAT AGATAATTTT TAGTAAGGAG    1320

AGAAGCCAT                                                             1329
```

(2) INFORMATION FOR SEQ ID NO:34:

(i) SEQUENCE CHARACTERISTICS:
        (A) LENGTH: 1329 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (B) STRAIN: L INNOCUA 4450 D.F.

(xi) SEQUENCE DESCRIPTION: SEQ ID NO:34:

```
ATGGCTTCTC TCCTTACTAA AAATTATCTA TGCAATTTAT CTATCAATTA ATAGAATAAT      60

ACCAATTTGT TTTTATGGAA TAGTCATAAT ACAATTAGAC TGTAGTTACA CCAGCAGAAC     120

AAACTATTCC TTAAAAACCA ATATACGGTA GAATACGTTA ACTGTCCAGT TGAAATTTCA     180

AACATTGAAG GCGTTATCAC ATCAGCGATA TTTAATGAAC GGGAATTTAT TTTTTTACTG     240

GTGTTTGTGA AAATATTATC AAAGTTTCTT GTAATTTTTA TTCTAGAGAG GAGATAATTT     300

TTATGACAAA TGCAAATGGC GACCTAAAAA AATGCCCAAT CACGATCAGC TCTTACACGC     360

TTGGAACGGA GGTATCTTTT CCTGAACGAG TGAGAATCGC AGCAGAAAAT GGTTTTGATG     420

GAATTGGCTT ACGTGCAGAA AACTATGTAG ACGCACTAGC CGCTGGATTA ACTGATGAAG     480

ATATGTTGCG GATTTTAGAT GAGCATAACA TCAAAGTAAC AGAAGTAGAA TACATAACTC     540

AGTGGGGAAC CGCCGAGGAC CGCACAGCCG AACAGCAAAA GAAAGAACAA ACTACTTTCC     600

ACATGGCGCG TTTATTCGGC GTCAAACATA TTAACTGCGG TTTGCTTGAA AAAATCCCCG     660

AAGAACAAAT CATTACGGCA CTCGGTGAAT TGTGTGACCG TGCGGAAGAA TTAATTATCG     720

GTTTAGAGTT TATGCCATAC AGTGGTGTAG CAGACTTAGC AGCAGCTTGG CGTGTAGCTG     780

AAGCATGTGG CAGGGATAAT GCACAACTAA TTTGCGACAC TTGGCACTCG GCTAGAGCAA     840

ACCAAACAGC AGAATCAATC AAAAATGTTC CCGCTGACCG GATTGTTCC ATCCAATTAT      900

GTGACGTACA CGAAACACCT TACAAAGAAC TTCGGGAAGA ATCTCTCCAT GACCGACTTG     960

CTCCTGGCGA GGGATACGGC GATACAGTCG GTTTTGCTCG AATCTTGAAA GAGCATGGCG    1020

TTAACCCCCG TGTTATGGGC GTTGAAGTTA TATCCGACTC CATGGTAGAA ACTGGTTTAG    1080

AATATGCTGC CATCAAAGTA TATAATGCAA CGAAAAAAGT ATTGGACGAA GCATGGCCAG    1140

AAATTTCTCC CAAATAAAAA AATAATTAAA CATGTGAAAA AAGTAACGTA ACAAGAAGAT    1200

TCTACCTTGA AAGGGAAGTG TTTTTTTTGA AATTTAATTC GATGTTCTCA CCGATTGATA    1260

TCGGGCCTAT GAGAGTACCA AATCGTTTTG TTGTATCTCC AATGTGTAAT AACTATGCGA    1320

ATACAGATG                                                            1329
```

(2) INFORMATION FOR SEQ ID NO:35:

(i) SEQUENCE CHARACTERISTICS:
        (A) LENGTH: 1319 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(B) STRAIN: L SEELIGERI 3327 D.F.

(xi) SEQUENCE DESCRIPTION: SEQ ID NO:35:

```
TATTTGCATA GTTATTACAC ATCGGCGAAA CCACGAAACG GTTTGGCACA CGCATAGGTC    60
CGATATCTAT TGGAGAAAAC ATCGAATTAA ATTTCAAAAA AAACACTTTC CTTTCAAAGG   120
GGGATTTTTA ACGTTATTAA TTTCACATAG CGATGCGTCA AGTTACTTTG GAGAAACTTC   180
TGGCCATGCT TCATCTAATA CTTTTTTAGT AGCATTATAA ACTTTAATTG CCGCATATTC   240
TAAACCTGTT TCTACCATCG AGTCTGAAAT CACTTCCACA CCCATAACAC GCGGATTTAC   300
ACCATGTTCT TTTAAAATAC GAGCAAAGCC TACAGTGTCG CCGTATCCTT CACCAGGTGC   360
TAATCGATCA TGGAGAGATT CTTCACGTAA TTCTTTGTAA GGAGTTTCGT GAACATCGCA   420
AAGTTGAATA GACACAATTC GGTCAGCAGG AATATTTTTG ATAGATTCTG CTGTTTGATT   480
TGCTCTAGCC CAGTGCCAAG TATCACAAAT CAGTTGCGCG TTATCTCGGC CACATGCTTC   540
TGCCACACGC CATGCTGCTG CTAAATCTGC TACACCGCTA TAAGGCATGA ATTCTAAACC   600
GATAATTAAT TCTTCAGCAC GGTCACAAAG TTCACCCAGA GCAGTAATGA TTTGTTCTTC   660
CGGAATCTTT TCAAGTAAAC CACAGTTAAT ATGTTTTACG CCGAATAAGC GCGCCATATG   720
AAAAGTGGTT TGTTCTTTCT TTTGTTGTTC TTTGGTGCGG TCGGAAGCGG TTCCCCATTG   780
CGTTATGTAT TCTACTTCTG TTACTTTGAT GTGATGTTCG TCCAAAATAC GCAACATATC   840
TTCATCGGTT AAGCCTGCTG CAAGTGCATC AACATAGTTT TCTGCACGTA AACCAATTCC   900
ATCAAAACCA TTTTCTGCTG CGATTCGTAC TCGTTCAGGA AAAGAAACCT CCGTTCCAAG   960
CGTGTAAGAA CTAATCGTGA TGGGGCATTT TTTTAAGTCG CCATTTACAT TTGTCATAAA  1020
AATTATCTCC TCTCTAGATT AAAATACAAG AAACTTTGAT AATAATTTCA CAATCACCAG  1080
CAAAAAAATA AATTCCTTTT TAGAATAAAA CGTCCTGAAG TGATAACGCA TTCAATCATT  1140
GAAAATCTGA CTGGACAGTT TTCGAATTCT ACCGTATATT GGTTTTTAAA GGATAGTTTG  1200
TCTCACTGGC TTAATTACAG TTTAATTGTA GTATGACTAT TCCATAAAAA CAAATTGGTA  1260
TTATTCTATT AATTGATAGA TAAATTGCAT AGATGCTTTT TAAAGAGGGG AGAAACCAT   1319
```

(2) INFORMATION FOR SEQ ID NO:36:

(i) SEQUENCE CHARACTERISTICS:
        (A) LENGTH: 1319 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (B) STRAIN: L SEELIGERI 3327 D.F.

(xi) SEQUENCE DESCRIPTION: SEQ ID NO:36:

```
ATGGTTTCTC CCCTCTTTAA AAAGCATCTA TGCAATTTAT CTATCAATTA ATAGAATAAT    60
ACCAATTTGT TTTTATGGAA TAGTCATACT ACAATTAAAC TGTAATTAAG CCAGTGAGAC   120
AAACTATCCT TTAAAAACCA ATATACGGTA GAATTCGAAA ACTGTCCAGT CAGATTTTCA   180
ATGATTGAAT GCGTTATCAC TTCAGGACGT TTTATTCTAA AAAGGAATTT ATTTTTTTGC   240
TGGTGATTGT GAAATTATTA TCAAAGTTTC TTGTATTTTA ATCTAGAGAG GAGATAATTT   300
TTATGACAAA TGTAAATGGC GACTTAAAAA AATGCCCCAT CACGATTAGT TCTTACACGC   360
TTGGAACGGA GGTTTCTTTT CCTGAACGAG TACGAATCGC AGCAGAAAAT GGTTTTGATG   420
```

| | |
|---|---|
| GAATTGGTTT ACGTGCAGAA AACTATGTTG ATGCACTTGC AGCAGGCTTA ACCGATGAAG | 480 |
| ATATGTTGCG TATTTTGGAC GAACATCACA TCAAAGTAAC AGAAGTAGAA TACATAACGC | 540 |
| AATGGGAAC CGCTTCCGAC CGCACCAAAG AACAACAAAA GAAAGAACAA ACCACTTTTC | 600 |
| ATATGGCGCG CTTATTCGGC GTAAAACATA TTAACTGTGG TTTACTTGAA AAGATTCCGG | 660 |
| AAGAACAAAT CATTACTGCT CTGGGTGAAC TTTGTGACCG TGCTGAAGAA TTAATTATCG | 720 |
| GTTTAGAATT CATGCCTTAT AGCGGTGTAG CAGATTTAGC AGCAGCATGG CGTGTGGCAG | 780 |
| AAGCATGTGG CCGAGATAAC GCGCAACTGA TTTGTGATAC TTGGCACTGG GCTAGAGCAA | 840 |
| ATCAAACAGC AGAATCTATC AAAAATATTC CTGCTGACCG AATTGTGTCT ATTCAACTTT | 900 |
| GCGATGTTCA CGAAACTCCT TACAAAGAAT TACGTGAAGA ATCTCTCCAT GATCGATTAG | 960 |
| CACCTGGTGA AGGATACGGC GACACTGTAG GCTTTGCTCG TATTTTAAAA GAACATGGTG | 1020 |
| TAAATCCGCG TGTTATGGGT GTGGAAGTGA TTTCAGACTC GATGGTAGAA ACAGGTTTAG | 1080 |
| AATATGCGGC AATTAAAGTT TATAATGCTA CTAAAAAAGT ATTAGATGAA GCATGGCCAG | 1140 |
| AAGTTTCTCC AAAGTAACTT GACGCATCGC TATGTGAAAT TAATAACGTT AAAAATCCCC | 1200 |
| CTTTGAAAGG AAAGTGTTTT TTTTGAAATT TAATTCGATG TTTTCTCCAA TAGATATCGG | 1260 |
| ACCTATGCGT GTGCCAAACC GTTTCGTGGT TTCGCCGATG TGTAATAACT ATGCAAATA | 1319 |

(2) INFORMATION FOR SEQ ID NO:37:

(i) SEQUENCE CHARACTERISTICS:
        (A) LENGTH: 1304 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: L WEISHIMERI 3359 D.F.

(xi) SEQUENCE DESCRIPTION: SEQ ID NO:37:

| | |
|---|---|
| ATTACACATT GGAGATACAA CAAACCGATT AGGTACTTTC ATCGGGCCAA TATCGATAGG | 60 |
| TGAGAACATC GAATTAAATT TCAAAAAAAA CACTTCCCTT TCAAGATGGA ATCTAGATTA | 120 |
| CGTTATTATT TTCACATGTT TGAATACATT ATTTTGGAGA AATTTCTGGC CAAGCCTCGT | 180 |
| CTAATACTTT TTTCGTGGCA TTATATACTT TAATTGCAGC ATATTCTAGA CCAGTTTCAA | 240 |
| CCATAGAGTC AGATATTACT TCGACTCCCA TCACTCGTGG ATTTACACCA TGTTCTTTTA | 300 |
| GGATGCGTGC AAAACCAACT GTATCTCCAT ATCCTTCACC AGGTGGTAGT CGGTCATGAA | 360 |
| GCGATTCTTC ACGAAGTTCT TTGTATGGCG TTTCATGAAC ATCACACAAT TGGATAGAAA | 420 |
| CAATTCGATC AGCTGGGACA TTTTTGATAG ACTCTGCTGT TTGGTTTGCT CTTGCCCAGT | 480 |
| GCCAAGTATC GCAAATTAGT TGTGCGTTAT CTCTACCACA TGCTTCTGCA ACACGCCAAG | 540 |
| CTGCGGCTAA GTCTGCTACT CCGCTATACG GCATAAATTC TAAACCGATG ATTAATTCTT | 600 |
| CGGCACGATC ACATAACTCA CCAAGAGCAG TAATTATTTG CTCTTCTGGA ATTTTTTCAA | 660 |
| GTAAACCGCA GTTAATATGT TTTACACCGA ATAACCGAGC CATGTGGAAA GTGGTTTGCT | 720 |
| CTTTTTGTTG TTGAGCATCG GTTCGGTCTG CTTCAGTTCC CCACTGAGTT ATGTATTCTA | 780 |
| CTTCTGTTAC TTTGATATTA TGCTTGTCTA AAATCTGCAG CATGTCATCA TCAGTTAAGC | 840 |
| CAGCTGCAAG AGCGTCTACA TAATTTTCAG CTCGCAAGCC AATTCCGTCA AAACCATTTT | 900 |
| CTGCTGCAAT CTTTACACGT TCTGGGAAGG AAACCTCCGT TCCAAGTGTG TAAGAACTAA | 960 |
| TCGTGATGGG GCATTTTTTT AAGTTGCCAT TTGAATTTGT CATAAAAATT ATCTCCTCTC | 1020 |

```
AAGAATGTAA ATTACAAGAA ACTTTGATAA TATTTTCACA AACACCAGTA AAAAAATAAA      1080

TTCCTTTTAA TTAAAAATCG CTGATGTGAT AACGCCTTCA ATGATCAAAA TACAACTGGA      1140

CAGTTAACGT ATTCTACCGT ATATTGGTTT TTAAGGAATA GTTTATTCTG CTGGTGTAAC      1200

TACAGTTTAA TTGTATTATG ACTATTCCAT AAAAACAAAT TGGTATTATT CTATTAATTG      1260

ATAGATAAAT TGCATAGATA CTTTTTAATA AGGGGAGAAG CCAT                       1304

(2) INFORMATION FOR SEQ ID NO:38:

(i) SEQUENCE CHARACTERISTICS:
         (A) LENGTH:  1304 base pairs
         (B) TYPE:  nucleic acid
         (C) STRANDEDNESS:  single
         (D) TOPOLOGY:  linear (ii) MOLECULE TYPE:  DNA (genomic)

(iv) ANTI-SENSE:  YES (vi) ORIGINAL SOURCE:
         (B) STRAIN:  L WEISHIMERI 3359 D.F.

(xi) SEQUENCE DESCRIPTION:  SEQ ID NO:38:

ATGGCTTCTC CCCTTATTAA AAAGTATCTA TGCAATTTAT CTATCAATTA ATAGAATAAT       60

ACCAATTTGT TTTTATGGAA TAGTCATAAT ACAATTAAAC TGTAGTTACA CCAGCAGAAT      120

AAACTATTCC TTAAAAACCA ATATACGGTA GAATACGTTA ACTGTCCAGT TGTATTTTGA      180

TCATTGAAGG CGTTATCACA TCAGCGATTT TTAATTAAAA GGAATTTATT TTTTTACTGG      240

TGTTTGTGAA AATATTATCA AAGTTTCTTG TAATTTACAT TCTTGAGAGG AGATAATTTT      300

TATGACAAAT TCAATGGCA ACTTAAAAAA ATGCCCCATC ACGATTAGTT CTTACACACT       360

TGGAACGGAG GTTTCCTTCC CAGAACGTGT AAAGATTGCA GCAGAAAATG GTTTTGACGG      420

AATTGGCTTG CGAGCTGAAA ATTATGTAGA CGCTCTTGCA GCTGGCTTAA CTGATGATGA      480

CATGCTGCAG ATTTTAGACA AGCATAATAT CAAAGTAACA GAAGTAGAAT ACATAACTCA      540

GTGGGAACT GAAGCAGACC GAACCGATGC TCAACAACAA AAAGAGCAAA CCACTTTCCA       600

CATGGCTCGG TTATTCGGTG TAAAACATAT TAACTGCGGT TTACTTGAAA AAATTCCAGA      660

AGAGCAAATA ATTACTGCTC TTGGTGAGTT ATGTGATCGT GCCGAAGAAT TAATCATCGG      720

TTTAGAATTT ATGCCGTATA GCGGAGTAGC AGACTTAGCC GCAGCTTGGC GTGTTGCAGA      780

AGCATGTGGT AGAGATAACG CACAACTAAT TTGCGATACT TGGCACTGGG CAAGAGCAAA      840

CCAAACAGCA GAGTCTATCA AAAATGTCCC AGCTGATCGA ATTGTTTCTA TCCAATTGTG      900

TGATGTTCAT GAAACGCCAT ACAAAGAACT TCGTGAAGAA TCGCTTCATG ACCGACTACC      960

ACCTGGTGAA GGATATGGAG ATACAGTTGG TTTTGCACGC ATCCTAAAAG AACATGGTGT     1020

AAATCCACGA GTGATGGGAG TCGAAGTAAT ATCTGACTCT ATGGTTGAAA CTGGTCTAGA     1080

ATATGCTGCA ATTAAAGTAT ATAATGCCAC GAAAAAAGTA TTAGACGAGG CTTGGCCAGA     1140

AATTTCTCCA AAATAATGTA TTCAAACATG TGAAATAAT AACGTAATCT AGATTCCATC     1200

TTGAAAGGGA AGTGTTTTTT TTGAAATTTA ATTCGATGTT CTCACCTATC GATATTGGCC     1260

CGATGAAAGT ACCTAATCGG TTTGTTGTAT CTCCAATGTG TAAT                      1304

(2) INFORMATION FOR SEQ ID NO:39:

(i) SEQUENCE CHARACTERISTICS:
         (A) LENGTH:  1328 base pairs
         (B) TYPE:  nucleic acid
         (C) STRANDEDNESS:  single
         (D) TOPOLOGY:  linear
```

(ii) MOLECULE TYPE:  DNA (genomic)

(vi) ORIGINAL SOURCE:
             (B) STRAIN:  L IVANOVII 3340 D.F.

(xi) SEQUENCE DESCRIPTION:  SEQ ID NO:39:

CCGTCTGTAT TTGCATAGTT ATTACACATT TGCGAAACAA CAAAACGGTT AGGTACTTTC      60

ATTGGTCCGA TATCTATTGG AGAAAACATC GAATTAAATT TCAAAAAAAA CACTTCCCTT     120

TCAAGATAGA ATTTTTCTTT CGTTATTAAT TTCACATAGT ATTGTATCAG ATTATTTTGG     180

TGACACTTCG GGCCATGCTT CGTCTAATAC TTTTTTTGTG GCATTGTATA CTTTAATTGC     240

GGTATATTCT AAGCCAGTTT CTACCATGGA ATCAGATATT ACTTCTACTC CCATGACACG     300

TGGACTTACA CCATGCTCTT TTAAAATACG AGCAAAACCA ATCGTGTCCC CGTATCCTTC     360

ACCAGGAGCT AGTCTATCAT GCAGTGACTC TTCGCGAAGC TCTTTATAGG GCGTTTCATG     420

GACGTCACAG AGTTGAATTG AAACAATCCG ATCAGCAGGA CATTTTTGA TAGATTCTGC      480

TGTTTGGTTT GCTCTTGCCC AGTGCCATGT GTCACAAATT AGTTGGGCGT TATCTCTGCC     540

GCAAGCCTCT GCCACACGCC ATGCTGCTGC CAAATCTGCT ACTCCGCTGT AAGGCATGAA     600

TTCTAAACCA ATAATCAATT CTTCTGCACG GTCGCAAAGT TCACCAAGAG CAGTAATGAT     660

TTGGTCTTCG GGGATTTTTT CCAATAAACC ACAATTAATA TGTTTTACAC CGAATAAGCG     720

AGCCATGTGG AAGGTAGTTT GTTCTTTCTT TTGTTGCTCG AAAGTGCGGT CAGAAGCGGT     780

TCCCCACTGC GTTATGTATT CTACTTCAGT AACTTTGATG TGATGCTCAT CTAAAATCCT     840

TAACATATCT TCATCAGTCA AGCCAGCTGC CAGTGCATCG ACATAATTTT CGGCGCGTAA     900

ACCAATTCCG TCAAAACCAT TTTCTGCTGC AATTCGTACT CGTTCAGGAA AAGAAACCTC     960

CGTTCCTAAG GTATAAGAGC TAATCGTGAT GGGGCATTTT TTTAGGTTGC CATTTGCATT    1020

TGTCATAAAA ATTATCTCCT CTCTAGATTA AACACAAGA AACTTTGATA ATGTTTTCAC     1080

AATCACCAGC AAAAAAATAA AATCCATTCA CTTAGAAAAC TTTCTAATGT GAGAACGCAT    1140

TCAATAGTTA GAAAATTGAC TGGACAGTTT TCACATTCTA CCGTATATTG GTTTTTAAAG    1200

GTTAGTTTAT TTCACTGGCA TAACTACTGT TTAATTGTAG TATGACTATT CCATAAAAAC    1260

AAATTGGTAT TATTCTATTA ATCGATAGAT AAATTGCATA GATTATTTTT AACAAGGAGA    1320

GAACCCAT                                                            1328

(2) INFORMATION FOR SEQ ID NO:40:

(i) SEQUENCE CHARACTERISTICS:
             (A) LENGTH:  1328 base pairs
             (B) TYPE:  nucleic acid
             (C) STRANDEDNESS:  single
             (D) TOPOLOGY:  linear (ii) MOLECULE TYPE:  DNA (genomic)

(iv) ANTI-SENSE:  YES (vi) ORIGINAL SOURCE:
             (B) STRAIN:  L IVANOVII 3340 D.F.

(xi) SEQUENCE DESCRIPTION:  SEQ ID NO:40:

ATGGGTTCTC TCCTTGTTAA AAATAATCTA TGCAATTTAT CTATCGATTA ATAGAATAAT      60

ACCAATTTGT TTTTATGGAA TAGTCATACT ACAATTAAAC AGTAGTTATG CCAGTGAAAT     120

AAACTAACCT TTAAAAACCA ATATACGGTA GAATGTGAAA ACTGTCCAGT CAATTTTCTA     180

ACTATTGAAT GCGTTCTCAC ATTAGAAAGT TTTCTAAGTG AATGGATTTT ATTTTTTTGC     240

```
TGGTGATTGT GAAAACATTA TCAAAGTTTC TTGTGTTTTA ATCTAGAGAG GAGATAATTT         300

TTATGACAAA TGCAAATGGC AACCTAAAAA AATGCCCCAT CACGATTAGC TCTTATACCT         360

TAGGAACGGA GGTTTCTTTT CCTGAACGAG TACGAATTGC AGCAGAAAAT GGTTTTGACG         420

GAATTGGTTT ACGCGCCGAA AATTATGTCG ATGCACTGGC AGCTGGCTTG ACTGATGAAG         480

ATATGTTAAG GATTTTAGAT GAGCATCACA TCAAAGTTAC TGAAGTAGAA TACATAACGC         540

AGTGGGGAAC CGCTTCTGAC CGCACTTTCG AGCAACAAAA GAAAGAACAA ACTACCTTCC         600

ACATGGCTCG CTTATTCGGT GTAAAACATA TTAATTGTGG TTTATTGGAA AAAATCCCCG         660

AAGACCAAAT CATTACTGCT CTTGGTGAAC TTTGCGACCG TGCAGAAGAA TTGATTATTG         720

GTTTAGAATT CATGCCTTAC AGCGGAGTAG CAGATTTGGC AGCAGCATGG CGTGTGGCAG         780

AGGCTTGCGG CAGAGATAAC GCCCAACTAA TTTGTGACAC ATGGCACTGG GCAAGAGCAA         840

ACCAAACAGC AGAATCTATC AAAAATGTAC CTGCTGATCG GATTGTTTCA ATTCAACTCT         900

GTGACGTCCA TGAAACGCCC TATAAAGAGC TTCGCGAAGA GTCACTGCAT GATAGACTAG         960

CTCCTGGTGA AGGATACGGG GACACGATTG GTTTTGCTCG TATTTTAAAA GAGCATGGTG        1020

TAAGTCCACG TGTCATGGGA GTAGAAGTAA TATCTGATTC CATGGTAGAA ACTGGCTTAG        1080

AATATACCGC AATTAAAGTA TACAATGCCA CAAAAAAAGT ATTAGACGAA GCATGGCCCG        1140

AAGTGTCACC AAAATAATCT GATACAATAC TATGTGAAAT TAATAACGAA AGAAAAATTC        1200

TATCTTGAAA GGGAAGTGTT TTTTTTGAAA TTTAATTCGA TGTTTTCTCC AATAGATATC        1260

GGACCAATGA AAGTACCTAA CCGTTTTGTT GTTTCGCAAA TGTGTAATAA CTATGCAAAT        1320

ACAGACGG                                                                 1328

(2) INFORMATION FOR SEQ ID NO:41:

(i) SEQUENCE CHARACTERISTICS:
        (A) LENGTH: 284 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (B) STRAIN: L MONO 647 ORF (xi) SEQUENCE DESCRIPTION: SEQ ID NO:41:

Met Thr Asn Ala Asn Gly Asn Leu Lys Lys Cys Pro Ile Thr Ile Ser
1               5                   10                  15

Ser Tyr Thr Leu Gly Thr Glu Val Ser Phe Pro Lys Arg Val Lys Val
            20                  25                  30

Ala Ala Glu Asn Gly Phe Asp Gly Ile Gly Leu Arg Ala Glu Asn Tyr
        35                  40                  45

Val Asp Ala Leu Ala Ala Gly Leu Thr Asp Glu Asp Met Leu Arg Ile
50                  55                  60

Leu Asp Glu His Asn Met Lys Val Thr Glu Val Glu Tyr Ile Thr Gln
65                  70                  75                  80

Trp Gly Thr Ala Glu Asp Arg Thr Ala Glu Gln Lys Lys Glu Gln
                85                  90                  95

Thr Thr Phe His Met Ala Arg Leu Phe Gly Val Lys His Ile Asn Cys
            100                 105                 110

Gly Leu Leu Glu Lys Ile Pro Glu Glu Gln Ile Ile Val Ala Leu Gly
        115                 120                 125

Glu Leu Cys Asp Arg Ala Glu Glu Leu Ile Ile Gly Leu Glu Phe Met
130                 135                 140
```

```
Pro Tyr Ser Gly Val Ala Asp Leu Gln Ala Ala Trp Arg Val Ala Glu
145                 150                 155                 160

Ala Cys Gly Arg Asp Asn Ala Gln Leu Ile Cys Asp Thr Trp His Trp
                165                 170                 175

Ala Arg Ala Asn Gln Thr Ala Glu Ser Ile Lys Asn Val Pro Ala Asp
            180                 185                 190

Arg Ile Val Ser Ile Gln Leu Cys Asp Val His Glu Thr Pro Tyr Lys
        195                 200                 205

Glu Leu Arg Glu Glu Ser Leu His Asp Arg Leu Ala Pro Gly Glu Gly
    210                 215                 220

Tyr Gly Asp Thr Val Gly Phe Ala Lys Ile Leu Lys Glu His Gly Val
225                 230                 235                 240

Asn Pro Arg Val Met Gly Val Glu Val Ile Ser Asp Ser Met Val Ala
                245                 250                 255

Thr Gly Leu Glu Tyr Ala Ala Leu Lys Val Tyr Asn Ala Thr Lys Lys
            260                 265                 270

Val Leu Asp Glu Ala Trp Pro Glu Ile Ser Pro Arg
        275                 280
```

(2) INFORMATION FOR SEQ ID NO:42:

(i) SEQUENCE CHARACTERISTICS:
        (A) LENGTH: 284 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (B) STRAIN: L MONO 4450 ORF (xi) SEQUENCE DESCRIPTION: SEQ ID NO:42:

```
Met Thr Asn Ala Asn Gly Asp Leu Lys Lys Cys Pro Ile Thr Ile Ser
1               5                   10                  15

Ser Tyr Thr Leu Gly Thr Glu Val Ser Phe Pro Glu Arg Val Arg Ile
            20                  25                  30

Ala Ala Glu Asn Gly Phe Asp Gly Ile Gly Leu Arg Ala Glu Asn Tyr
        35                  40                  45

Val Asp Ala Leu Ala Ala Gly Leu Thr Asp Glu Asp Met Leu Arg Ile
50                  55                  60

Leu Asp Glu His Asn Ile Lys Val Thr Glu Val Glu Tyr Ile Thr Gln
65                  70                  75                  80

Trp Gly Thr Ala Glu Asp Arg Thr Ala Glu Gln Gln Lys Lys Glu Gln
                85                  90                  95

Thr Thr Phe His Met Ala Arg Leu Phe Gly Val Lys His Ile Asn Cys
            100                 105                 110

Gly Leu Leu Glu Lys Ile Pro Glu Glu Gln Ile Ile Thr Ala Leu Gly
        115                 120                 125

Glu Leu Cys Asp Arg Ala Glu Glu Leu Ile Ile Gly Leu Glu Phe Met
    130                 135                 140

Pro Tyr Ser Gly Val Ala Asp Leu Ala Ala Trp Arg Val Ala Glu
145                 150                 155                 160

Ala Cys Gly Arg Asp Asn Ala Gln Leu Ile Cys Asp Thr Trp His Ser
                165                 170                 175

Ala Arg Ala Asn Gln Thr Ala Glu Ser Ile Lys Asn Val Pro Ala Asp
            180                 185                 190
```

```
Arg Ile Val Ser Ile Gln Leu Cys Asp Val His Glu Thr Pro Tyr Lys
            195                 200                 205

Glu Leu Arg Glu Glu Ser Leu His Asp Arg Leu Ala Pro Gly Glu Gly
            210                 215                 220

Tyr Gly Asp Thr Val Gly Phe Ala Arg Ile Leu Lys Glu His Gly Val
225                 230                 235                 240

Asn Pro Arg Val Met Gly Val Glu Val Ile Ser Asp Ser Met Val Glu
                245                 250                 255

Thr Gly Leu Glu Tyr Ala Ala Ile Lys Val Tyr Asn Ala Thr Lys Lys
            260                 265                 270

Val Leu Asp Gln Ala Trp Pro Glu Ile Ser Pro Lys
            275                 280
```

(2) INFORMATION FOR SEQ ID NO:43:

(i) SEQUENCE CHARACTERISTICS:

(A) LENGTH: 284 amino acids
        (B) TYPE: amino acid (C) STRANDEDNESS: unknown
        (D) TOPOLOGY: unknown (ii) MOLECULE TYPE: protein (vi) ORIGINAL SOURCE:
        (B) STRAIN: L MONO 3340 ORF (xi) SEQUENCE DESCRIPTION: SEQ ID NO:43:

```
Met Thr Asn Ala Asn Gly Asn Leu Lys Lys Cys Pro Ile Thr Ile Ser
1               5                   10                  15

Ser Tyr Thr Leu Gly Thr Glu Val Ser Phe Pro Glu Arg Val Arg Ile
            20                  25                  30

Ala Ala Glu Asn Gly Phe Asp Gly Ile Gly Leu Arg Ala Glu Asn Tyr
            35                  40                  45

Val Asp Ala Leu Ala Ala Gly Leu Thr Asp Glu Asp Met Leu Arg Ile
        50                  55                  60

Leu Asp Glu His His Ile Lys Val Thr Glu Val Glu Tyr Ile Thr Gln
65                  70                  75                  80

Trp Gly Thr Ala Ser Asp Arg Thr Phe Glu Gln Gln Lys Lys Glu Gln
            85                  90                  95

Thr Thr Phe His Met Ala Arg Leu Phe Gly Val Lys His Ile Asn Cys
                100                 105                 110

Gly Leu Leu Glu Lys Ile Pro Glu Asp Gln Ile Ile Thr Ala Leu Gly
            115                 120                 125

Glu Leu Cys Asp Arg Ala Glu Glu Leu Ile Ile Gly Leu Glu Phe Met
        130                 135                 140

Pro Tyr Ser Gly Val Ala Asp Leu Ala Ala Ala Trp Arg Val Ala Glu
145                 150                 155                 160

Ala Cys Gly Arg Asp Asn Ala Gln Leu Ile Cys Asp Thr Trp His Trp
                165                 170                 175

Ala Arg Ala Asn Gln Thr Ala Glu Ser Ile Lys Asn Val Pro Ala Asp
            180                 185                 190

Arg Ile Val Ser Ile Gln Leu Cys Asp Val His Glu Thr Pro Tyr Lys
            195                 200                 205

Glu Leu Arg Glu Glu Ser Leu His Asp Arg Leu Ala Pro Gly Glu Gly
            210                 215                 220

Tyr Gly Asp Thr Ile Gly Phe Ala Arg Ile Leu Lys Glu His Gly Val
225                 230                 235                 240
```

-continued

```
Ser Pro Arg Val Met Gly Val Glu Val Ile Ser Asp Ser Met Val Glu
            245                 250                 255

Thr Gly Leu Glu Tyr Thr Ala Ile Lys Val Tyr Asn Ala Thr Lys Lys
            260                 265                 270

Val Leu Asp Glu Ala Trp Pro Glu Val Ser Pro Lys
            275                 280
```

(2) INFORMATION FOR SEQ ID NO:44:

(i) SEQUENCE CHARACTERISTICS:

(A) LENGTH: 284 amino acids
        (B) TYPE: amino acid (C) STRANDEDNESS: unknown
        (D) TOPOLOGY: unknown (ii) MOLECULE TYPE: protein (vi) ORIGINAL SOURCE:
        (B) STRAIN: L MONO 3327 ORF (xi) SEQUENCE DESCRIPTION: SEQ ID NO:44:

```
Met Thr Asn Val Asn Gly Asp Leu Lys Lys Cys Pro Ile Thr Ile Ser
1               5                   10                  15

Ser Tyr Thr Leu Gly Thr Glu Val Ser Phe Pro Glu Arg Val Arg Ile
            20                  25                  30

Ala Ala Glu Asn Gly Phe Asp Gly Ile Gly Leu Arg Ala Glu Asn Tyr
            35                  40                  45

Val Asp Ala Leu Ala Ala Gly Leu Thr Asp Glu Asp Met Leu Arg Ile
            50                  55                  60

Leu Asp Glu His His Ile Lys Val Thr Glu Val Glu Tyr Ile Thr Gln
65                  70                  75                  80

Trp Gly Thr Ala Ser Asp Arg Thr Lys Glu Gln Gln Lys Lys Glu Gln
            85                  90                  95

Thr Thr Phe His Met Ala Arg Leu Phe Gly Val Lys His Ile Asn Cys
            100                 105                 110

Gly Leu Leu Glu Lys Ile Pro Glu Glu Gln Ile Ile Thr Ala Leu Gly
            115                 120                 125

Glu Leu Cys Asp Arg Ala Glu Glu Leu Ile Ile Gly Leu Glu Phe Met
            130                 135                 140

Pro Tyr Ser Gly Val Ala Asp Leu Ala Ala Ala Trp Arg Val Ala Glu
145                 150                 155                 160

Ala Cys Gly Arg Asp Asn Ala Gln Leu Ile Cys Asp Thr Trp His Trp
            165                 170                 175

Ala Arg Ala Asn Gln Thr Ala Glu Ser Ile Lys Asn Ile Pro Ala Asp
            180                 185                 190

Arg Ile Val Ser Ile Gln Leu Cys Asp Val His Glu Thr Pro Tyr Lys
            195                 200                 205

Glu Leu Arg Glu Glu Ser Leu His Asp Arg Leu Ala Pro Gly Glu Gly
            210                 215                 220

Tyr Gly Asp Thr Val Gly Phe Ala Arg Ile Leu Lys Glu His Gly Val
225                 230                 235                 240

Asn Pro Arg Val Met Gly Val Glu Val Ile Ser Asp Ser Met Val Glu
            245                 250                 255

Thr Gly Leu Glu Tyr Ala Ala Ile Lys Val Tyr Asn Ala Thr Lys Lys
            260                 265                 270

Val Leu Asp Glu Ala Trp Pro Glu Val Ser Pro Lys
            275                 280
```

(2) INFORMATION FOR SEQ ID NO:45:

(i) SEQUENCE CHARACTERISTICS:
        (A) LENGTH: 284 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (B) STRAIN: L MONO 3359 ORF (xi) SEQUENCE DESCRIPTION: SEQ ID NO:45:

```
Met Thr Asn Ser Asn Gly Asn Leu Lys Lys Cys Pro Ile Thr Ile Ser
 1               5                  10                  15

Ser Tyr Thr Leu Gly Thr Glu Val Ser Phe Pro Glu Arg Val Lys Ile
            20                  25                  30

Ala Ala Glu Asn Gly Phe Asp Gly Ile Gly Leu Arg Ala Glu Asn Tyr
        35                  40                  45

Val Asp Ala Leu Ala Ala Gly Leu Thr Asp Asp Met Leu Gln Ile
 50                  55                  60

Leu Asp Lys His Asn Ile Lys Val Thr Glu Val Glu Tyr Ile Thr Gln
 65                  70                  75                  80

Trp Gly Thr Glu Ala Asp Arg Thr Asp Ala Gln Gln Gln Lys Glu Gln
                85                  90                  95

Thr Thr Phe His Met Ala Arg Leu Phe Gly Val Lys His Ile Asn Cys
            100                 105                 110

Gly Leu Leu Glu Lys Ile Pro Glu Glu Gln Ile Ile Thr Ala Leu Gly
        115                 120                 125

Glu Leu Cys Asp Arg Ala Glu Glu Leu Ile Ile Gly Leu Glu Phe Met
130                 135                 140

Pro Tyr Ser Gly Val Ala Asp Leu Ala Ala Ala Trp Arg Val Ala Glu
145                 150                 155                 160

Ala Cys Gly Arg Asp Asn Ala Gln Leu Ile Cys Asp Thr Trp His Trp
                165                 170                 175

Ala Arg Ala Asn Gln Thr Ala Glu Ser Ile Lys Asn Val Pro Ala Asp
            180                 185                 190

Arg Ile Val Ser Ile Gln Leu Cys Asp Val His Glu Thr Pro Tyr Lys
        195                 200                 205

Glu Leu Arg Glu Glu Ser Leu His Asp Arg Leu Pro Pro Gly Glu Gly
    210                 215                 220

Tyr Gly Asp Thr Val Gly Phe Ala Arg Ile Leu Lys Glu His Gly Val
225                 230                 235                 240

Asn Pro Arg Val Met Gly Val Glu Val Ile Ser Asp Ser Met Val Glu
                245                 250                 255

Thr Gly Leu Glu Tyr Ala Ala Ile Lys Val Tyr Asn Ala Thr Lys Lys
            260                 265                 270

Val Leu Asp Glu Ala Trp Pro Glu Ile Ser Pro Lys
        275                 280
```

(2) INFORMATION FOR SEQ ID NO:46:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

GCGATACGAC AAATCTGTTA GGCACC                                   26

(2) INFORMATION FOR SEQ ID NO:47:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

GAGATACAAC AAAACGATTT GGTACT                                   26

(2) INFORMATION FOR SEQ ID NO:48:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

GCGAAACCAC GAAACGGTTT GGCACA                                   26

(2) INFORMATION FOR SEQ ID NO:49:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

GAGATACAAC AAACCGATTA GGTACT                                   26

(2) INFORMATION FOR SEQ ID NO:50:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

GCGAAACAAC AAAACGGTTA GGTACT                                   26

(2) INFORMATION FOR SEQ ID NO:51:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
CATTCCTTTC ACAGGGAGTC TTCCTAC                                                27

(2) INFORMATION FOR SEQ ID NO:52:

(i) SEQUENCE CHARACTERISTICS:
          (A) LENGTH:  28 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:52:

CTTCCCTTTC AAGGTAGAAT CTTCTTGT                                               28

(2) INFORMATION FOR SEQ ID NO:53:

(i) SEQUENCE CHARACTERISTICS:
          (A) LENGTH:  25 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:53:

CTTTCCTTTC AAAGGGGAT TTTTA                                                   25

(2) INFORMATION FOR SEQ ID NO:54:

(i) SEQUENCE CHARACTERISTICS:
          (A) LENGTH:  26 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:54:

CTTCCCTTTC AAGATGGAAT CTAGAT                                                 26

(2) INFORMATION FOR SEQ ID NO:55:

(i) SEQUENCE CHARACTERISTICS:
          (A) LENGTH:  28 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:55:

CTTCCCTTTC AAGATAGAAT TTTTTCTT                                               28

(2) INFORMATION FOR SEQ ID NO:56:

(i) SEQUENCE CHARACTERISTICS:
          (A) LENGTH:  26 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:56:

TAGTTGGATG GAAACAATCC GATCAG                                                 26

(2) INFORMATION FOR SEQ ID NO:57:
```

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:57:

TAGTTGGATA GAAACAATCC GATCAG                    26

(2) INFORMATION FOR SEQ ID NO:58:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

TAATTGGATG GAAACAATCC GGTCAG                    26

(2) INFORMATION FOR SEQ ID NO:59:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

AAGTTGAATA GACACAATTC GGTCAG                    26

(2) INFORMATION FOR SEQ ID NO:60:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

CAATTGGATA GAAACAATTC GATCAG                    26

(2) INFORMATION FOR SEQ ID NO:61:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

GAGTTGAATT GAAACAATCC GATCAG                    26

(2) INFORMATION FOR SEQ ID NO:62:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

TTTGTTGTTC TGCTGTACGA TCTTCGG                27

(2) INFORMATION FOR SEQ ID NO:63:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:63:

TTTGCTGTTC GGCTGTGCGG TCCTCGG                27

(2) INFORMATION FOR SEQ ID NO:64:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:64:

TTTGTTGTTC TTTGGTGCGG TCGGAAG                27

(2) INFORMATION FOR SEQ ID NO:65:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:65:

GTTGTTGAGC ATCGGTTCGG TCTGCTT                27

(2) INFORMATION FOR SEQ ID NO:66:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:66:

TTTGTTGCTC GAAAGTGCGG TCAGAAG                27

(2) INFORMATION FOR SEQ ID NO:67:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:67:

```
AAATCCCTGA GGAACAAATC ATCGTC                                              26

(2) INFORMATION FOR SEQ ID NO:68:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:68:

AAATCCCTGA GGAACAAATC ATTGTC                                              26

(2) INFORMATION FOR SEQ ID NO:69:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:69:

AAATCCCCGA AGAACAAATC ATTACG                                              26

(2) INFORMATION FOR SEQ ID NO:70:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:70:

AGATTCCGGA AGAACAAATC ATTACT                                              26

(2) INFORMATION FOR SEQ ID NO:71:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:71:

AAATTCCAGA AGAGCAAATA ATTACT                                              26

(2) INFORMATION FOR SEQ ID NO:72:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:72:

AAATCCCCGA AGACCAAATC ATTACT                                              26

(2) INFORMATION FOR SEQ ID NO:73:
```

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:73:

GGTAGAATAG GTTAACTGTC CAGTTCC                 27

(2) INFORMATION FOR SEQ ID NO:74:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

GGTAGAATAC GTTAACTGTC CAGTTGA                 27

(2) INFORMATION FOR SEQ ID NO:75:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

GGTAGAATTC GAAAACTGTC CAGTCAG                 27

(2) INFORMATION FOR SEQ ID NO:76:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

GGTAGAATAC GTTAACTGTC CAGTTGT                 27

(2) INFORMATION FOR SEQ ID NO:77:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

GGTAGAATGT GAAAACTGTC CAGTCAA                 27

(2) INFORMATION FOR SEQ ID NO:78:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

TACAATTAGA CTGTAGTTAC GCCAGTGA                28

(2) INFORMATION FOR SEQ ID NO:79:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:79:

TACAATTAAA CTGTAGTTAC GCCAGTGA                28

(2) INFORMATION FOR SEQ ID NO:80:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:80:

TACAATTAGA CTGTAGTTAC ACCAGCAG                28

(2) INFORMATION FOR SEQ ID NO:81:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:81:

TACAATTAAA CTGTAATTAA GCCAGTGA                28

(2) INFORMATION FOR SEQ ID NO:82:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:82:

TACAATTAAA CTGTAGTTAC ACCAGCAG                28

(2) INFORMATION FOR SEQ ID NO:83:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:83:

```
TACAATTAAA CAGTAGTTAT GCCAGTGA                                              28

(2) INFORMATION FOR SEQ ID NO:84:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:84:

TTTGATAGAT TCTGCTGTTT GGTTTGCTCT                                            30

(2) INFORMATION FOR SEQ ID NO:85:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:85:

TTTGATAGAT TCAGCTGTTT GATTTGCTCT                                            30

(2) INFORMATION FOR SEQ ID NO:86:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:86:

TTTGATTGAT TCTGCTGTTT GGTTTGCTCT                                            30

(2) INFORMATION FOR SEQ ID NO:87:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:87:

TTTGATAGAT TCTGCTGTTT GATTTGCTCT                                            30

(2) INFORMATION FOR SEQ ID NO:88:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:88:

TTTGATAGAC TCTGCTGTTT GGTTTGCTCT                                            30

(2) INFORMATION FOR SEQ ID NO:89:
```

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:89:

TGCTGTTTGG TTTGCTCTAG CCCAGTGCCA                                              30

(2) INFORMATION FOR SEQ ID NO:90:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:90:

AGCTGTTTGA TTTGCTCTAG CCCAGTGCCA                                              30

(2) INFORMATION FOR SEQ ID NO:91:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:91:

TGCTGTTTGG TTTGCTCTAG CCGAGTGCCA                                              30

(2) INFORMATION FOR SEQ ID NO:92:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:92:

TGCTGTTTGA TTTGCTCTAG CCCAGTGCCA                                              30

(2) INFORMATION FOR SEQ ID NO:93:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:93:

TGCTGTTTGG TTTGCTCTTG CCCAGTGCCA                                              30

(2) INFORMATION FOR SEQ ID NO:94:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:94:

TTGCATTTGT CATAAAAATT ATCTCCTCTC                                    30

(2) INFORMATION FOR SEQ ID NO:95:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:95:

TTACATTTGT CATAAAAATT ATCTCCTCTC                                    30

(2) INFORMATION FOR SEQ ID NO:96:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:96:

TTGAATTTGT CATAAAAATT ATCTCCTCTC                                    30

(2) INFORMATION FOR SEQ ID NO:97:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:97:

CGCTGCGGAA AACGGTTTTG ACGGATTTGG                                    30

(2) INFORMATION FOR SEQ ID NO:98:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:98:

CGCTGCGGAA AAAGGTTTTG ACGGATTTGG                                    30

(2) INFORMATION FOR SEQ ID NO:99:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:99:

```
CGCAGCAGAA AACGGTTTTG ATGGATTTGG                                        30

(2) INFORMATION FOR SEQ ID NO:100:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:100:

TGCAGCAGAA AACGGTTTTG ACGGATTTGG                                        30

(2) INFORMATION FOR SEQ ID NO:101:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:101:

AAAAAAATGC CCCATCACGA TTAGCTCTTA                                        30

(2) INFORMATION FOR SEQ ID NO:102:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:102:

AAAAAAATGC CCAATCACGA TCAGCTCTTA                                        30

(2) INFORMATION FOR SEQ ID NO:103:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:103:

AAAAAAATGC CCCATCACGA TTAGTTCTTA                                        30

(2) INFORMATION FOR SEQ ID NO:104:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:104:

AAATGCAAAT GGCAACCTAA AAAAATGCCC                                        30

(2) INFORMATION FOR SEQ ID NO:105:
```

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:105:

AAATGCAAAT GGCAATCTAA AAAAATGCCC                                             30

(2) INFORMATION FOR SEQ ID NO:106:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:106:

AAATGCAAAT GGCGACCTAA AAAAATGCCC                                             30

(2) INFORMATION FOR SEQ ID NO:107:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:107:

AAATGTAAAT GGCGACTTAA AAAAATGCCC                                             30

(2) INFORMATION FOR SEQ ID NO:108:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:108:

AAATTCAAAT GGCAACTTAA AAAAATGCCC                                             30

(2) INFORMATION FOR SEQ ID NO:109:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:109:

CAATACCAAT TTGTTTTTAT GGAATAGTCA                                             30

(2) INFORMATION FOR SEQ ID NO:110:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:110:

TAATACCAAT TTGTTTTTAT GGAATAGTCA                30